(12) United States Patent
Kapitonov et al.

(10) Patent No.: US 6,280,989 B1
(45) Date of Patent: Aug. 28, 2001

(54) SIALYLTRANSFERASES

(76) Inventors: Dmitri Kapitonov, 1327 Spruce St., Apt. 5E, Philadelphia, PA (US) 19107; Robert K. Yu, 306 Cheswick, Richmond, VA (US) 23229

(*) Notice: Subject to any disclaimer, the term of this patent is extended or adjusted under 35 U.S.C. 154(b) by 0 days.

(21) Appl. No.: 09/334,601

(22) Filed: Jun. 17, 1999

(51) Int. Cl.[7] .............................. C12N 9/10; C12N 15/54
(52) U.S. Cl. .................. 435/193; 435/252.3; 435/320.1; 526/23.2
(58) Field of Search .......................... 435/193, 252.3, 435/320.1; 536/23.2

(56) References Cited

U.S. PATENT DOCUMENTS

| | | | |
|---|---|---|---|
| 5,409,817 | 4/1995 | Ito et al. ................................. | 435/74 |
| 5,494,790 | 2/1996 | Sasaki et al. ........................... | 435/6 |

FOREIGN PATENT DOCUMENTS

| | | |
|---|---|---|
| 0 890 645 A2 | 7/1998 | (EP). |
| WO 97/47749 | 12/1997 | (WO). |

OTHER PUBLICATIONS

Kono, M., et al. (1998) Biochem. Biophys. Res. Commun. 253 (1), 170–175.*
Copies of sequence search.*
Min–Ling Chang et al., *Glycobiology*, vol. 5, No. 3 pp. 319–325 (1995).
E. R. Sjoberg et al., *J. of Biol. Chem.*, vol. 271, No. 13 pp. 7450–7459 (1996).
Jiyan Ma et al., *J. of Biol. Chem.*, vol. 272, No. 1 pp. 672–679 (1997).
Peter Lance et al., *Biochem. and Biophys. Res. Comm.*, vol. 164, No. 1 pp. 225–232 (1989).
N.–W. Lo et al., *Glycobiology*, vol. 6, No. 3 pp. 271–279 (1996).
M. Kono et al., *J. of Biol. Chem.*, vol. 271, No. 46 pp. 29366–29371 (1996).
A. Tsunoda et al., *Biochemistry*, vol. 34, pp. 9356–9367 (1995).
A. Ishii et al., *J. of Biol. Chem.*, vol. 273, No. 48 pp. 31652–31655 (1998).
K. Sasaki, *Trends in Glycoscience and Gylcotechnology*, vol. 8, No. 41 pp. 195–215 (1996).
U. Grundmann et al., *Nucleic Acid Res.*, vol. 18, No. 3 p. 667 (1990).

* cited by examiner

*Primary Examiner*—Charles L. Patterson, Jr.
(74) *Attorney, Agent, or Firm*—Millen White Zelano & Branigan

(57) ABSTRACT

The present invention relates to isolated sialyltransferases, such as human or mouse GM3 synthase, human or mouse 4ST3GalVI, or human 7STGalNAcV sialyltransferase polypeptide, biologically-active polypeptide fragments thereof, and nucleic acids which code for it. This polypeptide has various activities including sialyltransferase activity. The invention relates to all aspects of sialyltransferase, or homologs thereof, including assays for modulators, activators, ligands, etc. The invention also relates to sialyltransferases expressed in cells and methods of using such cells to engineer specific sugar chains.

13 Claims, 24 Drawing Sheets

```
H     1 ..........................................................GG  60
M       GGGCTGAATTGGCGCGAGCGCGGCGCCGGGGGCTGGCTGGGGCGCGGGGCCCCGGGCTGG
        ---------+---------+---------+---------+---------+---------+

H    61 CGGCCGGCCGGCGCCCCCTCATTAGTATGCGGACGAAGGCGGCGGGCTGCGCGGAGCGGC 120
M       CGGCTTGCCAGCGCTCCCTCCCTAGCATGCACACAGAGGCGGTGGGCGGCGCGGCGCGGA
        ---------+---------+---------+---------+---------+---------+

H                    . . . . . . . . .  M  R  T  K  A  A  G  C  A  E  R  R
M                                       M  H  T  E  A  V  G  G  A  A  R  R
                                         1

H   121 GTCCCCTGCAGCCGCGGACCGAGGCAGCGGCGGCACCTGCCGGCCGAGCAATGCCAAGTG 180
M       GGCCCCAGAAGCTGCGAAGCCAAGCAGCGGCA...CCTGCCTGCCGAGCAATGCCAAGTG
        ---------+---------+---------+---------+---------+---------+

H         P  L  Q  P  R  T  E  A  A  A  A  P  A  G  R  A  M  P  S  E
M         P  Q  K  L  R  S  Q  A  A  A  .  P  A  C  R  A  M  P  S  E
                                                          2

H   181 AGTACACCTATGTGAAACTGAGAAGTGATTGCTCGAGGCCTTCCCTGCAATGGTACACCC 240
M       AGTTCACCTCTGCAAAGCTGAGAAGTGATTGCTCAAGGACCTCCCTGCAATGGTACACCC
        ---------+---------+---------+---------+---------+---------+

H         Y  T  Y  V  K  L  R  S  D  C  S  R  P  S  L  Q  W  Y  T  R
M         F  T  S  A  K  L  R  S  D  C  S  R  T  S  L  Q  W  Y  T  R

H   241 GAGCTCAAAGCAAGATGAGAAGGCCCAGCTTGTTATTAAAAGACATCCTCAAATGTACAT 300
M       GAACCCAGCACAAGATGAGAAGACCCAGCTTGTTAATAAAAGACATCTGCAAGTGCACGT
        ---------+---------+---------+---------+---------+---------+

H         A  Q  S  K  M  R  R  P  S$^{CP}$ L  L  L  K  D  I  L  K  C  T  L 16
M         T  Q  H  K  M  R  R  P  S$^{CP}$ L  L  I  K  D  I  C  K  C  T  L
                                 3

H   301 TGCTTGTGTTTGGAGTGTGGATCCTTTATATCCTCAAGTTAAATTATACTACTGAAGAAT 360
M       TGGTTGCATTTGGAGTCTGGCTCCTGTACATCCTCATTTTGAATTACACCGCTGAAGAAT
        ---------+---------+---------+---------+---------+---------+

H         L  V  F  G  V  W  I  L  Y  I  L  K  L  N$^{G}$ Y  T$^{CK}$ T  E  E  C 36
M         V  A  F  G  V  W  L  L  Y  I  L  I  L  N$^{G}$ Y  T$^{CK}$ A  E  E  C
                                                    ↑1

H   361 GTGACATGAAAAAAATGCATTATGTGGACCCTGACCGTGTAAAGAGAGCTCAGAAATATG 420
M       GTGACATGAAAAGAATGCACTATGTGGACCCTGACCGGATAAAGAGAGCTCAGAGCTATG
        ---------+---------+---------+---------+---------+---------+

H         D  M  K  K  M  H  Y  V  D  P  D  R  V  K  R  A  Q  K  Y  A 56
M         D  M  K  R  M  H  Y  V  D  P  D  R  I  K  R  A  Q  S  Y  A

H   421 CTCAGCAAGTCTTGCAGAAGGAATGTCGTCCCAAGTTTGCCAAGACATCAATGGCGCTGT 480
M       CTCAGGAAGTCTTGCAGAAGGAATGTCGGCCCAGGTACGCGAAGACGGCTATGGCTCTGT
        ---------+---------+---------+---------+---------+---------+

H         Q  Q  V  L  Q  K  E  C  R  P  K  F  A  K  T  S  [M] A  L  L 76
M         Q  E  V  L  Q  K  E  C  R  P  R  Y  A  K  T  A  [M] A  L  L

H   481 TATTTGAGCACAGGTATAGCGTGGACTTACTCCCTTTTGTGCAGAAGGCCCCCAAAGACA 540
M       TATTTGAGGACAGGTACAGCATCAACTTGGAGCCTTTTGTGCAGAAGGTCCCCACGGCCA
        ---------+---------+---------+---------+---------+---------+

H         F  E  H  R  Y  S  V  D  L  L  P  F  V  Q  K  [A] P  K  D  S$^{CX}$ 96
M         F  E  D  R  Y  S  I  N  L  E  P  F  V  Q  K  [V] P  T  A  S$^{CX}$

H   541 GTGAAGCTGAGTCCAAGTACGATCCTCCTTTTGGGTTCCGGAAGTTCTCCAGTAAAGTCC 600
M       GTGAAGCTGAGCTCAAGTATGACCCGCCTTTTGGATTCCGGAAGTTCTCCAGTAAAGTCC
        ---------+---------+---------+---------+---------+---------+

H         E  A  E  S  K  Y  D  P  P  F  G  F  R  K  F  S$^{CP,C}$S  K  V  Q 116
M         E  A  E  L  K  Y  D  P  P  F  G  F  R  K  F  S$^{CP,C}$S  K  V  Q

H   601 AGACCCTCTTGGAACTCTTGCCAGAGCACGACCTCCCTGAACACTTGAAAGCCAAGACCT 660
M       AGAGCCTCTTGGATATGCTGCCCGAACATGACTTTCCTGAACACTTGAGAGCCAAGGCCT
        ---------+---------+---------+---------+---------+---------+

```
H    661 GTCGGCGCTGTGTGGTTATTGGAAGCGGAGGAATACTGCACGGATTAGAACTGGGCCACA 720
M        GCAAGCGCTGTGTGGTTGTTGGGAACGGGGGCATCCTGCACGGACTAGAGCTGGGTCACG
         ---------+---------+---------+---------+---------+---------+
H          R  R  C  V  V  I  G  S* G  G  I  L  H  G  L  E  L  G  H  T  156
M          K  R  C  V  V  V  G  N  G  G  I  L  H  G  L  E  L  G  H  A
                                    ↑2        STL
H    721 CCCTGAACCAGTTCGATGTTGTGATAAGGTTAAACAGTGCACCAGTTGAGGGATATTCAG 780
M        CCCTCAACCAGTTCGATGTGGTAATAAGGTTGAACAGTGCGCCAGTTGAGGGTTACTCTG
         ---------+---------+---------+---------+---------+---------+
H          L  N  Q  F  D  V  V  I  R  L  N  S  A  P  V  E  G  Y  S  E  176
M          L  N  Q  F  D  V  V  I  R  L  N  S  A  P  V  E  G [Y] S  E

H    781 AACATGTTGGAAATAAAACTACTATAAGGATGACTTATCCAGAGGGCGCACCACTGTCTG 840
M        AACACGTTGGGAATAAAACTACTATAAGGATGACTTACCCAGAGGGTGCGCCACTGTCGG
         ---------+---------+---------+---------+---------+---------+
H          H* V  G  N^G K  T  T^C I  R  M  T^CK Y  P  E  G  A  P  L  S^CK D  196
M          H* V  G  N^G K  T  T^C I  R  M  T^CK Y  P  E  G  A  P  L  S^CK D

H    841 ACCTTGAATATTATTCCAATGACTTATTTGTTGCTGTTTTATTTAAGAGTGTTGATTTCA 900
M        ACGTTGAATACTACGCCAATGATTTGTTCGTTACTGTTTTATTTAAGAGTGTTGATTTCA
         ---------+---------+---------+---------+---------+---------+
H          L  E  Y  Y  S  N  D  L  F  V  A  V  L  E  K  S  V  D  F  N  216
M          V  E  Y  Y  A  N  D  L  F  V  T  V  L [F  K] S  V  D  F  K
                                                ↑3

H    901 ACTGGCTTCAAGCAATGGTAAAAAAGGAAACCCTGCCATTCTGGGTACGACTCTTCTTTT 960
M        AGTGGCTTCAAGCAATGGTAAAAAATGAAAGCCTGCCCTTTTGGGTTCGCCTCTTCTTTT
         ---------+---------+---------+---------+---------+---------+
H          W  L  Q  A  M  V  K  K  E  T^CP L  P  F  W  V  R  L  F  F  W  236
M          W  L  Q  A  M  V  K  N^G E  S  L  P  F  W  V  R  L  F  F  W

H    961 GGAAGCAGGTGGCAGAAAAAATCCCACTGCAGCCAAAACATTTCAGGATTTTGAATCCAG 1020
M        GGAAGCAAGTGGCAGAAAAAGTCCCACTCCAGCCAAAGCACTTCAGGATTTTGAACCCAG
         ---------+---------+---------+---------+---------+---------+
H          K  Q  V  A  E  K  I  P  L  Q  P  K  H  F  R  I  L  N  P  V  256
M          K  Q  V  A  E  K  V  P  L  Q  P  K  H  F  R  I  L  N  P  V
                                                        ST3

H   1021 TTATCATCAAAGAGACTGCCTTTGACATCCTTCAGTACTCAGAGCCTCAGTCAAGGTTCT 1080
M        TTATCATCAAAGAAACTGCCTTCGACATCCTTCAGTACTCAGAGCCTCAGTCAAGATTCT
         ---------+---------+---------+---------+---------+---------+
H          I  I  K  E  T^CK A  F  D  I  L  Q  Y  S  E  P  Q  S  R  F  W  276
M          I  I  K  E  T^CK A  F  D  I  L  Q  Y  S  E  P  Q  S  R  F  W
                       ↑4

H   1081 GGGGCCGAGATAAGAACGTCCCCACAATCGGTGTCATTGCCGTTGTCTTAGCCACACATC 1140
M        GGGGCCATGATAAGAACATCCCCACGATCGGCGTCATTGCCGTTGTCTTGGCTACACATC
         ---------+---------+---------+---------+---------+---------+
H          G  R  D  K  N  V  P  T  I  G  V  I  A  V  V  L  A  T  H  L  296
M          G  H  D  K  N  I  P  T  I  G  V  I  A  V  V  L  A  T  H  L

H   1141 TGTGCGATGAAGTCAGTTTGGCGGGTTTTGGATATGACCTCAATCAACCCAGAACACCTT 1200
M        TGTGTGATGAAGTCAGCCTGGCAGGCTTTGGCTACGACCTCAGTCAACCCAGGACCCCTC
         ---------+---------+---------+---------+---------+---------+
H          C  D  E  V  S  L  A  G  F  G  Y  D  L  N  Q  P  R  T  P  L  316
M          C  D  E  V  S  L  A  G  F  G  Y  D  L  S  Q  P  R  T  P  L
                        STS

H   1201 TGCACTACTTCGACAGTCAATGCATGGCTGCTATGAACTTTCAGACCATGCATAATGTGA 1260
M        TGCACTACTTTGACAGTCAGTGCATGGGCGCCATGCACTGGCAGGTCATGCACAATGTGA
         ---------+---------+---------+---------+---------+---------+
H          H  Y  F  D  S  Q  C  M  A  A  M  N  F  Q  T  M  H  N^G V  T  336
M          H  Y  F  D  S  Q  C  M  G  A  M  H  W  Q  V  M  H  N^G V  T
                STP

H   1261 CAACGGAAACCAAGTTCCTCTTAAAGCTGGTCAAAGAGGGAGTGGTGAAAGATCTCAGTG 1320
M        CCACAGAGACCAAGTTCCTCCTGAAGCTCCTCAAGGAGGGCGTGGTGGAGGACCTCAGCG
         ---------+---------+---------+---------+---------+---------+
```

H  1321 GAGGCATTGATCGTGAATTTtgaacacagaaaacctcagttgaaaatgcaactctaactc 1380
M       GCGGCATCCACTgagaactcggaacacggcaaacctcacccagcaccgcagctgagagcg
        ----------+---------+---------+---------+---------+---------+
H         G  I  D  R  E  F  Stop                                    362
M         G  I  H     Stop
        359

H  1381 tgagagctgttttgacagccttcttgatttatttctccatcctgcagatactttgaagt 1440
M       tggtgagcagcctccacagggacttcaccctgcagctgcttcgatgtgcagctagtgttt
        ----------+---------+---------+---------+---------+---------+
H       gcagctcatgttttaacttttaatttaaaaacacaaaaaaaatttttagctcttcccact
M       tcaaactccacatttttttaaaaaaggaaaagaaagaacaacagcaacaacaaaaagctc
   1441 ----------+---------+---------+---------+---------+---------+ 1500
H       tttttttccctatttatttgaggtcagtgtttgtttttgcacaccatttttgtaaatgaaa
M       tgctctgtgcacctcttcgtcctatttatttgaagtcagtgttggattttgcacagtttt
   1501 ----------+---------+---------+---------+---------+---------+ 1560
H       cttaagaattgaattggaaagacttctcaaagagaattgtatgtaacgatgttgtattga
M       gtaagttaatcttaagaatgggattggaaggacttttcaaagagaattgtatagtttatt
   1561 ----------+---------+---------+---------+---------+---------+ 1620
H       tttttaagaaagtaatttaatttgtaaaacttctgctcgtttacactgcacattgaatac
M       gtttttaaggaagtaatttaatttgcagaaactgtacacacgtactctgctcaggtgttg
   1621 ----------+---------+---------+---------+---------+---------+ 1680
H       aggtaactaattggaaggagaggggaggtcactcttttgatggtggccctgaacctcatt
M       agtggaggagagggcttctggccctggatgatggctgtgatgcccgatactggggtctgc
   1681 ----------+---------+---------+---------+---------+---------+ 1740
H       ctggttccctgctgcgctgcttggtgtgacccacggaggatccactcccaggatgacgtg
M       tgctctgtttggtagaactgatggcagagaaacttcctgcctccaggataaagggcttac
   1741 ----------+---------+---------+---------+---------+---------+ 1800
H       ctccgtagctctgctgctgatactgggtctgcgatgcagcggcgtaggctggctggttga
M       tcatcacctctggcagctgctagacaagttcataaccccttctgctagtccatctgcca
   1801 ----------+---------+---------+---------+---------+---------+ 1860
H       gaaggtcacaacccttctctgttggtctgccttctgctgaaagactcgagaaccaaccag
M       gctggctcgcaggactcaggcagggcagctgtcccggaggctgctggttggtgagccact
   1861 ----------+---------+---------+---------+---------+---------+ 1920
H       ggaagctgtcctgaaggtccctggtcggagagggacatagaatctgtgacctctgacaac
M       gtcagctgagcgccgtgatgttgccccagggtggaagaagccacacttcctacactgtca
   1921 ----------+---------+---------+---------+---------+---------+ 1980
H       tgtgaagccaccctgggctacagaaaccacagtcttcccagcaattattacaattcttga
M       gggcacttttaaacttctggagggtgtgtgtgtgtgtgtgtgtgtgtgtgtgtgtgtgt
   1981 ----------+---------+---------+---------+---------+---------+ 2040
H       attccttgggatttttttactgccctttcaaagcacttaagtgttagatctaacgtgttc
M       gtgtgtgtgtgtgtgtgttcattctgccccttccaaatcatctaagtgttatttaaggca
   2041 ----------+---------+---------+---------+---------+---------+ 2100
H       cagtgtctgtctgaggtgacttaaaaaatcagaacaaaacttctattatccagagtcatg
M       ctctgctgtttgtatgagatggttcatagaaattatgacaaagcctttgttatccaggcc
   2101 ----------+---------+---------+---------+---------+---------+ 2160
H       ggagagtacacccttccaggaataatgttttgggaaacactgaaatgaaatcttcccag
M       atgggaaaagggaaaaagaaaagaaagaaagaaaagaataaaagcttttgaggagcccctg
   2161 ----------+---------+---------+---------+---------+---------+ 2220
H       tattataaattgtgtatttaaaaaaaagaaacttttctgaatgcctacctggcggtgtat
M       ttaaaaaaaaaaaaaaa - 2235
H       accaggcagtgtcccagtttaaaaagatgaaaaagaataaaacttttgaggaaaaaaaa
H       aaaaaa - 2288
```

FIG. 1C

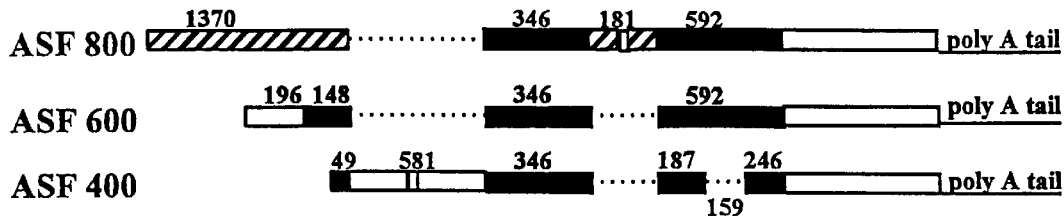

```
ASF_800   GTGGCACGATCTCGGCTCACTGCAAGCTCTGCCTCCCGGGTTCACACCATTCTCCTGCCTCAGCCTCCCGAGTAGCTGG
              10        20        30        40        50        60        70

ASF_800   GACTACAGGTGCCCACCACCACGTGCCCGGCTAATTTTTGTATTTTTAGTAGAGACGAGTTTCACCGTATTAGCCAGGA
              80        90       100       110       120       130       140       150

ASF_800   TGGTCATGTTTTGTTCTTGTTTTGTTTTAGAGACAGGGTCTCCCTCTGTCACCCAGGCTGGAGTGCAGTGGCACAAT
             160       170       180       190       200       210       220       230

ASF_800   CACAGCTCACTACAGTGTCAACCTTCCAGGTTGAGGATCACTCGATACTCATGCCTCAgCCTCCCATGTAGCTGGGGCC
             240       250       260       270       280       290       300       310

ASF_800   ACAGGGGCACACCACCACTCCTGACCCATTTTTTAAAAAATTTTTTGTATAGGTGGGGTCTCACCATGTTGcCCAgGCT
             320       330       340       350       360       370       380       390

ASF_800   AGCCTCCAACTcCTGGGCTCAAGCAACCCTCTcACCTTGGCCTCTCAAAGTGCTGAGATTATAGGTGTGACCCGCCATG
             400       410       420       430       440       450       460       470

ASF_800   CCCGCCTTTCCTCTGAGTTTTGTTGCATTCACGCAGCTCCTGGCTGAGGCAAAACATTAAAATGCATATGGAAATGCAG
             480       490       500       510       520       530       540       550

ASF_800   GCTGGGAAAATGCTTTGAAACCAATGCAATTTCTGTGTTAAGGGGACATTCCCTGATTCTTTCAGGTAATTTGCATTCT
             560       570       580       590       600       610       620       630

ASF_800   AGACTGTGACATTCTGTATCTCAACTGATAAATAAGCCTGTTTGTCATCCTGCTAGATGAGAACCTGATATATGAAACC
             640       650       660       670       680       690       700       710

ASF_800   TTTTTTTTAATCGTGGTTAAAAAAAACATAAAATTTACCATCATAATTATTTTTAAATGTACCATTTGGCAGCATTAAG
             720       730       740       750       760       770       780       790

ASF_800   TATATTTAAACTCTTGTGAAACAAATTTCTAGAATGTTTTCATCTTGCAAAACCGAAACGCTGTaCCTATTAAACAACT
             800       810       820       830       840       850       860

ASF_800   cCCCTTTTCTcCCTCTCTTCAACCCTGGTaACCATGTTTTTATGAATTTGaCTACTTTAGATaCCTCATATAAGtCAGg
             870       880       890       900       910       920       930       940

ASF_800   tCATacAgtATTTGtCTCTTTGTGaCTGGCTTcACTTAGcATAATGtCCTCAAAGTTtAaCTATGTtGtAGcATGTatC
ASF_600   ................................................................................G
             950       960       970       980       990      1000      1010      1020

ASF_800   AGAATTTTATGAAACATGAAGTCTTAGACACCCCGAAGTACATTTTCACCCCAAATGTATTTGAACAGTGTTAGGCTGG
ASF_600   GCGGCCGGCCGGCGCCCCCTCATTAGTATGCGGACGAAGGCGGCGGGCTGCGCGGAGCGGCGTCCCCTGCAGCCGCGGA
             1030      1040      1050      1060      1070      1080      1090      1100

ASF_800   GGGTGGGAGGCGGGAGTCCTTCTTGCTTTGCCTGTGCAATGAAATGAATACCCTGCTGTGTTTATCTCCTTGtCATGTG
ASF_600   CCGAGGCAGCGGCGGCCACCTGCCGGCCGAGCAATGCCAAGTGAGTACACCTATGTGAAACTGAGAAGTGATTGCTCGAG
             1110      1120      1130      1140      1150      1160      1170      1180

ASF_800   ATTCTcCCAGGTTGtTTCTTCAAGTTTCTGAGCCAAACTTAACTCTAAAAAGCAAATATTCTGTGTTAAAAGACAGTAA
ASF_600   GCCTTCCCTGCAATGGTACACCCGAGCTCAAAGCAAGATGAGAAGGCCCAGCTTGTTATTAAAAGACATCCTCAAATGT
             1190      1200      1210      1220      1230      1240      1250      1260
```

FIG. 2A

```
ASF_800    TCAACACGGGAGCTACATCAGACATCATAGGACAAATTGtCATCTAGAAGAGTATATTTTTAATGCAGGAGAGTTTTTA
ASF_600    ACATTGCTTGTGTTTGGAGTGTGGATCCTTTATATCCTCAAGTTAAATTATACTACTGAAGAATGTGACATGAAAAAAA
ASF_400    .............................................GAAGAATGTGACATGAAAAAAA
                1270      1280      1290      1300      1310      1320      1330      1340

ASF_800    AAACCCAGATTGGTGTGATTTCATTCC..................................................
ASF_600    TGCATTATGTGGACCCTGACCGTGTAA..................................................
                1350      1360      1370      1380      1390      1400      1410      1420

ASF_400    TGCATTATGTGGACCCTGACCATGTAAAGACCTACACCGTGCCTTTAAAGGAAGCAGGGCCCTcCCTGCTGAAGCATTC
                1350      1360      1370      1380      1390      1400      1410      1420

ASF_400    AGTGAGCCCAGGCACCAGCATCTTCAAACCGAGTCTTTTcTCTCCTTAgTGCTGCTCCCCGCTTTCCAGGCCTTCcTGG
                1430      1440      1450      1460      1470      1480      1490      1500

ASF_400    GATATCTTAGAgCTCCTGAAGGTGCGGCACTCGCCTTGAGGCACTTTCTTCTGAGCTGTGAGCTATGGGCAAGCAGTGG
                1510      1520      1530      1540      1550      1560      1570      1580

ASF_400    AGGGGGAAGAGAGCAGCTGAAGCAgATGCCGGTTCAACTTACTTAAAGATGTGGGACAAGCTCTGAGGAAGCCCCCAAG
                1590      1600      1610      1620      1630      1640      1650

ASF_400    ACAATGATGTCTGGTTGTGCACCATTGAAGCAAGAACAGAAACCATCCCAGAgTGGAGGACATGGcCCATGTGGTCCTc
           1660      1670      1680      1690      1700      1710      1720      1730

ASF_400    CTGTTCTGAGTGGCTATGAGATGGAGTTCTGTGTGAGCTCTCTACAGAAAAAGCCCTGTCTCCAGGCAATCAGTGGAGA
                1740      1750      1760      1770      1780      1790      1800      1810

ASF_400    TCTGTTAAACGAGTTGAAACAAAAGAGGACAAGGAATTGCTGTGGCTTTAGACGTTGCCAGGACATGTAGAAACTCACT
           1820      1830      1840      1850      1860      1870      1880      1890

ASF_800    ..............................................AGAGAGCTCAGAAATATGCTCAgC
ASF_600    ..............................................AGAGAGCTCAGAAATATGCTCAgC
ASF_400    CAGGATTTACTACTGCATCCACTGTCACTTAGGCGCAGGAGGGGTCACAGTCAGAAGAGAGCTCAGAAATATGCTCAGC
                1900      1910      1920      1930      1940      1950      1960      1970

ASF_800    AAGtCTTGCAGAAGGAATGtCGtCCcAAGTTTGCCAAGACATCAATGGCgCTGTtATTTGAgCACAGgtATAGCGTGGa
ASF_600    AAGTCTTGCAGAAGGAATGTCGTCCCAAGTTTGCcAAGACATCAATGGCGCTGTTATTTGAGCACAgGTATAGCGTGGA
ASF_400    AAGTCTTGCAGAAGGAATGTCGTCCCAAGTTTGCCAAGACATCAATGGCGCTGTTATTTGAGCACAGGTATAGCGTGGA
                1980      1990      2000      2010      2020      2030      2040      2050

ASF_800    CTTaCTcCCtTTTTGTgCAgAAGGcCCCCaAAGaCAgTGAAgCTGAgTCcAAgTaCGAtCCTCcTTTTGGGtTCCGGAAG
ASF_600    CTTACTCCcTTTTGTGCAgAAGGCCCCCaAAAGACAGTGAAGCTgAgTcCAAGTACGATCcTcCTTTTGGGTTCCgGAAG
ASF_400    CTTACTCCCTTTTGTGCAGAAGGCCCCCAAAGACAGTGAAGCTGAGTCCAAGTACGATCCTCCTTTTGGGTTCCGGAAG
                2060      2070      2080      2090      2100      2110      2120      2130

ASF_800    TtCTCcAGTaAAGTCcGGACCCTCTTGGAACTCTTGCCAGAGCACGACCTCCCTGAACACTTGAAAGCCAAGACCTGTC
ASF_600    TTCTCcAgTAAAGTcCAGACCCtCtTGgAACTCTTGccagagcacgacctccctgaacacttgAAAGCCAAGACCTGTC
ASF_400    TTCTCCAGTAAAGTCCAGACCCTCTTGGAACTCTTGCcAGAGCACGACCTcCCTGAACACTTGAAAGCCAAGACCTGTC
                2140      2150      2160      2170      2180      2190      2200      2210

ASF_800    GGCGCTGTGTGGTTATTGGAAGCGGAGGAATACTGCACGGATTAGAACTGGGCCACACCCTGAACCAGTTCGATGTTGT
ASF_600    GGCGCTGTGTGGTTATTGGAAGCGGAGGAATACTGCACGGATTAGAACTGGGCCACACCCTGAACCAGTTCGATGTTGT
ASF_400    GGCGCTGTGTGGtTATTGGAAGCGGAGGAATACTGCACGGaTTAGAACTGGGCCACACCCTGAACCAGTTCGATGTTGT
                2220      2230      2240      2250      2260      2270      2280      2290

ASF_800    GATAAGAACTCAGTGCACTGCTCTTGGTCAGTGTGGCTCCAGGAACAGTGAGGGACACAGGAAGCTCTTCACAGTCCCT
ASF_600    GATAAG..........................................................................
ASF_400    GATAAG..........................................................................
                2300      2310      2320      2330      2340      2350      2360      2370

ASF_800    GCCCACAAGGGACTTAACGTTTGAGAAGTTGAAACAAAAACACAAAATGGTTGGATGCTCCAAACTGTCATACTGACCC
                2380      2390      2400      2410      2420      2430      2440

ASF_800    TAAGTTGGAGGAGCATGCTGCTGGCTACAGTTAAACAGTGCACCAGTTGAGGGATATTCAGAACATGTTGGAAATAAAA
ASF_600    ...........................GTTAAACAGTGCACCAGTTGAGGGATATTCAGAACATGTTGGAAATAAAA
ASF_400    ...........................GtTAAACAGTGCaCCAgTTGAgGGATaTTCAGAACATGTTGGAAaTAAAa
           2450      2460      2470      2480      2490      2500      2510      2520
```

FIG. 2B

```
ASF_800  CTACTATAAGGATGACTTATCCAGAGGGCGCACCACTGTCTGACCTTGAATATTATTCCAATGACTTATTTGTTGCTGT
ASF_600  CTACTATAAGGATGACTTATCCAGAGGGCGCACCACTGTCTGACCTTGAATATTATTCCAATGACTTATTTGTTGCTGT
ASF_400  CTaCTATAaGGATgACTTATcCAGAGGgCgCACCAcTGTCTGACCTTGAATATTATTCCAATGACTTATTTGTTGCTGT
         2530      2540      2550      2560      2570      2580      2590      2600

ASF_800  TTTATTTAAGAGTGTTGATTTCAACTGGCTTCAAGCAATGGTAAAAAAGGAAACCCtGCCATTCTGGGTACGACTCTTC
ASF_600  TTTATTTAAGAGTGTTGATTTCAACTGGCTTCAAGCAATGGTAAAAAAGGAAACCCTGCCATTCTGGGTACGACTCTTC
ASF_400  TTTATTTAAGAGTGTTGATTTCAACTGGCTTCAAGCAATGGTAAAAAAGGAAACCCTG.....................
         2610      2620      2630      2640      2650      2660      2670      2680

ASF_800  TTTTGGAAGCAGGTGGCAGAAAAAATCCCACTGCAGCCAAAACATTTCAGGATTTTGAATCCAGTTATCATCAAAGAGA
ASF_600  TTTTGGAAGCAGGTGGCAGAAAAAATCCCACTGCAGCCAAAACATTTCAGGATTTTGAATCCAGTTATCATCAAAGAGA
         2690      2700      2710      2720      2730      2740      2750      2760

ASF_800  CTGCCTTTGACATCCTTCAGTACTCAGAGCCTCAGTCAAGGTTCTGGGGCCGAGATAAGAACGTCCCCACAATCGGTGT
ASF_600  CTGCCTTTGACATCCTTCAGTACTCAGAGCCTCAGTCAAGGTTCTGGGGCCGAGATAAGAACGTCCCCACAATCGGTGT
ASF_400  .........................................................AACGTCCCCACAATCGGTGT
         2770      2780      2790      2800      2810      2820      2830      2840

ASF_800  CATTGCCGTTGTCTTAGCCACACATCTGTGCGATGAAGTCAGTTTGGCGGGTTTTGGATATGACCTCAATCAACCCAGA
ASF_600  CATTGCCGTTGTCTTAGCCACACATCTGTGCGATGAAGTCAGTTTGGCGGGTTTTGGATATGACCTCAATCAACCCAGA
ASF_400  CATTGCCGTTGTCTTAGCCACACATCTGTGCGATGAAGTCAGTTTGGCGGGTTTTGGATATGACCTCAATCAACCCAGA
         2850      2860      2870      2880      2890      2900      2910      2920

ASF_800  ACACCtTTGCACTACTTCGACAGTCAATGCATGGCTGCTATGAACTTTCAGACCATGCATAATGTGACAACGGAAACCA
ASF_600  ACACCTTTGCACTACTTCGACAGTCAATGCATGGCTGCTATGAACTTTCAGACCATGCATAATGTGACAACGGAAACCA
ASF_400  ACACCTTTGCACTACTTCGACAGTCAATGCATGGCTGCTATGAACTTTCAGACCATGCATAATGTGACAACGGAAACCA
         2930      2940      2950      2960      2970      2980      2990      3000

ASF_800  AGTTCCTCTTAAAGCTGGTCAAAGAGGGAGTGGTGAAAGATCTCAGTGGAGGCATTGATCGtgaatttgaacacagaa
ASF_600  AGTTCCTCTTAAAGCTGGTCAAAGAGGGAGTGGTGAAAGATCTCAGTGGAGGCATTGATCGtgaatttgaacacagaa
ASF_400  AGTTCCTCTTAAaGCTGGTCAAAGAGGGAGTGGTGAAAGATCTCAGTGGAGGCATTGATCGtgaatttgaacacagaa
         3010      3020      3030      3040      3050      3060      3070      3080

ASF_800  aacctcagttgaaaatgcaactctaactctgagagctgtttttgacagccttcttgatttatttctccatcctgcagat
ASF_600  aacctcagttgaaaatgcaactctaactctgagagctgtttttgacagccttcttgatttatttctccatcctgcagat
ASF_400  aacctcagttgaaaatgcaactctaactctgagagctgtttttgacagccttcttgatttatttctccatcctgcagat
         3090      3100      3110      3120      3130      3140      3150      3160

ASF_800  actttgaagtgcagctcatgttttaacttttaatttaaaaacacaaaaaaaatttagctcttcccacTTTTTTTTTC
ASF_600  actttgaagtgcagctcatgttttaacttttaatttaaaaacacaaaaaaaatttagctcttcccacTTTTTTTTTC
ASF_400  actttgaagtgcagctcatgttttaacttttaatttaaaaacacaaaaaaaatttagctcttcccacTTTTTTTTTC
         3170      3180      3190      3200      3210      3220      3230

ASF_800  CTATTTATTTGAGGTCAGTGTTTGTTTTTGCACACCATTTTGTAAATGAAACTTAAGAATTGAATTGGAAAGACTTCTC
ASF_600  CTATTTATTTGAGGTCAGTGTTTGTTTTTGCACACCATTTTGTAAATGAAACTTAAGAATTGAATTGGAAAGACTTCTC
ASF_400  CTATTTATTTGAGGTCAGTGTTTGTTTTTGCACACCATTTTGTAAATGAAACTTAAGAATTGAATTGGAAAGACTTCTC
         3240      3250      3260      3270      3280      3290      3300      3310

ASF_800  AAAGAGAATTGTATGTAACGATGTTGTATTGATTTTTAAGAAAGTAATTTAATTTGTAAAACTTCTGCTCGTTTACACT
ASF_600  AAAGAGAATTGTATGTAACGATGTTGTATTGATTTTTAAGAAAGTAATTTAATTTGTAAAACTTCTGCTCGTTTACACT
ASF_400  AAAGAGAATTGTATGTAACGATGTTGTATTGATTTTTAAGAAAGTAATTTAATTTGTAAAACTTCTGCTCGTTTACACT
         3320      3330      3340      3350      3360      3370      3380      3390

ASF_800  GCACATTGAATACAGGTAACTAATTGGAAGGAGAGGGGAGGTCACTCTTTTGATGGTGGCCCTGAACCTCATTCTGGTT
ASF_600  GCACATTGAATACAGGTAACTAATTGGAAGGAGAGGGGAGGTCACTCTTTTGATGGTGGCCCTGAACCTCATTCTGGTT
ASF_400  GCACATTGAATACAGGTAACTAATTGGAAGGAGAGGGGAGGTCACTCTTTTGATGGTGGCCCTGAACCTCATTCTGGTT
         3400      3410      3420      3430      3440      3450      3460      3470

ASF_800  CCCTGCTGCGCTGCTTGGTGTGACCCACGGAGGATCCACTCCCAGGATGACGTGCTCCGtAGCTCTGCTGCTGATACTG
ASF_600  CCCTGCTGCGCTGCTTGGTGTGACCCACGGAGGATCCACTCCCAGGATGACGTGCTCCGtAGCTCTGCTGCTGATACTG
ASF_400  CCCTGCTGCGCTGCTTGGTGTGACCCACGGAGGATCCACTCCCAGGATGACGTGCTCCGtAGCTCTGCTGCTGATACTG
         3480      3490      3500      3510      3520      3530      3540      3550

ASF_800  GGTCTGCGATGCAGCGGCGTAGGCTGGCTGGTTGAgAAGGTCACAACCCTTCTCTGTTGGTCTGCCTTCTGCTGAAAGA
ASF_600  GGTCTGCGATGCAGCGGCGTAGGCTGGCTGGTTGAgAAGGTCACAACCCTTCTCTGTTGGTCTGCCTTCTGCTGAAAGA
ASF_400  GGTCTGCGATGCAGCGGCGTAGGCTGGCTGGTTGAgAAGGTCACAACCCTTCTCTGTTGGTCTGCCTTCTGCTGAAAGA
```

FIG. 2C

|          | 3560       | 3570       | 3580       | 3590       | 3600       | 3610       | 3620       | 3630       |
|----------|------------|------------|------------|------------|------------|------------|------------|------------|
| ASF_800  | CTCGAGAACCAACCAGGGAAGCTGTCCTGAAGGTCCCTGGTCGGAGAGGGACATAGAATCTGTGACCTCTGACAACTGT |
| ASF_600  | CTCGAGAACCAACCAGGGAAGCTGTCCTGAAGGTCCCTGGTCGGAGAGGGACATAGAATCTGTGACCTCTGACAACTGT |
| ASF_400  | CTCGAGAACCAACCAGGGAAGCTGTCCTGAAGGTCCCTGGTCGGAGAGGGACATAGAATCTGTGACCTCTGACAACTGT |
|          | 3640       | 3650       | 3660       | 3670       | 3680       | 3690       | 3700       | 3710       |
| ASF_800  | GAAGCCACCCTGGGCTACAGAAACCACAGTCTTCCCAGCAATTATTACAATTCTTGAATTCCTTGGGGATTTTTTACTG |
| ASF_600  | GAAGCCACCCTGGGCTACAGAAACCACAGTCTTCCCAGCAATTATTACAATTCTTGAATTCCTTGGGGATTTTTTACTG |
| ASF_400  | GAAGCCACCCTGGGCTACAGAAACCACAGTCTTCCCAGCAATTATTACAATTCTTGAATTCCTTGGGGATTTTTTACTG |
|          | 3720       | 3730       | 3740       | 3750       | 3760       | 3770       | 3780       | 3790       |
| ASF_800  | CCCTTTCAAAGCACTTAAGTGTTAGATCTAACGTGTTCCAGTGTCTGTCTGAGGTGACTTAAAAAATCAGAACAAAACT |
| ASF_600  | CCCTTTCAAAGCACTTAAGTGTTAGATCTAACGTGTTCCAGTGTCTGTCTGAGGTGACTTAAAAAATCAGAACAAAACT |
| ASF_400  | CCCTTTCAAAGCACTTAAGTGTTAGATCTAACGTGTTCCAGTGTCTGTCTGAGGTGACTTAAAAAATCAGAACAAAACT |
|          | 3800       | 3810       | 3820       | 3830       | 3840       | 3850       | 3860       | 3870       |
| ASF_800  | TCTATTATCCAGAGTCATGGGAGAGTACACCCTTTCCAGGAATAATGTTTTGGGAAACACTGAAATGAAATCTTCCCAG |
| ASF_600  | TCTATTATCCAGAGTCATGGGAGAGTACACCCTTTCCAGGAATAATGTTTTGGGAAACACTGAAATGAAATCTTCCCAG |
| ASF_400  | TCTATTATCCAGAGTCATGGGAGAGTACACCCTTTCCAGGAATAATGTTTTGGGAAACACTGAAATGAAATCTTCCCAG |
|          | 3880       | 3890       | 3900       | 3910       | 3920       | 3930       | 3940       | 3950       |
| ASF_800  | TATTATAAATTGTGTATTTAAAAAAAAGAAACTTTTCTGAATGCCTACCTGGCGGTGTATACCAGGCAGTGTCCCAGTT |
| ASF_600  | TATTATAAATTGTGTATTTAAAAAAAAGAAACTTTTCTGAATGCCTACCTGGCGGTGTATACCAGGCAGTGTCCCAGTT |
| ASF_400  | TATTATAAATTGTGTATTTAAAAAAAAGAAACTTTTCTGAATGCCTACCTGGCGGTGTATACCAGGCAGTGTCCCAGTT |
|          | 3960       | 3970       | 3980       | 3990       | 4000       | 4010       | 4020       |            |
| ASF_800  | TAAAAGATGAAAAAGAATAAAAACTTTTGAGG.AAAAAAAAAAAa------------------------------------ |
| ASF_600  | TAAAAGATGAAAAAGAATAAAAACTTTTGAGGAAAAAAAAAAAAAA--------------------------------- |
| ASF_400  | TAAAAGATGAAAAAGAATAAAAACTTTTGAGGAAAAAAAAAAAAAA--------------------------------- |
|          | 4030       | 4040       | 4050       | 4060       | 4070       | 4080       | 4090       | 4100       |

FIG. 2D

Human 4ST3Gal VI Full length

```
        CTGGCGGGAGCCTGAGACTCCGGGCAGGGCTGCTCCCTCCTCTGCTCCCCCGCCAGATCC
    1   ------------+---------+---------+---------+---------+---------+  60
        GACCGCCCTCGGACTCTGAGGCCCGTCCCGACGAGGGAGGAGACGAGGGGGCGGTCTAGG

GCGGGGAAGGAATCGTGCCCGCGCCGCCCCTGGCCCGCGCCACCTTCCTTTGGTTTCTGC
   61   ------------+---------+---------+---------+---------+---------+ 120
        CGCCCCTTCCTTAGCACGGGCGCGGCGGGGACCGGGCGCGGTGGAAGGAAACCAAAGACG

CGGCCTCGGGCTTCTGCGGCCCGATGTGGCAGGCGCCGCGAGAGAGGCAGCAGCCGGCTG
  121   ------------+---------+---------+---------+---------+---------+ 180
        GCCGGAGCCCGAAGACGCCGGGCTACACCGTCCGCGGCGCTCTCTCCGTCGTCGGCCGAC

M  W  Q  A  P  R  E  R  Q  Q  P  A  G  -

GAGCAGCGGCCCCTCAGGTCTCGGAGCCCGGTGCGCCTCTGCGGTCGTCGCTCCTGGGCC
  181   ------------+---------+---------+---------+---------+---------+ 240
        CTCGTCGCCGGGGAGTCCAGAGCCTCGGGCCACGCGGAGACGCCAGCAGCGAGGACCCGG

A  A  A  P  Q  V  S  E  P  G  A  P  L  R  S  S  L  L  G  L  -

TCGGCGGGTCACTCTTGCCGGCCGGCTTCGCTGCGGGTTTGCACTGCCCGGGTGAGCCAG
  241   ------------+---------+---------+---------+---------+---------+ 300
        AGCCGCCCAGTGAGAACGGCCGGCCGAAGCGACGCCCAAACGTGACGGGCCCACTCGGTC

G  G  S  L  L  P  A  G  F  A  A  G  L  H  C  P  G  E  P  A  -

CCATGAGAGGGTATCTTGTGGCCATATTCCTGAGTGCTGTCTTCCTCTATTATGTACTGC
  301   ------------+---------+---------+---------+---------+---------+ 360
        GGTACTCTCCCATAGAACACCGGTATAAGGACTCACGACAGAAGGAGATAATACATGACG

M  R  G  Y  L  V  A  I  F  L  S  A  V  F  L  Y  Y  V  L  H 20
            1
        ATTGCATATTATGGGGAACGAATGTCTATTGGGTGGCACCTGTGGAAATGAAACGGAGAA
  361   ------------+---------+---------+---------+---------+---------+ 420
        TAACGTATAATACCCCTTGCTTACAGATAACCCACCGTGGACACCTTTACTTTGCCTCTT

C  I  L  W  G  T  N  V  Y  W  V  A  P  V  E  M  K  R  R  N 20

ATAAGATCCAGCCTTGTTTATCAAAGCCAGCTTTTGCCTCTCTGCTGAGGTTTCATCAGT
  421   ------------+---------+---------+---------+---------+---------+ 480
        TATTCTAGGTCGGAACAAATAGTTTCGGTCGAAAACGGAGAGACGACTCCAAAGTAGTCA

K  I  Q  P  C  L  S  K  P  A  F  A  S  L  L  R  F  H  Q  F 60

TTCACCCTTTTCTGTGTGCGGCTGATTTTAGAAAGATTGCTTCCTTGTATGGTAGCGATA
  481   ------------+---------+---------+---------+---------+---------+ 540
        AAGTGGGAAAAGACACACGCCGACTAAAATCTTTCTAACGAAGGAACATACCATCGCTAT

H  P  F  L  C  A  A  D  F  R  K  I  A  S  L  Y  G  S  D  K 80

AGTTTGATTTGCCCTATGGGATGAGAACATCAGCGGAATATTTTCGACTTGCTCTTTCAA
  541   ------------+---------+---------+---------+---------+---------+ 600
        TCAAACTAAACGGGATACCCTACTCTTGTAGTCGCCTTATAAAAGCTGAACGAGAAAGTT
```

FIG. 3A

```
            F   D   L   P   Y   G   M   R   T   S   A   E   Y   F   R   L   A   L   S   K 100
       AACTGCAGAGTTGTGATCTCTTTGATGAGTTTGACAACATACCCTGTAAAAAGTGTGTGG
601    ---------+---------+---------+---------+---------+---------+ 660
       TTGACGTCTCAACACTAGAGAAACTACTCAAACTGTTGTATGGGACATTTTTCACACACC

L   Q   S   C   D   L   F   D   E   F   D   N   I   P   C   K   K   C   V   V 120
       TGGTTGGTAATGgAgGAGTTTTGAAGAATAAGACATTAGGAGAAAAAATCGACTCCTATG
661    ---------+---------+---------+---------+---------+---------+ 720
       ACCAACCATTACcTcCTCAAAACTTCTTATTCTGTAATCCTCTTTTTTAGCTGAGGATAC

V   G   N   G   G   V   L   K   N   K   T   L   G   E   K   I   D   S   Y   D 140
       ATGTAATAATAAGAATGAATAATGGTCCTGTTTTAGGACATGAAGAAGAAGTTGGGAGAA
721    ---------+---------+---------+---------+---------+---------+ 780
       TACATTATTATTCTTACTTATTACCAGGACAAAATCCTGTACTTCTTCTTCAACCCTCTT

V   I   I   R   M   N   N   G   P   V   L   G   H   E   E   E   V   G   R   R 160
       GGACAACCTTCCGACTTTTTTATCCAGAATCTGTTTTTTCAGATCCTATTCACAATGACC
781    ---------+---------+---------+---------+---------+---------+ 840
       CCTGTTGGAAGGCTGAAAAAATAGGTCTTAGACAAAAAAGTCTAGGATAAGTGTTACTGG

T   T   F   R   L   F   Y   P   E   S   V   F   S   D   P   I   H   N   D   P 180
       CTAATACGACAGTGATTCTCACTGCTTTTAAGCCACATGATTTAAGGTGGCTGTTGGAAT
841    ---------+---------+---------+---------+---------+---------+ 900
       GATTATGCTGTCACTAAGAGTGACGAAAATTCGGTGTACTAAATTCCACCGACAACCTTA

N   T   T   V   I   L   T   A   F   K   P   H   D   L   R   W   L   L   E   L 200
       TGTTGATGGGTGACAAAATAAACACTAATGGTTTTTGGAAGAAACCAGCCTTAAACCTGA
901    ---------+---------+---------+---------+---------+---------+ 960
       ACAACTACCCACTGTTTTATTTGTGATTACCAAAAACCTTCTTTGGTCGGAATTTGGACT

L   M   G   D   K   I   N   T   N   G   F   W   K   K   P   A   L   N   L   I 220
       TTTATAAACCTTATCAAATCCGAATATTAGATCCTTTCATTATCAGAACAGCAGCTTATG
961    ---------+---------+---------+---------+---------+---------+ 1020
       AAATATTTGGAATAGTTTAGGCTTATAATCTAGGAAAGTAATAGTCTTGTCGTCGAATAC

Y   K   P   Y   Q   I   R   I   L   D   P   F   I   I   R   T   A   A   Y   E 240
       AACTGCTTCATTTTCCAAAAGTGTTTCCCAAAAATCAGAAACCTAAACACCCAACAACAG
1021   ---------+---------+---------+---------+---------+---------+ 1080
       TTGACGAAGTAAAAGGTTTTCACAAAGGGTTTTTAGTCTTTGGATTTGTGGGTTGTTGTC

L   L   H   F   P   K   V   F   P   K   N   Q   K   P   K   H   P   T   T   G 260
       GAATTATTGCCATCACATTGGCGTTTTACATATGTCACGAAGTTCACCTAGCTGGTTTTA
1081   ---------+---------+---------+---------+---------+---------+ 1140
       CTTAATAACGGTAGTGTAACCGCAAAATGTATACAGTGCTTCAAGTGGATCGACCAAAAT

I   I   A   I   T   L   A   F   Y   I   C   H   E   V   H   L   A   G   F   K 280
       AATACAACTTTTCTGACCTCAAGAGTCCttTGCACTACTATgGGAATGCCACCATGTCTT
1141   ---------+---------+---------+---------+---------+---------+ 1200
       TTATGTTGAAAAGACTGGAGTTCTCAGGaaACGTGATGATAcCCTTACGGTGGTACAGAA
```

TGATGAATAAGAACGcGTATCACAATGTGACTGCAGAGCAGCTCTTTTTGAAGGACATTA
1201 ---------+---------+---------+---------+---------+---------+ 1260
     ACTACTTATTCTTGCgCATAGTGTTACACTGACGTCTCGTCGAGAAAAACTTCCTGTAAT

M   N   K   N   A   Y   H   N   V   T   A   E   Q   L   F   L   K   D   I   I 320

TAGAAAAAACCTcGTAATCAACTTGACTCAAGATTGACTCTACAGACTCAGAAGATGAT
1261 ---------+---------+---------+---------+---------+---------+ 1320
     ATCTTTTTTGGAgCATTAGTTGAACTGAGTTCTAACTGAGATGTCTGAGTCTTCTACTA

E   K   N   L   V   I   N   L   T   Q   D Stop                              331

GCTAACAGTGTTAGTTTTATTTTTGTACTGCAATTTTTAGTTTAAAATATGTTGgATGCA
1321 ---------+---------+---------+---------+---------+---------+ 1380
     CGATTGTCACAATCAAAATAAAAACATGACGTTAAAAATCAAATTTTATACAACcTACGT

CTCGTCAAATAATTATGTATACTGTCTGTTGCTGCTGGTGATTCATAACCACCAGcTTAA
1381 ---------+---------+---------+---------+---------+---------+ 1440
     GAGCAGTTTATTAATACATATGACAGACAACGACGACCACTAAGTATTGGTGGTCgAATT

TTTCTGTGAATACTGTATATTTAACTTATGAAAACCAAGAAATGTAAAGATAACAGGAAA
1441 ---------+---------+---------+---------+---------+---------+ 1500
     AAAGACACTTATGACATATAAATTGAATACTTTTGGTTCTTTACATTTCTATTGTCCTTT

ATAAGTTTTGATTGCAATGTTTTAAAAAAAAAAAAAAAAAAAAAAAAAAAAAAAA
1501 ---------+---------+---------+---------+---------+------ 1556
     TATTCAAAACTAACGTTACAAAATTTTTTTTTTTTTTTTTTTTTTTTTTTTTTTT
``` c

FIG. 3C

Mouse 4ST3Gal VI

```
      GGGGAACGTTGGCGGTCTCAGCCTCCGGGCCACACTGCGCCTCGCTCCGCTCTGCTCCTT
  1   ------------------------------------------------------------+  60
      CCCCTTGCAACCGCCAGAGTCGGAGGCCCGGTGTGACGCGGAGCGAGGCGAGACGAGGAA

CGCCACATCGGGGGTAGGGGTGGAGGGAAGGGAtcgcgttcttgtcaccccgctagctca
 61   ------------------------------------------------------------+ 120
      GCGGTGTAGCCCCCATCCCCACCTCCCTTCCCtagcgcaagaacagtggggcgatcgagt ggcttCcgCtcgccgactgcgtcgggacccgatgctgcagacgccacgggacagacagaa
121   ------------------------------------------------------------+ 180
      ccgaaGgcGagcggctgacgcagccctgggctacgacgtctgcggtgccctgtctgtcttgcgcgctgcggagagccctgtgcatgcctctgcggtggccgagctcgggcctcggcagca
181   ------------------------------------------------------------+ 240
      cgcgcgacgcctctcgggacacgtacggagacgccaccggctcgagcccggagccgtcgtcgcacacgtgaagcaacaacaaagCccctcatcttggattatttccagcatcaagacctc
241   ------------------------------------------------------------+ 300
      gcgtgtgcacttcgttgttgtttcGgggagtagaacctaataaaggtcgtagttctggagcacatgtCaacagcaggctcctgagGCAGTCCATCCTCCTCCAaCTCTCcTCActACATt
301   ------------------------------------------------------------+ 360
      gtgtacaGttgtcgtccgaggactcCGTCAGGTAGGAGGAGGTtGAGAGgAGTgaTGTAa- CTTCAGAAAgAgAGGGtCTTCAGGAACACaCCCCAAAAGcGCAGATTTATTTACTAATTC
361   ------------------------------------------------------------+ 420
      GAAGTCTTTcTcTCCCaGAAGTCCTTGTGtGGGGTTTTCgCGTCTAAATAAATGATTAAG- ATGtATTTGAACCATCGTGGAAGACCTCTGcATATTCATCTCCCCTCACTTTGGACTCTG
421   ------------------------------------------------------------+ 480
      TACaTAAACTTGGTAGCACCTTCTGGAGACgTATAAGTAGAGGGGAGTGAAACCTGAGAC- TTTCAGGCAGGCCAGCCATGAAAGGGtATCTGGTGgCCATATTCCTGAGTTCCATCTTCC
481   ------------------------------------------------------------+ 540
      AAAGTCCGTCCGGTCGGTACTTTCCCaTAGACCACcGGTATAAGGACTCAAGGTAGAAGG
```

```
c                M   K   G   Y   L   V   A   I   F   L   S   S   I   F   L  -
      TCTATTATGTACTATACTGTATACTGTGGGGAACAAATGGCTATTGGTTCCCAGCTGAAG
541   ------------------------------------------------------------+ 600
      AGATAATACATGATATGACATATGACACCCCTTGTTTACCGATAACCAAGGGTCGACTTC c            Y   Y   V   L   Y   C   I   L   W   G   T   N   G   Y   W   F   P   A   E   E  -
      AAATGAGGACTAGAAACAATGTCAATAATTGTTTTAAAAAGCCAGCTTTCGCCAATCTTC
601   ------------------------------------------------------------+ 660
      TTTACTCCTGATCTTTGTTACAGTTATTAACAAAATTTTTCGGTCGAAAGCGGTTAGAAG c            M   R   T   R   N   N   V   N   N   C   F   K   K   P   A   F   A   N   L   L  -
      TGAGATTTCCTCAGCTTTACCCATTTCTGTGCAGAGCTGACTTTATAAAGGTTGCTGCCA
661   ------------------------------------------------------------+ 720
      ACTCTAAAGGAGTCGAAATGGGTAAAGACACGTCTCGACTGAAATATTTCCAACGACGGT c            R   F   P   Q   L   Y   P   F   L   C   R   A   D   F   I   K   V   A   A   M  -
```

FIG. 4A

```
        TGTCCGGTACCAATAATTTTCCGTTGCCCTATGGAATAAAGACCTTCGAGACATATTTCA
    721 ---------+---------+---------+---------+---------+---------+ 780
        ACAGGCCATGGTTATTAAAAGGCAACGGGATACCTTATTTCTGGAAGCTCTGTATAAAGT c        S  G  T  N  N  F  P  L  P  Y  G  I  K  T  F  E  T  Y  F  S  -

GCTCGGCCCTTTCAAAaCTGCAGAGTTGTGATCTCTTTGACGAGTTTGACAGAGTGCCAT
    781 ---------+---------+---------+---------+---------+---------+ 840
        CGAGCCGGGAAAGTTTtGACGTCTCAACACTAGAGAAACTGCTCAAACTGTCTCACGGTA c        S  A  L  S  K  L  Q  S  C  D  L  F  D  E  F  D  R  V  P  C  -

GTAAAAGGTGTGTGGTGGTTGGTAATGGAGGAGTGTTGAAGAATAAGACATTAGGAGCAA
    841 ---------+---------+---------+---------+---------+---------+ 900
        CATTTTCCACACACCACCAACCATTACCTCCTCACAACTTCTTATTCTGTAATCCTCGTT c        K  R  C  V  V  G  N  G  G  V  L  K  N  K  T  L  G  A  T  -

CAATTGACTCCTATGATGTAATAATAAGAATGAACAACGGTCCTGTCTTAGGCCATGAAG
    901 ---------+---------+---------+---------+---------+---------+ 960
        GTTAACTGAGGATACTACATTATTATTCTTACTTGTTGCCAGGACAGAATCCGGTACTTC c        I  D  S  Y  D  V  I  I  R  M  N  N  G  P  V  L  G  H  E  E  -

AGGAAGTTGGGACAAGAACAACCTTCAGGCTTTTTTATCCAGAGTCTGTCTTTTCAGACt
    961 ---------+---------+---------+---------+---------+---------+ 1020
        TCCTTCAACCCTGTTCTTGTTGGAAGTCCGAAAAAATAGGTCTCAGACAGAAAAGTCTGa c        E  V  G  T  R  T  T  F  R  L  F  Y  P  E  S  V  F  S  D  S  -

CCAGTCACTATGACCCCAATACTACAGCGGTTCTCGTCGTCTTTAAGCCACAGGATTTAA
   1021 ---------+---------+---------+---------+---------+---------+ 1080
        GGTCAGTGATACTGGGGTTATGATGTCGCCAAGAGCAGCAGAAATTCGGTGTCCTAAATT c        S  H  Y  D  P  N  T  T  A  V  L  V  V  F  K  P  Q  D  L  R  -

GGTGGCTGGTGGAAATACTGCTAGGTAAAAAAATAAATACTCAAGGGTTTTGGAAGACAC
   1081 ---------+---------+---------+---------+---------+---------+ 1140
        CCACCGACCACCTTTATGACGATCCATTTTTTATTTATGAGTTCCCAAAACCTTCTGTG c        W  L  V  E  I  L  L  G  K  K  I  N  T  Q  G  F  W  K  T  P  -

CAGCCTTAAAACTGATCTATAAACAATACCAAATCAGAATATTAGATCCATATATCACCA
   1141 ---------+---------+---------+---------+---------+---------+ 1200
        GTCGGAATTTTGACTAGATATTTGTTATGGTTTAGTCTTATAATCTAGGTATATAGTGGT c        A  L  K  L  I  Y  K  Q  Y  Q  I  R  I  L  D  P  Y  I  T  S  -

GCGAAGCAGCTTTTcAAATGCTTCGTTTTCCCAGAGTATTTCCCAAGGATCAGAAACCCA
   1201 ---------+---------+---------+---------+---------+---------+ 1260
        CGCTTCGTCGAAAgTTTACGAAGCAAAAGGGTCTCATAAAGGGTTCCTAGTCTTTGGGT c        E  A  A  F  Q  M  L  R  F  P  R  V  F  P  K  D  Q  K  P  K  -

AACACCCTACAACAGGAATTATTGCCATCACAATGGCCTTTcACATATGCAGTGAAGTGC
   1261 ---------+---------+---------+---------+---------+---------+ 1320
        TTGTGGGATGTTGTCCTTAATAACGGTAGTGTTACCGGAAAgTGTATACGTCACTTCACG c        H  P  T  T  G  I  I  A  I  T  M  A  F  H  I  C  S  E  V  H  -
```

FIG. 4B

```
     ACCTCGCTGGTTTTAAGTACAACTTTTACAGCCCCAACAGTCCTTTACACTACTACGGGA
1321 ---------+---------+---------+---------+---------+---------+ 1380
     TGGAGCGACCAAAATTCATGTTGAAAATGTCGGGGTTGTCAGGAAATGTGATGATGCCCT c       L  A  G  F  K  Y  N  F  Y  S  P  N  S  P  L  H  Y  Y  G  N -

ATGCCACCATGTCTTTGATGAAGCAGAATGCATATCACAATCTGACTGCAGAGcagctct
1381 ---------+---------+---------+---------+---------+---------+ 1440
     TACGGTGGTACAGAAACTACTTCGTCTTACGTATAGTGTTAGACTGACGTCTCgtcgaga c       A  T  M  S  L  M  K  Q  N  A  Y  H  N  L  T  A  E  Q  L  F - ttttaaacgacattataaagaaaaaaatggtgatcaacttgacttaaaattgaccctatg
1441 ---------+---------+---------+---------+---------+---------+ 1500
     aaaatttgctgtaatatttcttttttaccactagttgaactgaattttaactgggatac c       L  N  D  I  I  K  K  K  M  V  I  N  L  T  *              - gATCCAAAAGATGATGATGCTAAACAGTATTAGTTTTATTTTTGTACTGCAAATTTTAGT
1501 ---------+---------+---------+---------+---------+---------+ 1560
     cTAGGTTTTCTACTACTACGATTTGTCATAATCAAAATAAAAACATGACGTTTAAAATCA -

TTATTTTTAAATATATTGGATGAACTTATCAAAAAAAAAAAAAAAAAAAAAAAAAAAAAA
1561 ---------+---------+---------+---------+---------+---------+ 1620
     AATAAAAATTTATATAACCTACTTGAATAGTTTTTTTTTTTTTTTTTTTTTTTTTTTTTT-

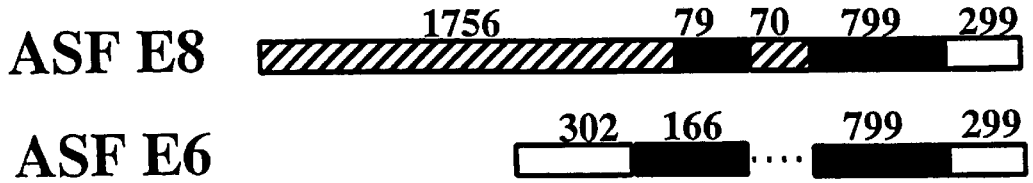

4ST3Gal VI cDNA for two ASF (E6 is coding for sialyltransferase) and E8, aligned

```
4ST3Gal_VI_E8_Human_FL   CATAATTATGCTAAAATAAATCACATAACTTCCTGTCTTAGACAAAG
                                  10        20        30        40

4ST3Gal_VI_E8_Human_FL   AGTCAGTATTTTTTGCCAGTGTTTCATAGTACATCTTAGATCATGTT
                              50        60        70        80        90

4ST3Gal_VI_E8_Human_FL   TCTAACTTGTGCTTACTTGATGAAAAAAAGCTGATGCTTCTGCATTT
                              100       110       120       130       140

4ST3Gal_VI_E8_Human_FL   GATTTCATTACTGGTTGATTGAAAAATAATTGTAATGCTTTTCATGG
                                  150       160       170       180

4ST3Gal_VI_E8_Human_FL   AAGGACGTTAGGCAAATGGCCACTGGAAAAAACCCAATGCCAGGTGG
                            190       200       210       220       230

4ST3Gal_VI_E8_Human_FL   ATAGTTTTGGCCCTAAAGTTTTAGGCTTTGGACCCAAATATCGGGCT
                              240       250       260       270       280

4ST3Gal_VI_E8_Human_FL   AGAGAATTTTGAAGTCTGATTATGTACTAAATGAGGACTACATCAAG
                                  290       300       310       320

4ST3Gal_VI_E8_Human_FL      GGGATCTATCCCTACATCTTTGCCACATTCTCTGTCCTACCCTTAGT
                         330       340       350       360       370

4ST3Gal_VI_E8_Human_FL   AGTAGAAGACAAAAATAGAAGAGAAAGCAAAAAGCTTACTAGATTGC
                              380       390       400       410       420

4ST3Gal_VI_E8_Human_FL   TACTTTCCTACAAATCCTATTGTTGGTCACAGGGAAAATGATAAAGA
                              430       440       450       460       470

4ST3Gal_VI_E8_Human_FL   AGGTGATGAAAAGGATCTAAATCAGCAGTCTTTTGTCATCAGGGTTG
                                  480       490       500       510

4ST3Gal_VI_E8_Human_FL   AAGTGACCATGTCACTCCTCAGCTAACACATTACTATAGTCACAGCA
                              520       530       540       550       560

4ST3Gal_VI_E8_Human_FL   AGTACCTTGGGATATTAGCTCAGACAGTTGTTTGTGCAATGAACTTG
                              570       580       590       600       610

4ST3Gal_VI_E8_Human_FL   CTTCCTTAAAAATGATTTAAGACATATAATTGTGTTTTTCTTTTAAA
                              620       630       640       650
```

FIG. 5A

| | |
|---|---|
| 4ST3Gal_VI_E8_Human_FL | AAGtCACCCAAAGGTTGTCTTCACAATATCCTAAAaCTGTTTCTATG<br>660       670       680       690       700 |
| 4ST3Gal_VI_E8_Human_FL | TTTAATGACTTTAGAAATCAAATAATATCTTCATGTTATCCTCCAAA<br>710       720       730       740       750 |
| 4ST3Gal_VI_E8_Human_FL | TATAATTGAGATTTTTTGGTCTAGTGTGCTGGTCCACCATATTTATG<br>760       770       780       790 |
| 4ST3Gal_VI_E8_Human_FL | TATCTTCCTTATGTATAAATCAAGGAGTCCTTGCCATTGTGGTATTC<br>800       810       820       830       840 |
| 4ST3Gal_VI_E8_Human_FL | ACAAAAGATGTTTTCCTGCGTAAGGAGTTTACTAGCCTCACAGTTCA<br>850       860       870       880       890 |
| 4ST3Gal_VI_E8_Human_FL | GAAACCTAGCAATTCTAACTATGGGGATTTTGTACCCACAAAAATGG<br>900       910       920       930       940 |
| 4ST3Gal_VI_E8_Human_FL | AAAATTGTGTCTGTCCATGAAGGGTTTAGGGTATTTCCTTCATTTTG<br>950       960       970       980 |
| 4ST3Gal_VI_E8_Human_FL | AATTCTGCTGATTATAGAAGAAAATTGATTAGTTTTTAAATATGAAT<br>990      1000      1010      1020      1030 |
| 4ST3Gal_VI_E8_Human_FL | TCTTCACATAACTGATGATCATTAATAAGTTTTTGTATTAAGCTGTT<br>1040      1050      1060      1070      1080 |
| 4ST3Gal_VI_E8_Human_FL | TTCCTCTTTCCCAGCTAAGTCTGGATCCTGCCATCCACCACCCCTTT<br>1090      1100      1110      1120 |
| 4ST3Gal_VI_E8_Human_FL | CATTtATTTTCCTTGTtGTGCTCTGTCATGTTtCACAATACCCTTTT<br>1130      1140      1150      1160      1170 |
| 4ST3Gal_VI_E8_Human_FL | AAATTGTGGAGACAAGTACTCCATTCAGGAGCACAcaAGGgCCTAAC<br>1180      1190      1200      1210      1220 |
| 4ST3Gal_VI_E8_Human_FL | TTATGCCAAGAATAGAGAAGAGTTAGAAATGACTCTCAATAGTGTGA<br>1230      1240      1250      1260 |
| 4ST3Gal_VI_E8_Human_FL | TTTGTAGAGTCCCCCGGATCCCAAGGCAAGGGTCTATGGAACCTGTT<br>1270      1280      1290      1300      1310 |
| 4ST3Gal_VI_E8_Human_FL | CAGGTCAGGTGTTTCTGTGGTGTTCGCTGCCGGTGTGCGTCAGCAGA<br>1320      1330      1340      1350      1360 |
| 4ST3Gal_VI_E8_Human_FL<br>4ST3Gal_VI_E6_Human_FL | TGTGGCAGGAGGAGGTAAATAGCCACGTGCCCTTGGGGTGAGTTTCG<br>...CTGGCGGGAGCCTGAGACTCCGGGCAGGGCTGCTCCCTCCTCTG<br>1370      1380      1390      1400      1410 |
| 4ST3Gal_VI_E8_Human_FL<br>4ST3Gal_VI_E6_Human_FL | GTTTCTCCAGCTTTCAGGGACTTCTAAAAAGTGAGCCTGGTTGCAGC<br>CTCCCCCGCCAGATCCGCGGGGAAGGAATCGTGCCCGCGCCGCCCCT<br>1420      1430      1440      1450 |
| 4ST3Gal_VI_E8_Human_FL<br>4ST3Gal_VI_E6_Human_FL | TTCTACAATGCAGTAATCCTGGCCCTTCTCTGAAGGTCCTTTGAATC<br>GGCCCGCGCCACCTTCCTTTGGTTTCTGCCGGCCTCGGGCTTCTGCG<br>1460      1470      1480      1490      1500 |
| 4ST3Gal_VI_E8_Human_FL<br>4ST3Gal_VI_E6_Human_FL | ATTGCTCTTGGAATCACTTCTGGGTTGCTCATCACCTCAGCTTTTCC<br>GCCCGATGTGGCAGGCGCCGCGAGAGAGGCAGCAGCCGGCTGGAGCA |

FIG. 5B

```
                         1510       1520       1530       1540       1550
4ST3Gal_VI_E8_Human_FL    ACCCTCCCTTTCCTTACATCCATGAATCTCAGGTGTGTGTAGGGCTT
4ST3Gal_VI_E6_Human_FL    GCGGCCCCTCAGGTCTCGGAGCCCGGTGCGCCTCTGCGGTCGTCGCT
                            1560       1570       1580       1590

4ST3Gal_VI_E8_Human_FL    GGAGAAGGTACTGGCAGACCTCAAGAGGTGCAGGGAGTATTTTTGTT
4ST3Gal_VI_E6_Human_FL    CCTGGGCCTCGGCGGGTCACTCTTGCCGGCCGGCTTCGCTGCGGGTT
                     1600       1610       1620       1630       1640

4ST3Gal_VI_E8_Human_FL    TGCTGCCACAGAACCTCTCAGTGGTGGCATGAATGAGTTCCCAGGGC
4ST3Gal_VI_E6_Human_FL    TGCACTGCCCGGGTGAGCCAGCCATGAGAGGGTATCTTGTGGCCATA
                         1650       1660       1670       1680       1690

4ST3Gal_VI_E8_Human_FL    ATTTGCTTCCcTTTGGGCAgGGTGCCCGGtTCTGGtTTCTGACTGAC
4ST3Gal_VI_E6_Human_FL    TTCCTGAGTGCTGTCTTCCTCTATTATGTACTGCATTGCATATTATG
                              1700       1710       1720       1730

4ST3Gal_VI_E8_Human_FL    ATTATTTTTGtCTCATAgGGTGGCACCTGTGGAAATGAAACGGAGAA
4ST3Gal_VI_E6_Human_FL    GGGAACGAATGTCTATTGGGTGGCACCTGTGGAAATGAAACGGAGAA
                       1740       1750       1760       1770       1780

4ST3Gal_VI_E8_Human_FL    ATAAGATCCAgCCTTGTTtATCAAAGCCAGCTTTTGCcTCTCTGCTG
4ST3Gal_VI_E6_Human_FL    ATAAGATCCAGCCTTGTTTATCAAAGCCAGCTTTTGCCTCTCTGCTG
                              1790       1800       1810       1820       1830

4ST3Gal_VI_E8_Human_FL    AGTCAgAGCTCTGCATATATTTTAAGAAAAGGCATTGAGGAACTCAA
4ST3Gal_VI_E6_Human_FL    AG.............................................
                              1840       1850       1860       1870       1880

4ST3Gal_VI_E8_Human_FL    TCAAACCAGTATTCTTTTCACACAGGTTtCATCAGTTTCACCCTTTT
4ST3Gal_VI_E6_Human_FL    ........................GTTTCATCAGTTTCACCCTTTT
                                         1890       1900       1910       1920

4ST3Gal_VI_E8_Human_FL    CTGTGTGCGGCTGATTTTAGAAAGATTGCTTCCTTGTATGGTAGCGA
4ST3Gal_VI_E6_Human_FL    CTGTGTGCGGCTGATTTTAGAAAGATTGCTTCCTTGTATGGTAGCGA
                         1930       1940       1950       1960       1970

4ST3Gal_VI_E8_Human_FL    TAAGTTTGATTTGCCCTATGGgATGAGAACATCAGCGGAAtAtTTTC
4ST3Gal_VI_E6_Human_FL    TAAGTTTGATTTGCCCTATGGGATGAGAACATCAGCGGAATATTTTC
                              1980       1990       2000       2010       2020

4ST3Gal_VI_E8_Human_FL    GACTTGcTCTTtCaAAACTGCAGAGTtGTGaTCTCTTTGATGAGTTT
4ST3Gal_VI_E6_Human_FL    GACTTGCTCTTTCAAAACTGCAGAGTTGTGATCTCTTTGATGAGTTT
                              2030       2040       2050       2060

4ST3Gal_VI_E8_Human_FL    GaCAaCATACCCTGTAAAAAGTGTGTGGTGGTTGGtAATGgAGGAGT
4ST3Gal_VI_E6_Human_FL    GACAACATACCCTGTAAAAAGTGTGTGGTGGTTGGTAATGgAgGAGT
                     2070       2080       2090       2100       2110

4ST3Gal_VI_E8_Human_FL    TTTGAAGAATAAGaCATTAGGAGAAAAAATCGACTCCTATGATGTAA
4ST3Gal_VI_E6_Human_FL    TTTGAAGAATAAGACATTAGGAGAAAAAATCGACTCCTATGATGTAA
                              2120       2130       2140       2150       2160

4ST3Gal_VI_E8_Human_FL    TAATAAGAATGAATAATGGtCCTGTTTTAGgACATGAAGAAGAaGTt
4ST3Gal_VI_E6_Human_FL    TAATAAGAATGAATAATGGTCCTGTTTTAGGACATGAAGAAGAAGTT
                              2170       2180       2190       2200

4ST3Gal_VI_E8_Human_FL    GgGAGAAGGaCAaCCTTCCGACTTTTTTATCCAGAATCTGTTTTTTC
```

FIG. 5C

```
4ST3Gal_VI_E6_Human_FL    GGGAGAAGGACAACCTTCCGACTTTTTTATCCAGAATCTGTTTTTTC
                    2210      2220      2230      2240      2250

4ST3Gal_VI_E8_Human_FL    AGATCCTATTCACAATGaCCCTAATACGACAGTGATTCTCACTGCTT
4ST3Gal_VI_E6_Human_FL    AGATCCTATTCACAATGACCCTAATACGACAGTGATTCTCACTGCTT
                    2260      2270      2280      2290      2300

4ST3Gal_VI_E8_Human_FL    TTAAGCCACATGATTTAAGGTGGCTGTtGGAATTGTTGATGGGTGAC
4ST3Gal_VI_E6_Human_FL    TTAAGCCACATGATTTAAGGTGGCTGTTGGAATTGTTGATGGGTGAC
                    2310      2320      2330      2340      2350

4ST3Gal_VI_E8_Human_FL    AAAATAAACACTAATGGTTTTTGGAAGAAACCAGCCTTAAACCTGAT
4ST3Gal_VI_E6_Human_FL    AAAATAAACACTAATGGTTTTTGGAAGAAACCAGCCTTAAACCTGAT
                    2360      2370      2380      2390

4ST3Gal_VI_E8_Human_FL    TTATAAACCTTATCAAATCCGAATATTAGATCCTTTCATTATCAGAA
4ST3Gal_VI_E6_Human_FL    TTATAAACCTTATCAAATCCGAATATTAGATCCTTTCATTATCAGAA
                    2400      2410      2420      2430      2440

4ST3Gal_VI_E8_Human_FL    CAGCAGCTTATGAACTGCTTCATTTTCcAAAAGTGTTTCCCAAAAAT
4ST3Gal_VI_E6_Human_FL    CAGCAGCTTATGAACTGCTTCATTTTCCAAAAGTGTTTCCCAAAAAT
                    2450      2460      2470      2480      2490

4ST3Gal_VI_E8_Human_FL    CAGAAACcTaAACACCCAACAACAGgAATTATTGCCATCACATTGGC
4ST3Gal_VI_E6_Human_FL    CAGAAACCTAAACACCCAACAACAGGAATTATTGCCATCACATTGGC
                    2500      2510      2520      2530

4ST3Gal_VI_E8_Human_FL    GTTTTACATATGTCACGAAGTTCACCTAGCTGGTTTTAAAtACAACT
4ST3Gal_VI_E6_Human_FL    GTTTTACATATGTCACGAAGTTCACCTAGCTGGTTTTAAATACAACT
                2540      2550      2560      2570      2580

4ST3Gal_VI_E8_Human_FL    TTTcTGACCTCAAgAGTCCTTTGCACTACTATgGGAATGCCACCATG
4ST3Gal_VI_E6_Human_FL    TTTCTGACCTCAAGAGTCCttTGCACTACTATgGGAATGCCACCATG
                    2590      2600      2610      2620      2630

4ST3Gal_VI_E8_Human_FL    TCTTTGATGAATAAGAACGcGTATCACAATGTGACTGCAGAGCAGCT
4ST3Gal_VI_E6_Human_FL    TCTTTGATGAATAAGAACGcGTATCACAATGTGACTGCAGAGCAGCT
                    2640      2650      2660      2670

4ST3Gal_VI_E8_Human_FL    CTTTTTGAAGGACATTATAGAAAAAAACCTcGTAATCAACTTGACTC
4ST3Gal_VI_E6_Human_FL    CTTTTTGAAGGACATTATAGAAAAAAACCTcGTAATCAACTTGACTC
                2680      2690      2700      2710      2720

4ST3Gal_VI_E8_Human_FL    AAGATTGACTCTACAGACTCAGAAGATGATGCTAACAGTGTTAGTTT
4ST3Gal_VI_E6_Human_FL    AAGATTGACTCTACAGACTCAGAAGATGATGCTAACAGTGTTAGTTT
                    2730      2740      2750      2760      2770

4ST3Gal_VI_E8_Human_FL    TATTTTTGTACTGCAATTTTTAGTTTAAAATATGTTGgATGCACTCG
4ST3Gal_VI_E6_Human_FL    TATTTTTGTACTGCAATTTTTAGTTTAAAATATGTTGgATGCACTCG
                     2780      2790      2800      2810      2820

4ST3Gal_VI_E8_Human_FL    TCAAATAATTATGTATACTGTCTGTTGCTGCTGGTGATTCATAACCA
4ST3Gal_VI_E6_Human_FL    TCAAATAATTATGTATACTGTCTGTTGCTGCTGGTGATTCATAACCA
                    2830      2840      2850      2860

4ST3Gal_VI_E8_Human_FL    CCAGcTTAATTTCTGTGAATACTGTATATTTAACTTATGAAAACCAA
4ST3Gal_VI_E6_Human_FL    CCAGcTTAATTTCTGTGAATACTGTATATTTAACTTATGAAAACCAA
                    2870      2880      2890      2900      2910
```

FIG. 5D

```
4ST3Gal_VI_E8_Human_FL    GAAATGTAAAGATAACAGGAAAATAAGTTTTGATTGCAATGTTTTTA
4ST3Gal_VI_E6_Human_FL    GAAATGTAAAGATAACAGGAAAATAAGTTTTGATTGCAATGTTTTTA
                              2920      2930      2940      2950      2960

4ST3Gal_VI_E8_Human_FL    AAAAAAAAAAAAAAAAAAAAAAAAAAAAAAAA~~~~~~~~~~~~~~~~
4ST3Gal_VI_E6_Human_FL    AAAAAAAAAAAAAAAAAAAAAAAAAAAAAAAA~~~~~~~~~~~~~~~~
                              2970      2980      2990      3000
```

FIG. 5E

Human 7ST6Gal V Full length

```
     CTAATCTCTGCAACAGCCGCGCTTCCCGGGTCCCGCGGCTCCCGCGCGCGATCTGCCGCG
  1  ------------+---------+---------+---------+---------+---------+  60
     GATTAGAGACGTTGTCGGCGCGAAGGGCCCAGGGCGCCGAGGGCGCGCGCTAGACGGCGC

GCCGGCTGCTGGGCAAAAATCAGAGCCGCCTCCGCCCCATTACCCATCATGGAAACCCTC
 61  ------------+---------+---------+---------+---------+---------+ 120
     CGGCCGACGACCCGTTTTTAGTCTCGGCGGAGGCGGGGTAATGGGTAGTACCTTTGGGAG

CAGGAAAAAGTGGCCCCGGACGCGCGAGCCTGAGGATTCTGCACAAAAGAGGTGCCCAAA
121  ------------+---------+---------+---------+---------+---------+ 180
     GTCCTTTTTCACCGGGGCCTGCGCGCTCGGACTCCTAAGACGTGTTTTCTCCACGGGTTT

ATGAAGACCCTGATGCGCCATGGTCTGGCAGTGTGTTTAGCGCTCACCACCATGTGCACC
181  ------------+---------+---------+---------+---------+---------+ 240
     TACTTCTGGGACTACGCGGTACCAGACCGTCACACAAATCGCGAGTGGTGGTACACGTGG
      M  K  T  L  M  R  H  G  L  A  V  C  L  A  L  T  T  M  C  T   -

AGCTTGTTGCTAGTGTACAGCAGCCTCGGCGGcCAGAAGGAGCGGcCCCCGCAGCAGCAG
241  ------------+---------+---------+---------+---------+---------+ 300
     TCGAACAACGATCACATGTCGTCGGAGCCGCCgGTCTTCCTCGCCgGGGGCGTCGTCGTC
      S  L  L  V  Y  S  S  L  G  G  Q  K  E  R  P  P  Q  Q  Q   -

CAGCAGCAGCAGCAACAGCAGCAGCAGGCGTCGGcCACCGGCAGCTCGcAgCCGGCGGCG
301  ------------+---------+---------+---------+---------+---------+ 360
     GTCGTCGTCGTCGTTGTCGTCGTCGTCCGCAGCCgGTGGCCGTCGAGCgTcGGCCGCCGC
      Q  Q  Q  Q  Q  Q  Q  Q  Q  A  S  A  T  G  S  S  Q  P  A  A   -

GAGAGCAGCACCCAgCAGCGcCCCGGGGTcCCCGCGGGACCGCGgcCACTGGACGGaTAC
361  ------------+---------+---------+---------+---------+---------+ 420
     CTCTCGTCGTGGGTcGTCGCgGGGCCCCAgGGGCGCCCTGGCGCcgGTGACCTGCCtATG
      E  S  S  T  Q  Q  R  P  G  V  P  A  G  P  R  P  L  D  G  Y   -

CTCGGAGTGGCGGAcCACAAgCCCCTGAAAATGCACTGCAGGGACTGTGCCCTGGTGACC
421  ------------+---------+---------+---------+---------+---------+ 480
     GAGCCTCACCGCCtGGTGTTcGGGGACTTTTACGTGACGTCCCTGACACGGGACCACTGG
      L  G  V  A  D  H  K  P  L  K  M  H  C  R  D  C  A  L  V  T   -

AGCTCAGGGCATCTGCTGCACAGTCGGCAAGGCTCCCAGATTGACCAGACAGAGTGTGTC
481  ------------+---------+---------+---------+---------+---------+ 540
     TCGAGTCCCGTAGACGACGTGTCAGCCGTTCCGAGGGTCTAACTGGTCTGTCTCACACAG
      S  S  G  H  L  L  H  S  R  Q  G  S  Q  I  D  Q  T  E  C  V   -

ATCCGCATGAATGACGCCCCCACaCGCGGCTATGGGCGTGACGTGGGCAATCGCACCAGC
541  ------------+---------+---------+---------+---------+---------+ 600
     TAGGCGTACTTACTGCGGGGGTGtGCGCCGATACCCGCACTGCACCCGTTAGCGTGGTCG
      I  R  M  N  D  A  P  T  R  G  Y  G  R  D  V  G  N  R  T  S   -

CTGAGGGTCATCGCGCATTCCAGCATCCAGAGGATCCTCCGCAACCGCCATGACCTGCTC
601  ------------+---------+---------+---------+---------+---------+ 660
```

FIG. 6A

```
                  GACTCCCAGTAGCGCGTAAGGTCGTAGGTCTCCTAGGAGGCGTTGGCGGTACTGGACGAG

L   R   V   I   A   H   S   S   I   Q   R   I   L   R   N   R   H   D   L   L    -

AACGTGAGCCAGGGCACCGTGTTCATCTTCTGGGGCCCCAGCAGCTACATGCGGCGGGAC
      661  ---------+---------+---------+---------+---------+---------+  720
           TTGCACTCGGTCCCGTGGCACAAGTAGAAGACCCCGGGGTCGTCGATGTACGCCGCCCTG

N   V   S   Q   G   T   V   F   I   F   W   G   P   S   S   Y   M   R   R   D    -

GGCAAGGGCCAGGTCTACAACAACCTGCATCTCCTGAGCCAGGTGCTGCCCCGGCTGAAG
      721  ---------+---------+---------+---------+---------+---------+  780
           CCGTTCCCGGTCCAGATGTTGTTGGACGTAGAGGACTCGGTCCACGACGGGGCCGACTTC

G   K   G   Q   V   Y   N   N   L   H   L   L   S   Q   V   L   P   R   L   K    -

GCCTTCATGATTACTCGCCACAAGATGCTGCAGTTTGATGAGCTCTTCAAGCAGGAGACT
      781  ---------+---------+---------+---------+---------+---------+  840
           CGGAAGTACTAATGAGCGGTGTTCTACGACGTCAAACTACTCGAGAAGTTCGTCCTCTGA

A   F   M   I   T   R   H   K   M   L   Q   F   D   E   L   F   K   Q   E   T    -

GGCAAAGACAGGAAGATATCCAACACTTGGCTcAgCACTGGCTGGTTTACAATGaCAATT
      841  ---------+---------+---------+---------+---------+---------+  900
           CCGTTTCTGTCCTTCTATAGGTTGTGAACCGAgTcGTGACCGACCAAATGTTACtGTTAA

G   K   D   R   K   I   S   N   T   W   L   S   T   G   W   F   T   M   T   I    -

GcACTGGAgCTCTGTGACAGGATCAATGtTTATGGcATGGTGCCCcCAGACTTCTGCAGG
      901  ---------+---------+---------+---------+---------+---------+  960
           CgTGACCTcGAGACACTGTCCTAGTTACaAATACCgTACCACGGGgGTCTGAAGACGTCC

A   L   E   L   C   D   R   I   N   V   Y   G   M   V   P   P   D   F   C   R    -

GATCCCAATCACCCTTCAGTACCTTATCATTATTATGAACCTTTTGGACCTGATGAATGT
      961  ---------+---------+---------+---------+---------+---------+  1020
           CTAGGGTTAGTGGGAAGTCATGGAATAGTAATAATACTTGGAAAACCTGGACTACTTACA

D   P   N   H   P   S   V   P   Y   H   Y   Y   E   P   F   G   P   D   E   C    -

ACAATGTACCTCTCCCATGAGCGAGGACGCAAGGGCAGTCATCACCGCTTTATCACAGAG
     1021  ---------+---------+---------+---------+---------+---------+  1080
           TGTTACATGGAGAGGGTACTCGCTCCTGCGTTCCCGTCAGTAGTGGCGAAATAGTGTCTC

T   M   Y   L   S   H   E   R   G   R   K   G   S   H   H   R   F   I   T   E    -

AAACGAGTCTTTAAGAACTGGGCACGGACATTCAATATTCACTTTTTTCAACCAGACTGG
     1081  ---------+---------+---------+---------+---------+---------+  1140
           TTTGCTCAGAAATTCTTGACCCGTGCCTGTAAGTTATAAGTGAAAAAAGTTGGTCTGACC

K   R   V   F   K   N   W   A   R   T   F   N   I   H   F   F   Q   P   D   W    -

AAACCAGAATCACTTGCTATAAATCATCCTGAGAATAAACCTGTGTTCTAAGGAATGAGC
     1141  ---------+---------+---------+---------+---------+---------+  1200
           TTTGGTCTTAGTGAACGATATTTAGTAGGACTCTTATTTGGACACAAGATTCCTTACTCG

K   P   E   S   L   A   I   N   H   P   E   N   K   P   V   F   *

ATGCCAGACTGTAATCCCAGGTATTCACTGCATCAGACACCGAGACACTGAACTTCCTGA
     1201  ---------+---------+---------+---------+---------+---------+  1260
```

FIG. 6B

```
           TACGGTCTGACATTAGGGTCCATAAGTGACGTAGTCTGTGGCTCTGTGACTTGAAGGACT
           GCCACCAGACAGGAAAGGGTAGCAGAAAACAGCTTCACTCCTCAGGAAGTACCATGGACA
     1261  ---------+---------+---------+---------+---------+---------+ 1320
           CGGTGGTCTGTCCTTTCCCATCGTCTTTTGTCGAAGTGAGGAGTCCTTCATGGTACCTGT

GACGCCTACCAGGGGTGACAAAGCAGTGCAGTTGGATTGTAAGGAAAAATTCCGGAATTA
     1321  ---------+---------+---------+---------+---------+---------+ 1380
           CTGCGGATGGTCCCCACTGTTTCGTCACGTCAACCTAACATTCCTTTTTAAGGCCTTAAT

ATGCATCCTAATGAATGTTGTCCCCTTCAATGGTGTTACCTTAGGAGCTGAACATTCAAT
     1381  ---------+---------+---------+---------+---------+---------+ 1440
           TACGTAGGATTACTTACAACAGGGGAAGTTACCACAATGGAATCCTCGACTTGTAAGTTA

TCAGTTACACCACTATGACTAAAAACAGTTTGGATCTCTTAGTATTGCCTTTGAAACTGC
     1441  ---------+---------+---------+---------+---------+---------+ 1500
           AGTCAATGTGGTGATACTGATTTTTGTCAAACCTAGAGAATCATAACGGAAACTTTGACG

AACATAAGCAACTCAACAATATTAGTTGCATTCCTTTATAGACATACCATGTCAAAGACG
     1501  ---------+---------+---------+---------+---------+---------+ 1560
           TTGTATTCGTTGAGTTGTTATAATCAACGTAAGGAAATATCTGTATGGTACAGTTTCTGC

TTTTTCTATCAAGTTGTATTCTTTCcTGTtCtATAaCCTTtGTCATCTGTtAGaCTCTGT
     1561  ---------+---------+---------+---------+---------+---------+ 1620
           AAAAAGATAGTTCAACATAAGAAAGgACAaGaTATtGGAAaCAGTAGACAaTCtGAGACA

ATGtGTGATTTGTAAAAAGCAGGCTGAAACTATGGACATGATTTCTGAAGAGCACATCTC
     1621  ---------+---------+---------+---------+---------+---------+ 1680
           TACaCACTAAACATTTTTCGTCCGACTTTGATACCTGTACTAAAGACTTCTCGTGTAGAG

CACTGaCTTTCATAAAGCAAATGTCCAATATTTATTTATTGAGAGTTTTTTAGtGCAATC
     1681  ---------+---------+---------+---------+---------+---------+ 1740
           GTGACtGAAAGTATTTCGTTTACAGGTTATAAATAAATAACTCTCAAAAAATCaCGTTAG

TGGGCCAGTATTTTTATAGATTATGATTATGTGGTAATTTATCCTTCCTAACTCTTTAAT
     1741  ---------+---------+---------+---------+---------+---------+ 1800
           ACCCGGTCATAAAAATATCTAATACTAATACACCATTAAATAGGAAGGATTGAGAAATTA

CCTGAATGATGGTTGGAAATGGCCTAGAATTAGGTTACTCTGTTCACAATGCTCATTGTT
     1801  ---------+---------+---------+---------+---------+---------+ 1860
           GGACTTACTACCAACCTTTACCGGATCTTAATCCAATGAGACAAGTGTTACGAGTAACAA

AGCATGCAATTGGTATTTGACTTGGAAGTGTTGTGTTGTATTTTTTGAACCCCTAGGCTT
     1861  ---------+---------+---------+---------+---------+---------+ 1920
           TCGTACGTTAACCATAAACTGAACCTTCACAACACAACATAAAAAACTTGGGGATCCGAA

CAGGAAAACTGCTCTTTTGTAAAAAGAATAGCGATGACATTTTCTAATGTGCAGAAATGT
     1921  ---------+---------+---------+---------+---------+---------+ 1980
           GTCCTTTTGACGAGAAAACATTTTTCTTATCGCTACTGTAAAAGATTACACGTCTTTACA

TCCAAAAGGACAAAATTGAAAACCAAAAACTATGTTATTAAAACAAAAAAATGCTAACAA
     1981  ---------+---------+---------+---------+---------+---------+ 2040
           AGGTTTTCCTGTTTTAACTTTTGGTTTTTGATACAATAATTTTGTTTTTTTACGATTGTT

AAAAAAAAAAAAAAAA
     2041  ---------+------ 2056
           TTTTTTTTTTTTTTTT
``` a

```
4ST3GalIVM     117CRRCVVVGNGHRLRNSSLGGVINKYDVVIRLNNAPVAGYEGDVGSKTTIRLFYPESAH230RILNPFFM273CDLVHLIAGFGYPDASNKKQTIHYYEQI
4ST3GalVaH     117CRRCVVVGNGHRLRNSSLGGVINKYDVVIRLNNAPVAGYEGDVGSKTTIRLFYPESAH230RILNPFFM273CDLVHLIAGFGYPDASNKKQTIHYYEQI
4ST3GalIVH     117CRRCVVVGNGHRLRNSSLGDAINKYDVVIRLNNAPVAGYEGDVGSKTTMRLFYPESAH230RILNPFFM273CDLVHLIAGFGYPDAYNKKQTIHYYEQI
4ST3GalIIIM    156CRRCIIVGNGGVLANKSLGSRIDDYDIVIRLNSAPVKGFERDVGSKTTLRITYPEGAM269RILNPYFI313CDEVAVAGFGYDM.NTPNAPLHYYETV
4ST3GalIIIR    156CRRCIIVGNGGVLANKSLGSRIDDYDIVIRLNSAPVKGFEKDVGSKTTLRITYPEGAM269RILNPYFI313CDEVAVAGFGYDM.NTPNAPLHYYETV
4ST3GalIIIH    157CRRCIIVGNGGVLANKSLGSRIDDYDIVVRLNSAPVKGFEKDVGSKTTLRITYPEGAM270RILNPYFI314CDEVAVAGFGYDM.STPNAPLHYYETV
5ST3GalIIM     149CRRCAVVGNSNLRGSGYGQEVDSHNFIMRMNQAPTVGFEKDVGSHNFIMRMNQAPTVGFEKDVGSRTTHHFMYPESAK255QIYNPAFF291CDEVNVYGFGADSRGN...WIRHWENN
5ST3GalIIR     149CRRCAVVGNSNLRGSGYGQEVDSHNFIMRMNQAPTVGFEKDVGSRTTHHFMYPESAK255QIYNPAFF291CDEVNVYGFGADSRGN...WIHHWENN
5ST3GalIIH     149CRRCAVVGNSNLRGSGYGQDVDGHNFIMRMNQAPTVGFEQDVGSRTTHHFMYPESAK255QIYNPAFF291CDEVNVYGFGADSRGN...WIHHWENN
5ST3GalIH      139CRRCAVVGNSGNLRESSYGPEIDSHDFVLRMNKAPTVGFEADVGTKTTHHLVYPESFR245LIYHPAFI281CDEVDLYGFGADSKGN...WIHHWENN
5ST3GalIM      136CRRCAVVGNSGNLKDSSYGPEIDSHDFVLRMNKAPTVGFEADVGSRTTHHFVYPESFR242LIYHPAFI278CDEVDLYGFGADSKGN...WIHHWENN
5ST3GalIP      142CRRCAVVGNSGNLKESYYGPQIDSHDFVLRMNKAPTEGFEADVGSKTTHHFVYPESFR248LIYHPAFI284CDEVDLYGFGADSKGN...WIHHWENN
5ST3GalICh     141CRRCAVVGNSGNLRQSQYGQDIDSHDFVLRMNRAPTIGYESDVGSKTTHHFVYPESYK247LIYNPSFI283CDEVNVYGFGADSKGH...WIHHWENN
```

FIG. 9B

```
        1F →              2F →                           3F →                        4F →                        2R                    1R                    STP-R
        CRRCVVVGNGH       CRRCVVVGNCH       IIISSSG       RINSAPV       MsNPIT       RLFYPEGA       HITTSNSF       RILNPFF       AGFGYD       HYYD
        LKK               A       s                       C Q R                      YFMNVQTy         QYH Y         YEYWAP       ChWE
        WNT       A

SIALYLTRANSFERASES

BACKGROUND OF THE INVENTION

Sialic acids play an important role in variety of biological functions, including cell ahesion, cell-cell communication, protein targeting, infection of cells by viruses and microorganisms, metastasis,

BRIEF DESCRIPTION OF THE DRAWINGS

FIG. 1 shows the aligned nucleotide and amino acid sequence of human (H) (SEQ ID NOS:1 and 2) and mouse (M) (SEQ ID NOS:3 and 4) GM3 synthase (4ST3 Gal IV). Position along nucleotide and amino acid sequence is indicated on the right and left margin, based on a position along mouse sequence. 1, 2, and 3-potential in frame initiation codons. The third M is selected as the first amino acid residue in the protein sequence based on homology with other sialyltransferases. STL—large sialylmotif, STS—small sialylmotif, ST3—sialylmotif specific for ST3 family of sialyltransferases, STP—petit sialylmotif, probably involved in the recognition of citidine portion of CMP-sialic acid. H*—The unique H reside in the place of D/E common to all known animal sialyltransferases. S*—The unique S residue in the place of N common to all other ST3 sialyltransferases. Non-conservely substituted amino acid residues are shown in capital bold. Stop—stop codon. The potential N-terminal transmembrane domain is shown in italic. The potential polyadenylation signal is shown in underlined italic. $(GT)_n$. fmily of repeats is shown in bold $(gt)_{27}$. $N^G$ indicates the potential N-glycosylation sites. $S^{cP}$ or $T^{cP}$—indicates the potential cAMP and cGMP-dependent protein kinase phosphorylation sites. $S^{CK}$ or $T^{CK}$—indicates the potential casein kinase II phosphorylation sites (only sites conserved between mouse and human are shown). $S^C$ of $T^{CC}$ k-potential sites of phosphorylation by protein kinase with the same substrate specificity as protein kinase C. $S^{cP,C}$—serine residue that can be potentially phosphorylated by both cAMP or cGMP—dependent protein kinases and by protein kinases with the same subtrate specificity as protein kinase C. ‡ followed by the number indicates places of alternative splicing. The nucleotide sequence of the primers used for the detection of the aernatively spliced forms (ASF) in shown in bold italic. Boxed amino acid residues indicate differences with GM3-synthases published by other groups.

FIG. 2 shows the aligned nucleotide sequences of alternately spliced forms (ASF) of human GM3 synthase. ASF600 is shown in FIG. 1 ASF800(SEQ ID NO:5; ASF400 (SEQ ID NO:6).

FIG. 3 shows the nucleotide and amino acid sequence of human 4ST3Gal VI (E6) (SEQ ID NOS:7 and 8)

FIG. 4 shows the nucleotide and amino acid sequence of mouse 4ST3Gal VI (SEQ ID NOS:9 and 10).

FIG. 5 shows the alignment of nucleotide sequence of ASF E6 (full-length) (SEQ ID NO:7) and ASF E8 (SEQ ID NO:11) cDNAs for human 4ST3Gal VI.

FIG. 6 shows the nucleotide and amino acid sequence of human 7ST6Gal V (SEQ ID NOS:12 and 13).

FIG. 9(A) shows the position of the PCR primers used in this work along the amino acid sequence of the conserved ST3 domains (SEQ ID NOS:14–30). ST3Gal I to ST3Gal IV, all known ST3 sialyltransferases. M—mouse, H—Human, a—very close isoforms, R—Rat, P—Pig, and Ch—Chicken sequences. The number in front of the ST indicates belonging to a subfamily of sialyltransferases. F—forward primer, R—reverse primer, STP—petit sialylmotif, number indicates the position of amino acid reside. (B) variations in the motifs considered in the primer design. Amino acid residues shown in bold were used in combinatorial PCR in this study. Underlined amino acid residues indicate variations in the motif outside the ST3 family. Amino acid residues shown in small letters indicate variations known for only one ST. The lowest variability was found in amino acid sequence for 1F, 2F, 1R and STP motif. (C) motif in the new ubiquitously expressed members of the ST3 family isolated in this study.

DETAILED DESCRION OF THE INVENTION

Figure 7:
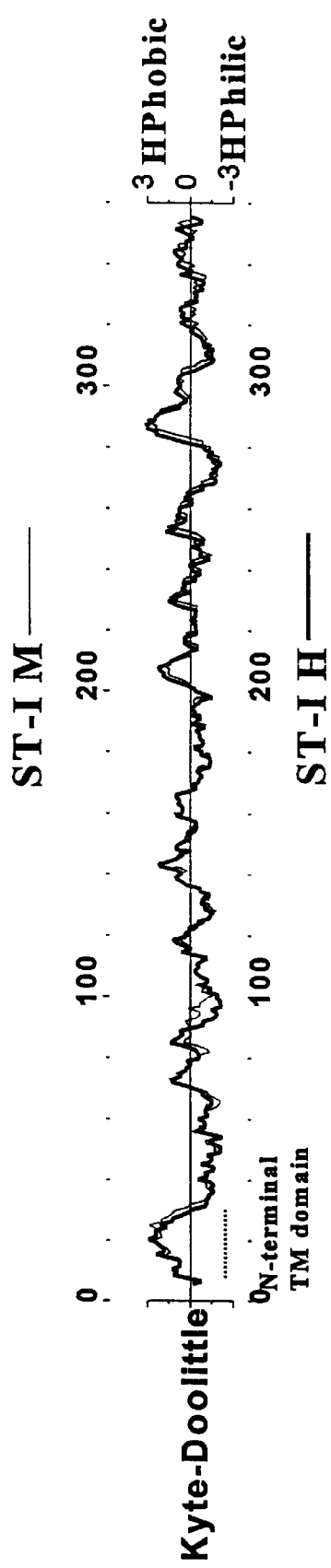
FIG. 7 shows the hydrophobicity plot of mouse (grey line) and human (black line) GM3-synthase. The dotted line indicates N-terminal transmembrane domain common to all STs.

Novel nucleic acids, polypeptide sequences, and nucleic acid regulators thereof, have been identified which code for sialyltransferases, a class of enzymes involved in the glycosylation of polypeptides, lipids, and other molecules. The sialyltransferases of the present invention, fragments thereof, and derivatives thereof, have one or more of the following biological activities, including, but not limited to: sialyltransferase activity; and a sialyltransferase-specific immunogenic activity. In accordance with the present invention, at least three novel classes of sialyltransferases have been identified: GM3-synthase or 4ST3Gal IV, 4ST3Gal VI, and 7ST6GalNAc V.

A "sialyltransferase activity" means, e.g., a catalytic activity in which a sialic acid (N-acetylneuraminic acid or NANA) is transferred from a donor molecule to an acceptor molecule. Sialyltransferase activity is exhibited by a class of enzymes generally referred to as "sialyltransferases," which differ from each other in the specificity of the sialic acid acceptor, sialic acid donor, and the anomeric linkage formed. For example, several sialic acid linkage patterns are commonly found in glycoproteins and glycolipids, e.g., Sia-alpha2,6Gal, Sia-alpha2,3Gal, Sia-alpha2,6GalNAc, Sia-alpha2,8Sia.

A "GM3-synthase or 4ST3Gal IV activity" means, e.g., a sialyltransferase catalytic activity in which a sialic acid is transferred from a sialic acid donor selectively to a 3-hydroxyl group of a galactose residue of a sialic acid acceptor. Preferably, the sialic acid donor is CMP-N-acetylneuraminic acid, N-glycolylneuraminic acid (CMP-Neu5Gc), and ketodeoxynonulosonic acid (KDN), with glycolyl or hydroxyl group at carbon 5. Preferably, the sialic acid acceptor is a galactose residue of a pendant glycoprotein or glycolipid sugar chain, such as lactosylceramide (LacCer). It is also known as Lactosylceramide alpha-2,3-sialyltransferase (EC 2.4.99.9). The reaction catalysed can be, e.g., CMP-N-acetylneuraminate+beta-D-galactosyl-1,4-beta-D-glucosylceramide<=>CMP+alpha-N-acetylneuraminyl-2,3-beta-D-galactosyl-1,4-beta-D-glucosylceramide. The catalytic activity can be assayed conventionally, e.g., or as described below in the examples.

A "4ST3GalVI activity" means, e.g., a catalytic activity in which a sialic acid is transferred to a terminal galactose residue resulting in the formation of a (α2–3) linkage.

A "7ST6NAcGalV activity" means, e.g., a catalytic activity in which a sialic acid is transferred to a GalNAc residue with the formation of (α2–6) bond.

By the term "sialyltransferase-specific immunogenic activity", it is meant that a sialyltransferase polypeptide elicits an immunological response which is selective for the sialyltransferase, e.g., an immunological response which is selective for mammalian ST3Gal IV, 4ST3Gal VI, and 7STGalNAcGal V. Such response can be cellular or humoral. Thus, the stimulation of antibodies, T-cells, macrophages, B-cells, dendritic cells, etc., by an amino acid sequence selected from a mammalian sialyltransferase, e.g., a human or mouse GM3-synthase as shown in FIG. 1 (SEQ ID NOS:1–4), is a specific immunogenic activity. These responses can be measured routinely.

A mammalian sialyltransferase, such as a human and mouse GM3 synthase, human and mouse 4ST3Gal VI, and human 7STGalNAc V, is a mammalian polypeptide having an amino acid sequence which is obtainable from a natural source and which has one or more of the afore-mentioned activities. It can have sequences as shown in FIGS. 1–6 (SEQ ID NOS:1–13), having an open-reading frame that begins with an initiation codon and ends with a stop codon. It can also comprise a fragment of such sequence and possess a biological-activity as described above and below. It therefore includes naturally-occurring normal, naturally-occurring mutant, and naturally-occurring polymorphic, etc., sequences. Natural sources include, e.g., living cells, e.g., obtained from tissues or whole organisms, cultured cell lines, including primary and immortalized cell lines, biopsied tissues, etc.

The present invention also relates to fragments of a mammalian sialyltransferase, especially, human and mouse GM3 synthase, human and mouse 4ST3Gal VI, and human 7STGalNAc V. The fragments are preferably "biologically active". By "biologically active", it is meant that the polypeptide fragment possesses an activity in a living system or with components of a living system. Biological activities include those mentioned, e.g., sialyltransferase activity and sialyltransferase-immunogenic activity. Fragments can be prepared according to any desired method, including, chemical synthesis, genetic engineering, cleavage products, etc. A biological-fragment of a sialytransferase, e.g., human and mouse GM3 synthase, human and mouse 4ST3Gal VI, and human 7STGalNAc V, includes polypeptides which have had amino acid sequences removed or modified at either the carboxy- or amino-terminus of the protein, e.g., processing to a mature from a pro-form.

Preferably, the following nucleic acid fragments and polypeptide fragments coded for by such fragments, expressed as accession numbers and their dates, are excluded:

For human GM3 synthase: AA604937-1998; AA833733-1998; AA848052-1998; AA648992-1997; AA648973-1997; AI150920-1998; N40410-1996; AA969297-1998; AA429546-1997; AA482611-1997; AI038475-1998; AA386324-1997; AI359060-1999; AA448834-1997; AA827206-1998; AA297799-1997; W56658-1996; AA649318-1997; W56550-1996; AA383443-1997; AI364968-1999; AA428458-1997; AA954095-1998; R93279-1996; T95985-1995; R13431-1995; AI123263-1998; AI089834-1998; R40943-1995; AA383409-1997; AA298186-1997; N98461-1996; AA928319-1998; AA359739-1997; AA934042-1998; AA127477-1996; C01821-1996; R93185-1996; W30980-1996; R88774-1995; AI192267-1998; R18785-1995; AA757529-1998; T95887-1995; T48553-1995; R88773-1995; AA448833-1997.

For mouse GM3 synthase: AA395997-1997; AA208995-1997; AA274576-1997 Ai322283-1998; AA117276-1996; W36875-1996; Ai324739-1998; AA068897-1997; AA638055-1997; AA592148-1997; AA038269-1996; AA656084-1997.

For human 4ST3Gal VI: AA883549-1998; AI243565-1998; AI127642-1998; N40607-1996; AA884052-1998; T16968-1996; W52470-1996; H19227-1995; H06247-1995; HSC1JB012-1995; H22233-1995; T17210-1996; AA186848-1998—starting at position 60; N91874-1996; N91882-1996; AI263903-1998; AA932385-1998; N32295-1996 (90%).

For mouse 4ST3Gal VI: AA274765-1997; AA289561-1997; W84060-1996; AA871160-1998; AU035229-1998; AU035244-1998; AI153959-1998; AI050428-1998; AA216873-1997; AA571131-1997; AA929614-1998; AA920437-1998 (86%); AA186011-1997; MUSGS00902-1995; AA260569-1997.

For human 7ST6 GalNAc V: AA071204-1997; AA071008-1997; AA709472-1997; R59067-1995; R59068-1995; W28431-1996; HSC1JE071-1995; AI024886-1998; AA670246-1997; T80515-1995—this and below—90 nt; AA081615-1997; R13949-1995; HSC2CE101-1995; H29148-1995; HSCZQA061

The nucleotide sequences of the aforementioned nucleic acids can be identified by searching publicly available databases. However, polypeptides which contain or comprise these sequences are not excluded, e.g., full-length sialyltransferase, such as human and mouse GM3 synthase, human and mouse 4ST3Gal VI, and human 7STGalNAc V, a polypeptide having two or more of these mentioned fragments, or a polypeptide having one of the mentioned fragments and additional amino acid sequences, either from a sialyltransferase or from another source.

The present invention also relates to a human GM3 synthase having a deduced sequence of amino acids 1 to 362 amino acids as shown in FIG. 1 (SEQ ID NOS:1 and 2). The 362 amino acid polypeptide has a calculated molecular weight of about 41.74 kilodaltons and a pI of 7.50. The present invention also relates to a mouse GM3 synthase having a deduced sequence of amino acids 1 to 359 amino acids as shown in FIG. 1 (SEQ ID NOS:3 and 4). The 359 amino acid polypeptide has a calculated molecular weight of about 41.24 kilodaltons and a pI of 8.74. The degree of similarity between human and mouse GM3 synthase is 90.5%; the degree of identity is 86.4% at the amino acid level and 84.7% at the cDNA level in the coding region. The similarity in the 5' untranslated region drops to 81% and in the 3' untranslated region drops to 54%. For proteins degree of identity means number of identical amino acids/total number of amino acid residues in the protein. Degree of similarity means (number of identical amino acid residues plus number of conservatively substituted amino acids (like V for L, etc)/total number of amino acid residues. For DNA identity is the same as similarity and means the number of identical nucleotides/total length.

A hydrophobicity plot of human and mouse GM3-synthase is shown in FIG. 7. It reveals an N-terminal transmembrane domain common to all mammalian STs and a predicted type II transmembrane topology. Human and mouse ST3Gal V have a conserved: STL domain (sialylmotif L of about 44 or 45 amino acids; involved in binding donor-substrates, such as CMP-sialic acid and in catalysis; Katsutoshi, *Trends in Glycoscience and Glycotechnology*, 8:195–215, 1996; Sasaki et al., *J. Biol. Chem.*, 269:15950–15956, 1994); STS domain (sialylmotif S of about 23 amino acids; Drickamer, *Glycobiology*, 3:2–25 3, 1993; Katsutoshi, *Trends in Glycoscience and Glycolechnology*, 8:195–215, 1996); STP domain (sialylmotif P; involved in cytosine recognition of the donor CMP-sialic acid molecule through the stacking interaction of the aromatic ring of Y/F/W residues with cytosine, electrostatic interaction between amino acids H or C, and either oxygen from the cytosine or phosphate group, and electrostatic interaction between D/E or Q residue and amino group of the cytosine shown in FIG. 8); and ST3 motifs. STP motif: short motif (H, C, r)(Y, h)(Y, W, F)(D, E, h, y) small capital letter indicate occurrence in 1 enzyme; bold— occur most often. This motif is implicated in the nucleotide portion of CMP-sialic acid recognition. The Y residue may also be involved in nucleophilic attack. Antibodies which recognize this motif can be used in expression cloning of other polypeptides, especially other sialyltransferases.

Each GM3 synthase contains three potential N-glycosylation sites that are conserved for the mouse and human enzymes, five conserved potential casein kinase II phosphorylation sites, two conserved potential cAMP/cGMP-dependent protein kinase phosphorylation sites, as well as several non-conserved phosphorylation sites. Mouse ST3Gal IV has a $(GT)_{27}$ repetitive element in the 3' untranslated region.

7ST6GalNAc V has a stretch of 12 Q residues. The repeat may be involved in protein-protein interactions when the repeat is short. This region in other proteins (e.g., Huntington disease, Kennedy disease, so-called glutamine-repeat diseases) was shown to be involved in the pathogenesis of these diseases due to formation of inclusion bodies upon increase in the stretch. In these diseases if, most likely due to "slips," or mistakes of polymerase on CAG repeats (codon for Q), the Q-stretch gets increased to 30+ Q residues, insoluble precipitates form (e.g., *Nature* 352, 77–79). This same aberration can also occur for 7ST6GalNAc V and produce a pathology of Huntington-like diseases. (This protein is presence in certain parts of the brain and some tissues of neuronal origin).

The present invention also relates to a human 4ST3 GalVI having a deduced sequence of amino acids 1 to 331 amino acids as shown in FIG. 3 (SEQ ID NOS:7 and 8). The 331 amino acid polypeptide has a molecular weight of about 38.21 kilodaltons and a pI of about 9.63. The present invention also relates to a mouse 4ST3 GalVI having a deduced sequence of amino acids 1 to 329 amino acids as shown in FIG. 4 (SEQ ID NOS:9 and 10). The 329 amino acid polypeptide has a molecular weight of about 37.84 kilodaltons and a pI of about 9.90.

The present invention also relates to a human 7ST6 GalV having a deduced sequence of amino acids 1 to 336 amino acids as shown in FIG. 6 (SEQ ID NOS:12 and 13). The 336 amino acid polypeptide has a molecular weight of about 38.44 kilodaltons and a pI of about 10.24.

A sialytransferase polypeptide of the invention, e.g., having an amino acid sequence as shown in FIGS. 1–6 (SEQ ID NOS:1–13), can be analyzed by available methods to identify other structural and/or functional domains in the polypeptide, including membrane spanning regions, hydrophobic regions. For example, a sialytransferase polypeptide can be analyzed by methods disclosed in, e.g., Kyte and Doolittle, *J. Mol. Bio.*, 157:105, 1982; EMBL Protein Predict; Rost and Sander, Proteins, 19:55–72, 1994.

Other homologs of GM3-synthase, 4ST3Gal VI, and 7STGalNAc V from mammalian and non-mammalian sources can be obtained according to various methods. For example, hybridization with an oligonucleotides (e.g., any of the primers mentioned in Table I) can be employed to select homologs, e.g., as described in Sambrook et al., *Molecular Cloning*, Chapter 11, 1989. Such homologs can have varying amounts of nucleotide and amino acid sequence identity and similarity to sialyltransferase. Mammalian organisms include, e.g., rodents, mouse, rats, hamsters, monkeys, pigs, cows, etc. Non-mammalian organisms include, e.g., vertebrates, invertebrates, zebra fish, chicken, Drosophila, *C. elegans*, Xenopus, yeast such as *S. pombe*, *S. cerevisiae*, roundworms, prokaryotes, plants, Arabidopsis, viruses, artemia, etc.

The invention also relates to sialyltransferase-specific amino acid sequences, e.g., a defined amino acid sequence which is found in the particular sequences of FIGS. 1–6, (SEQ ID NOS:1–13) conserved amino acid motifs found in the sialyltransferases of the present invention, or, conserved motifs found in one or more subsets of sialyltransferases. Comparisons between related proteins, such as other sialyltransferases or glycosylases, can be used to select sequences specific for sialyltransferases. For example, protein sequences of all homologous members of the sialyltransferase family were aligned, and amino acid motifs were generated based on the conserved areas of homology. These are summarized in Table 1. Other specific and/or conserved amino acid sequences can be found routinely, e.g., by searching a gene/protein database using the BLAST set of computer programs. A sialyltransferase-specific amino acid sequence or motif can be useful to produce peptides as antigens to generate an immune response specific for it. Antibodies obtained by such immunization can be used as a specific probe for a mammalian sialyltransferase protein for diagnostic or research purposes.

As mentioned, polypeptides of the present invention can comprise various amino acid sequences for a sialyltransferase (e.g., having a start and stop codon as shown in FIGS. 1–6, a mature amino acid sequence (i.e., where the sialyltransferase polypeptide is produced as a precursor which is processed into a mature polypeptide, or fragments thereof. Useful fragments include, e.g., fragments comprising, or consisting essentially of, any of the aforementioned domains and specific and conserved amino acid sequences such as those displayed in Table 1.

A fragment of a sialyltransferase can be selected to have a specific biological activity, e.g., catalytic activity, substrate acceptor or donor binding activity, immunogenic activity, recognition and/or binding to donor substrates, such as CMP-sialic acid. The measurement of these activities is described below and in the examples. These peptides can also be identified and prepared as described in EP 496 162. A useful fragment can comprise, or consist essentially of, e.g., about nine contiguous amino acids, preferably about 10, 15, 20, 30, 40, etc. contiguous amino acids of FIGS. 1–6 (SEQ ID NOS:1–13).

A polypeptide of the present invention can also have 100% or less amino acid sequence identity to the amino acid sequence set forth in FIGS. 1–6 (SEQ ID NOS:1–13). For the purposes of the following discussion: Sequence identity means that the same nucleotide or amino acid which is found in the sequence set forth in FIGS. 1–6 (SEQ ID NOS:1–13) is found at the corresponding position of the compared sequence(s). A polypeptide having less than 100% sequence identity to the amino acid sequences set forth in FIGS. 1–6 (SEQ ID NOS:1–13) can contain various substitutions from the naturally-occurring sequence, including homologous and non-homologous amino acid substitutions. See below for examples of homologous amino acid substitution. The sum of the identical and homologous residues divided by the total number of residues in the sequence over which the sialyltransferase polypeptide is compared is equal to the percent sequence similarity. For purposes of calculating sequence identity and similarity, the compared sequences can be aligned and calculated according to any desired method, algorithm, computer program, etc., including, e.g., FASTA, BLASTA. A polypeptide having less than 100% amino acid sequence identity to the amino acid sequence of FIGS. 1–6 (SEQ ID NOS:1–13) can have about 99%, 98%, 97%, 95%, 90.5%, 90%, 85%, 70%, or as low as about 53% sequence identity. A preferred amount of amino acid sequence identity is about 86% or more, e.g., about 86.4%, 88%, 89%. See, below for discussion of mutations or muteins.

The present invention also relates to sialyltransferase muteins, i.e., any polypeptide which has an amino acid sequence which differs in amino acid sequence from an amino acid sequence obtainable from a natural source (a fragment of a mammalian sialyltransferase does not differ in amino acid sequence from a naturally-occurring sialyltransferase although it differs in amino acid number). Thus, sialyltransferase muteins comprise amino acid substitutions, insertions, and deletions, including non-naturally occurring amino acids.

Muteins to a sialyltransferase amino acid sequence of the invention can also be prepared based on homology searching from gene data banks, e.g., Genbank, EMBL. Sequence homology searching can be accomplished using various methods, including algorithms described in the BLAST family of computer programs, the Smith-Waterman algorithm, etc. A mutein(s) can be introduced into a sequence by identifying and aligning amino acids within a domain which are identical and/or homologous between polypeptides and then modifying an amino acid based on such alignment. For instance, the sialyltransferases of the present invention share sequence identity with various known sialyltransferases, e.g., ST8SiaI, ST8SiaII, ST8SiaIII, and others shown, e.g. in FIG. 9 (SEQ ID NOS:14–30). Alignments between these polypeptides, especially in regions such as the STL, STS, and STP motifs, reveal amino acid positions which are both identical and different from each other, providing information on amino acid substitutions that would be expected to reduce, decrease, or, eliminate a biological activity of a sialyltransferase, such as catalytic activity, donor-substrate binding activity, etc. For instance, where alignment reveals identical amino acids conserved between two or more domains, elimination or substitution of the amino acid(s) would be expected to adversely affect its biological activity.

Amino acid substitution can be made by replacing one homologous amino acid for another. Homologous amino acids can be defined based on the size of the side chain and degree of polarization, including, small nonpolar: cysteine, proline, alanine, threonine; small polar: serine, glycine, aspartate, asparagine; large polar: glutamate, gluine, lysine, arginine; intermediate polarity: tyrosine, histidine, tryptophan; large nonpolar: phenylalanine, methionine, leucine, isoleucine, valine. Homologous acids can also be grouped as follows: uncharged polar R groups, glycine, serine, threonine, cysteine, tyrosine, asparagine, glutamine; acidic amino acids (negatively charged), aspartic acid and glutamic acid; basic amino acids (positively charged), lysine, arginine, histidine.

Homologous amino acids also include those described by Dayhoff in the Atlas of Protein Sequence and Structure 5, 1978, and by Argos in EMBO J., 8, 779–785, 1989.

The invention relates to mutein polypeptides and mutein nucleic acids coding for such polypeptides. Thus, the present invention relates to nucleotide sequences of FIGS. 1–6 (SEQ ID NOS:1–13), wherein said nucleic acids code for a polypeptide and one or more amino acid positions are substituted or deleted, or both, and the polypeptide coded for by the nucleic acid has a biological activity, such as sialic acid transfer activity, catalytic activity, or substrate binding activity. A polypeptide mutein, and its corresponding nucleotide coding sequence, can have an amino acid sequence as set forth in FIGS. 1–6 (SEQ ID NOS:1–13), except where one or more positions are substituted by homologous amino acids, e.g., where there are 1, 5, 10, 15, or 20 substitutions. How a modification affects the mentioned activities can be measured according to the methods described above, below, and as the skilled worker in the field would know. For example, assays for sialyltransferase can be accomplished as disclosed in the examples below, Kurosawa et al., *J. Biol. Chem.*, 269:19048–19053, 1994; Tsunoda et al., *Biochemistry*, 34:9356–9367, 1995; Chang et al., *Glycobiology*, 5:319–325, 1995; Sjoberg et al., *J. Biol. Chem.*, 271:7450–7459, 1996; Kono et al., *J. Biol. Chem.*, 271:29366–29371, 1996; Ma et al., *J. Biol. Chem.*, 272:672–679, 1997; U.S. Pat. No. 5,494,790; U.S. Pat. No. 5,409,817; WO97/47749.

As mentioned, amino acid substitutions can also be made based on analogy to related other sialyltransferases and glycosylases. Other mutations could be selected routinely by modifying or mutating a nucleotide sequence of FIGS. 1–6 (SEQ ID NOS:1–13), and selecting for those mutations that affect one or more its activities, e.g., by measuring sialyltransferase activity according to the methods and examples described below.

A mammalian sialyltransferase of the present invention, fragments, or substituted polypeptides thereof, can also comprise various modifications, where such modifications include lipid modification, methylation, phosphorylation, glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

Polypeptides of the present invention (e.g., full-length, fragments thereof, mutations thereof) can be used in various ways, e.g., in assays, as immunogens for antibodies as described below, as biologically-active agents (e.g., having one or more of the activities associated with a sialyltransferase).

A polypeptide coding for a sialyltransferase of the present invention, a derivative thereof, or a fragment thereof, can be combined with one or more structural domains, functional domains, detectable domains, antigenic domains, and/or a desired polypeptide of interest, in an arrangement which does not occur in nature, i.e., not naturally-occurring. A polypeptide comprising such features is a chimeric or fusion polypeptide. Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous (e.g., with multiple N-terminal domains to stabilize or enhance activity) or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as signaling, growth promoting, cellular targeting (e.g., signal sequence, targeting sequence, such as targeting to the endoplasmic reticulum or nucleus), etc., a structural function such as hydrophobic, hydrophilic, membrane-spanning, etc., receptor-ligand functions, and/or detectable functions, e.g., combined with enzyme, fluorescent polypeptide, green fluorescent protein, (Chalfie et al., *Science*, 263:802, 1994; Cheng et al., *Nature Biotechnology*, 14:606, 1996; Levy et al., *Nature Biotechnology*, 14:610, 1996), etc. In addition, a polypeptide, or a part of it, can be used as a selectable marker when introduced into a host cell. For example, a nucleic acid coding for an amino acid sequence according to the present invention can be fused in-frame to a desired coding sequence and act as a tag for purification, selection, or marking purposes. The region of fusion can encode a cleavage site to facilitate expression, isolation, purification, etc.

A polypeptide according to the present invention can be produced in an expression system, e.g., in vivo, in vitro, cell-free, recombinant, cell fusion, etc., according to the present invention. Modifications to the polypeptide imparted by such systems include glycosylation, amino acid substitution (e.g., by differing codon usage), polypeptide processing such as digestion, cleavage, endopeptidase or exopeptidase activity, attachment of chemical moieties, including lipids and phosphates, etc.

A polypeptide according to the present invention can be recovered from natural sources, transformed host cells (culture medium or cells) according to the usual methods, including, detergent extraction (e.g., non-ionic detergent, Triton X-100, CHAPS, octylglucoside), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. A sialyltransferase polypeptide can also be isolated as described for other sialyltransferases proteins as the skilled worker would know. See, e.g., WO97/47749. Traditionally, CMP-sialic acid gets oxidized and with sodium periodate and conjugated to sepharose, or any other matrix. Another approach for affinity chromatography would be linking a sialic acid acceptor to a sepharose matrix. In general (besides less efficient size-fractionation, isoelectric focusing, ion exchange, hydrophobic, etc.), affinity chromatography can be utilized to isolate the enzymes in accordance with present invention where an enzyme substrate, inhibitor, or transitional state analog, is coupled to a solid support. Following binding and elution, the protein can be applied to additional affinity matrix, or further fractionated by size or charge. In addition, since this protein is known to reside in the internal compartments it can be glycosylated. Therefore, additional techniques based on the lectin affnity chromatography can be utilized. Moreover, since the cDNAs have been isolated, a vector with affinity tag (Flag epitope, HA epitope, myc epitope, 6×His, maltose binding protein, chitinase, etc) can be constructed and the vector can be over-expressed in a suitable host, and then purified by anti-tag antibody-conjugated affinity chromatography.

A mammalian sialyltransferase nucleic acid (such as GM3-synthase or 4ST3Gal IV, 4ST3Gal VI, and 7STGal-NAc V), or fragment thereof, is a nucleic acid having a nucleotide sequence obtainable from a natural source. See, above. It therefore includes naturally-occurring, normal, naturally-occurring mutant, and naturally-occurring polymorphic alleles, etc. Natural sources include, e.g., living cells obtained from tissues and whole organisms, cultured cell lines, including primary and immortalized cell lines.

A nucleic acid sequence of the invention can contain the complete coding sequence as shown in FIGS. 1–6 (SEQ ID NOS:1–13), degenerate sequences thereof, and fragments thereof. A nucleic acid according to the present invention can also comprise a nucleotide sequence which is 100% complementary, e.g., an anti-sense, to any nucleotide sequence mentioned above and below.

A nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell or tissue (e.g., from an embryonic or adult heart or skeletal cells or tissues) at a particular stage of development, having a desired genotype, phenotype etc.

As described for the sialyltransferases mentioned above, a nucleic acid comprising a nucleotide sequence coding for a polypeptide according to the present invention can include only coding sequence; a coding sequence and additional coding sequence (e.g., sequences coding for leader, secretory, targeting, enzymatic, fluorescent or other diagnostic peptides), coding sequences and non-coding sequences, e.g., untranslated sequences at either a 5' or 3' end, or dispersed in the coding sequence, e.g., introns. A nucleic acid comprising a nucleotide sequence coding without interruption for a polypeptide means that the nucleotide sequence contains an amino acid coding sequence for a sialyltransferase, with no non-coding nucleotides interrupting or intervening in the coding sequence, e.g., absent intron(s). Such a nucleotide sequence can also be described as contiguous. A genomic DNA coding for a human, mouse, or other mammalian sialyltransferase, etc., can be obtained routinely. The nucleotide sequences of GM3 synthase ASF 400 and ASF 800 shown in FIG. 2 (SEQ ID NOS:5 and 6) and the nucleotide sequence of E8 in FIG. 5 (SEQ ID NOS:7 and 11) may play a regulatory role in the transcription, and/or translation of the sialytransferase protein, e.g., in targeting the mRNAs coding for the translated proteins to the appropriate intracellular compartment.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids, and their complements, which hybridize to a nucleic acid comprising a nucleotide sequence as set forth in FIGS. 1–6 (SEQ ID NOS:1–13). A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIGS. 1–6 (SEQ ID NOS:1–13). A nucleic acid capable of hybridizing to such sequence, preferably, possesses, e.g., about 85%, more preferably, 90%, 92%, and even more preferably, 95%, 97%, or 100% complementarity, between the sequences. The present invention particularly relates to nucleic acid sequences which hybridize to the nucleotide sequence set forth in FIGS. 1–6 (SEQ ID NOS:1–13) under low or high stringency conditions.

Nucleic acids which hybridize to sialyltransferases sequences can be selected in various ways. For instance, blots (i.e., matrices containing nucleic acid), chip arrays, and other matrices comprising nucleic acids of interest, can be incubated in a prehybridization solution (6×SSC, 0.5% SDS, 100 μg/ml denatured salmon sperm DNA, 5×Denhardt's solution, and 50% formamide), at 30° C., overnight, and then hybridized with a detectable oligonucleotides probe, (see below) in a hybridization solution (e.g., 6×SSC, 0.5% SDS, 100 μg/ml denatured salmon sperm DNA and 50% formamide), at 42° C., overnight in accordance with known procedures. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity. Other non-limiting examples of high stringency conditions includes a final wash at 65° C. in aqueous buffer containing 30 mM NaCl and 0.5% SDS. Another example of high stringent conditions is hybridization in 7% SDS, 0.5 M NaPO4, pH 7, 1 mM EDTA at 50° C., e.g., overnight, followed by one or more washes with a 1% SDS solution at 42° C.

Whereas high stringency washes can allow for less than 5% mismatch, relaxed or low stringency wash conditions (e.g., wash twice in 0.2% SSC and 0.5% SDS for 30 min at 37° C.) can permit up to 20% mismatch. Another non-limiting example of low stringency conditions includes a final wash at 42° C. in a buffer containing 30 mM NaCl and 0.5% SDS. Washing and hybridization can also be performed as described in Sambrook et al., Molecular Cloning, 1989, Chapter 9.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm= (number of A's and T's)×2° C.+(number of C's and G's)×4° C. For longer molecules, Tm=81.5+16.6 log 10[Na+]+0.41 (%GC)−600/N where [Na+] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 95%, preferably 97%, nucleotide complementarity between the probe (e.g., an oligonucleotide of a sialyltransferase and target nucleic acid.

According to the present invention, a nucleic acid or polypeptide can comprise one or more differences in the nucleotide or amino acid sequence set forth in FIGS. 1–6. Changes or modifications to the nucleotide and/or amino acid sequence can be accomplished by any method available, including directed or random mutagenesis.

A nucleic acid coding for a mammalian sialyltransferase according to the invention can comprise nucleotides which occur in a naturally-occurring gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtainable from a natural source, e.g., animal tissue and cells, body fluids, tissue culture cells, forensic samples. Naturally-occurring mutations can include deletions (e.g., a truncated amino- or carboxy-terminus), substitutions, inversions, or additions of nucleotide sequence These genes can be detected and isolated by nucleic acid hybridization according to methods which one skilled in the art would know. A nucleotide sequence coding for a mammalian sialyltransferase of the invention can contain codons found in a naturally-occurring gene, transcript, or cDNA, for example, e.g., as set forth in FIGS. 1–6, or it can contain degenerate codons coding for the same amino acid sequences. For instance, it may be desirable to change the codons in the sequence to optimize the sequence for expression in a desired host.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAase H, improved in vivo stability, etc. See, e.g., U.S. Pat. No. 5,378,825.

Various modifications can be made to the nucleic acids, such as attaching detectable markers (avidin, biotin, radio-active elements), moieties which improve hybridization, detection, or stability. The nucleic acids can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967; 5,476,925; 5,478,893.

Another aspect of the present invention relates to oligo-nucleotides or nucleic acid probes. Such oligonucleotides or nucleic acid probes can be used, e.g., to detect, quantitate, or isolate a mammalian sialyltransferase nucleic acid in a test sample, or to identify sialyltransferase homologs. In a preferred embodiment, the nucleic acids can be utilized as oligonucleotide probes, e.g., in PCR, differential display, in combination with cDNA libraries, expression libraries, etc. Detection can be desirable for a variety of different purposes, including research, diagnostic, and forensic. For diagnostic purposes, it may be desirable to identify the presence or quantity of a nucleic acid sequence in a sample, where the sample is obtained from tissue, cells, body fluids, etc. In a preferred method, the present invention relates to a method of detecting a nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR (e.g., Saiki et al., Science, 241:53, 1988; U.S. Pat. No. 4,683,202; PCR Protocols: A Guide to Methods and Applications, Innis et al., eds., Academic Press, New York, 1990); differential display (See, e.g., Liang et al., Nucl. Acid. Res., 21:3269–3275, 1993; U.S. Pat. No. 5,599,672; WO97/18454).

Detection can be accomplished in combination with oligonucleotides for other genes, e.g., genes involved in signal transduction, growth, cancer, apoptosis, or any of the genes mentioned above or below, etc. Oligonucleotides can also be used to test for mutations, e.g., using mismatch DNA repair technology as described in U.S. Pat. No. 5,683,877; U.S. Pat. No. 5,656,430; Wu et al., Proc. Natl. Acad. Sci., 89:8779–8783, 1992.

Oligonucleotides of the present invention can comprise any continuous nucleotide sequence of FIGS. 1–6 (SEQ ID NOS:1–13) or a complement thereto, or any of the sequences, or complements thereto, shown in Table 1(SEQ ID NOS:40–44, 49–52, 55, 56, 62–66, 69, 70, 73, 74, 80–84, 85, 86, 87 and 88). These oligonucleotides (nucleic acid) according to the present invention can be of any desired size, e.g., about 10–200 nucleotides, 12–100, preferably 12–50, 12–25, 14–16, at least about 15, at least about 20, etc. The oligonucleotides can have non-naturally-occurring nucleotides, e.g., inosine, AZT, 3TC, etc. The oligonucleotides can have 100% identity or complementarity to a sequence of FIGS. 1–6 (SEQ ID NOS:1–13), or it can have mismatches or nucleotide substitutions, e.g., 1, 2, 3, 4, or 5 substitutions. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Another aspect of the present invention is a nucleotide sequence which is unique to a mammalian sialyltransferase. By a unique sequence to a sialyltransferase, it is meant a defined order of nucleotides which occurs in sialyltransferase, e.g., in the nucleotide sequences of FIGS. 1–6 (SEQ ID NOS:1–13), but rarely or infrequently in other nucleic acids, especially not in an animal nucleic acid, preferably mammal, such as human, rat, mouse, etc. Unique nucleotide sequences include the sequences, or complements thereto, coding for amino acids as shown in Table 1 (SEQ ID NOS:40–44, 49–52, 55, 56, 62–66, 69, 70, 73, 74, 80–84, 85, 86, 87 and 88) and FIG. 9 (SEQ ID NOS:14–30). Such sequences can be used as probes in any of the methods described herein or incorporated by reference. Both sense and antisense nucleotide sequences are included. A unique nucleic acid according to the present invention can be determined routinely. A nucleic acid comprising such a unique sequence can be used as a hybridization probe to identify the presence of, e.g., human or mouse sialyltransferase, in a sample comprising a mixture of nucleic acids, e.g., on a Northern blot. Hybridization can be performed under high stringent conditions (see, above) to select nucleic acids (and their complements which can contain the coding sequence) having at least 95% identity (i.e., complementarity) to the probe, but less stringent conditions can also be used. A unique sialyltransferase nucleotide sequence can also be fused in-frame, at either its 5′ or 3′ end, to various nucleotide sequences as mentioned throughout the patent, including coding sequences for other parts of sialyltransferase, enzymes, GFP, etc, expression control sequences, etc.

As already discussed, hybridization can be performed under different conditions, depending on the desired selectivity, e.g., as described in Sambrook et al., Molecular Cloning, 1989. For example, to specifically detect human or mouse GM3 synthase, or any other sialyltransferase of the present invention, an oligonucleotide can be hybridized to a target nucleic acid under conditions in which the oligonucleotide only hybridizes to it, e.g., where the oligonucleotide is 100% complementary to the target. Different conditions can be used if it is desired to select target nucleic acids which have less than 100% nucleotide complementarity, at least about, e.g., 99%, 97%, 95%, 90%, 86.4%, 85%, 70%, 67%.

Antisense nucleic acid can also be prepared from a nucleic acid according to the present invention, preferably an anti-sense to a sequence of FIGS. 1–6 (SEQ ID NOS:1–13). Antisense nucleic acid can be used in various ways, such as to regulate or modulate expression of sialyltransferase, e.g., inhibit it, to detect its expression, or for in situ hybridization. These oligonucleotides can be used analogously to U.S. Pat. No. 5,576,208. For the purposes of regulating or modulating expression of sialyltransferase, an anti-sense oligonucleotide can be operably linked to an expression control sequence.

For the inhibition of human GM3 synthase, an oligonucleotide can be designed to the corresponding sense position along cDNA is 166–200 (CCTGCAATGGTACACCCGAGCTCAAAGCAAGATGA) (SEQ ID NO:31), or, with the respect to the initiating codon: −31–+4. A total length of about 35 bp can be used in cell culture with cationic liposomes to facilitate cellular uptake, but for in vivo use, preferably shorter oligonucleotides are administered, e.g. 25 nucleotides starting at 176 to 200 (−21 to+4), or 17 nucleotides starting at 184–200 (−13–+4). The sequence of corresponding antisense phosphorothioates: 34 nucleotides (antisense to −31–+4): 5′ TCATCTTGCTTTGAGCTCGGGTGTACCATTGCAGG (SEQ ID NO:32); 25 nucleotides (antisense to −21–+4): 5′ TCATCTTGCTTTGAGCTCGGGTGTA 3′ (SEQ ID NO:34); 17 nucleotides (antisense to −13–+4): 5′ TCATCTTGCTTTGAGCT 3′ (SEQ ID NO:34)

The nucleic acid according to the present invention can be labeled according to any desired method. The nucleic acid can be labeled using radioactive tracers such as 32P, 35S, 125I, 3H, or 14C, to mention some commonly used tracers. The radioactive labeling can be carried out according to any method such as, for example, terminal labeling at the 3′ or 5′ end using a radiolabeled nucleotide, polynucleotide kinase (with or without dephosphorylation with a phosphatase) or a ligase (depending on the end to be labeled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligonucleotides, anti-sense nucleic acid, etc., can be used to detect expression of sialyltransferase in whole organs, tissues, cells, etc., by various techniques, including Northern blot, PCR (see, Examples below for specific protocols), in situ hybridization, differential display, etc. Such nucleic acids can be particularly usefull to detect disturbed expression, e.g., cell-specific and/or subcellular alterations, of sialyltransferase. The levels of sialyltransferase can be determined alone or in combination with other gene products, especially other gene products involved in glycosylation.

A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. A nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a nucleic acid of the present invention has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells (e.g., COS, CV1, BHK, CHO, HeLa, LTK, NIH 3T3, 293, PAE, human, human fibroblast, human primary tumor cells, testes cells), insect cells, such as Sf9 (*S. frugipeda*) and Drosophila, bacteria, such as *E. coli*, Streptococcus, bacillus, yeast, such as Sacharomyces, *S. cerevisiae*, fungal cells, plant cells, embryonic stem cells (e.g., mammalian, such as mouse or human), fibroblasts, muscle cells, cardiac cells, T-cells (helper, CD4, CD8), B-cells, macrophages, hemopoietic cells, lymphocytes, Th1, Th2, etc.

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

Expression in a host cell of a heterologous sialyltransferase of the present invention is useful in variety of different purposes, e.g., to isolate the sialyltransferase, in engineering designer oligosaccharides, to modulate pathways in which sialyltransferases are active, e.g., cell growth, proliferation, differentiation, apoptosis, signal transduction, cell adhesion, etc.

Another gene of interest can be introduced into the same host for purposes of, e.g., modulating sialyltransferase expression, modulating glycosylation (e.g., to synthesize designer sialylated oligosaccharides), etc. Such genes can be the normal gene, or a variation thereof, e.g., a mutation, chimera, polymorphism, etc. Such genes include, e.g., members of the same or related pathways as mentioned above and below.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. A sialyltransferase as shown in FIGS. 1–6 and 9 can be used as a molecular weight marker in nucleic acid electrophoresis.

In general, the present invention relates to methods of regulating a biological response in which a sialyltransferase, or a homolog or modification thereof, of the present invention participates, e.g., by modifying a substrate, such as glycoprotein or glycolipid, which is a participant in a biochemical pathway which leads to the ultimate cellular response. These pathways can be modulated by administering various agents, including antibodies to sialyltransferases, polypeptide mimics of sialyltransferases (e.g., which compete for substrates of the enzyme), antisense oligonucleotides, antisense mRNA, etc.

Another aspect of the present invention relates to the regulation of glycosylation and the biological pathways in which glycosylated molecules participate. GM3 synthase is involved in the last step of GM3 biosynthesis. It catalyzes the transfer of a sialic acid moiety from CMP-sialic acid onto lactosylceramide, forming an α2–3 linkage. GM3 is a common precursor for nearly all of the naturally occurring gangliosides. GM3 and the products of GM3 metabolism have important functions in normal organism development as well as in pathogenesis. They have been implicated in modulation of cellular growth (2, 3), proliferation, differentiation (4–8), and apoptosis (9). The modulatory role of GM3 and its metabolites, such as lyso-GM3 and deNAcGM3, in signal transduction (10) has been shown to be mediated through growth factor- or hormone receptor-associated cytoplasmic protein kinases (11–15), protein tyrosine phosphatase (16), protein kinase C (PKC) (14, 17–19), phospholipase C (PLC) δ1 (20), and $Ca^{2+}$-ATPase (21). In addition, a close association has been reported of transducer proteins (c-Src, Ras, FAK, Rho A, H-Ras) and neurotrophic factors such as prosaposin (22) with GM3 in the cell surface microdomains, suggesting a functional association (23). GM3 has also been reported to interact with other glycosphingolipids, such as LacCer and Gg3, to provide adhesion of melanoma cells onto endothelial cells (24, 25) and function as a fusion co-factor for HIV-1 and HIV-2 (26, 27). By inhibiting or enhancing GM3 synthase activity (e.g., by blocking expression of the corresponding gene, or, increasing gene expression gene by gene dosage or by operably linking the gene to a highly active promoter), any of the aforementioned processes can be modulated and/or treated.

The present invention also relates to methods of glycosylating substrates by contacting a sialyltransferase of the present invention with a suitable sialic acid substrate acceptor and a sialic acid donor. In preferred embodiments, the present invention relates to a method of transferring a sialic acid from a sialic acid donor to a sialic acid acceptor substrate (i.e., glycosylation) comprising: contacting a human or mouse GM3 synthase, human or mouse 4ST3GalVI, or human 7STGalNAcV sialyltransferase, or biologically-active fragments thereof, with a sialic acid acceptor substrate and sialic acid donor under conditions effective for transfer of a sialic acid from a donor molecule to the acceptor substrate. Such a method can be useful in variety of ways. It can be useful for determining whether a particular compound is capable of acting as a sialic acid donor or substrate acceptor for a sialyltransferase. The method can also be used to design and engineer molecules, such as glycolipids or glycoproteins, to contain specific sugar residues. As mentioned, siallytransferases are known to have specific activity in the type of sugar residue added, the kind of bond formed, and the acceptor molecule utilized (e.g., a galactose, a glucose, a glucosamine, etc.). By selecting the sialyltransferase, a glycoprotein can be selectively engineered to incorporate specific sugar residues at specific positions of the molecule. For instance, a glycoprotein or protein can be treated with one or more sialyltransferase to design a final glycoprotein. The glycoprotein can be subjected to one or more steps of glycosylation, either sequentially, all-at-once, or a combination thereof. For example, N-linked glycosylation is typically initiated by the transfer of a core region oligosaccharide (N-acetylglucoasamine, mannose, and glucose) from dolichol to the nitrogen atom of an asparagine residue of a target polypeptide. This reaction is catalyzed by glycosyl transferase. In subsequent steps, e.g., occurring in the golgi apparatus of intact cells, the "core-region" oligosaccharide is modified by the step-wise deletion or addition of sugar residues to finish the synthesis of complex and high mannose oligosaccharides. Various enzymes are used in these processing steps, including, e.g., glucosidase I and II, ER mannidase, Golgi mannidase I and II, N-acetylglucosamines, etc. To engineer specific linkages, one or more these enzymes, in combination with sialyltransferases, can be combined with acceptor molecules and donor molecules under effective conditions. For example, an artificial ST donor, such as ManLev (keto group at some point along the carbon chain) can be converted by a cell into modified CMP-sialic acid which can then, in turn, get incorporated into cell surface lipids and proteins.

The sialyltransferase can be "isolated" or it can be present as an expression product of a heterologous gene in a transfected cell line. By the term"isolated," it is meant that sialyltransferase is in a form in which it is not found in its original environment or in nature, e.g., more concentrated, more purified, separated from components, present in a lysate of a cell in which a heterologous sialyltransferase gene is expressed. When the sialyltransferase is expressed as a heterologous gene in a transfected cell line, a gene in accordance with the present invention is introduced into a cell as described above, under conditions in which the gene is expressed. The term "heterologous" means that the gene has been introduced into the cell line by the "hand-of-man." Introduction of a gene into a cell line is discussed above. The transfected (or transformed) cell expressing the sialyltransferase gene can be lysed as described in the examples and used in the method as a lysate (i.e., "isolated") or the cell line can be used intact. Such a transfected cell can contain one or more heterologous sialyltransferases.

Any suitable substrate acceptor and donor can be used in the assay. For instance, if an isolated GM3 synthase is utilized, various acceptor glycolipids can be used, such as GM1, GD1a, GM3, or LacCer, N-glycolylneuraminic acid (CMP-Neu5Gc), and ketodeoxynonulosonic acid (KDN) with glycol or hydroxyl group of carbons. Useful sialic acid donors include, e.g., CMP-N-[14C]acetylneuraminic acid. The sialyltransferase is contacted with the donor and substrate under effective conditions.

Generally, the term "effective conditions" means, e.g., a milieu in which the desired effect is achieved. Such a milieu, includes, e.g., buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.).

Detecting sialic transfer can be accomplished conventionally, e.g., as described in the examples using radioactive molecules.

The present invention also relates to a method of modulating, preferably inhibiting, expression of a gene coding for a sialyltransferase, comprising: contacting a cell expressing a sialyltransferase of the present invention, such as a human or mouse GM3 synthase, human or mouse 4ST3GalVI, or human 7STGalNAcV sialyltransferase, with an amount of agent, such as an antisense oligonucleotide or antisense RNA of a human or mouse GM3 synthase, human or mouse 4ST3GalVI, or human 7STGalNAcV sialyltransferase gene, which is effective to sequence-specifically inhibit said gene. Inhibiting expression of a sialyltransferase gene can inhibit the maturation of oligosaccharides in the pathway, and have consequent impact on the pathways in which such oligosaccharides are involved, including those mentioned above. For instance, inhibiting ST expression can be useful to inhibit tumor growth and metastasis and therefore can be used used to treat cancer. More generally, inhibition of ST gene expression can be used to inhibit cell adhesion, movement, etc., especially in pathological conditions where inhibition of such activity is desirable.

Sequence-specific inhibition of a gene can be accomplished conventionally using antisense nucleic acid, such as antisense oligonucleotides or RNA. For example, antisense oligonucleotides, such as phosphodiester or phosphorothioate deoxyoligonucleotides can be designed to specific regions of a sialyltransferase RNA, such as to the translation initiation site, and can then be administered to cells expressing such genes in quantities effective to inhibit their expression. Generally, an antisense nucleic acid is a nucleic acid which is complementary to the sense or coding strand of a given gene, and as a result are also complementary and thus able to specifically hybridize with niRNA transcripts of the gene. Preferred anitsense oligonucleotiodes comprise the 5' region of a target gene, especially the region containing the initiation codon.

To enhance stability, the administered nucleic acid can be modified, e.g., to make it resistant to cellular enzymes, oxidation, reduction, nucleases, etc, or to enhance its uptake into cells. Any suitable modification can be used, including, e.g., phosporothioates, methylphosphonates, phosphodiester oligonucleotide linked to an acridine intercalating agent and/or a hydrophobic tail, psoralen derivatives, 2'-ribose modifications, pentose sugar derivatives, nitrogen base derivatives, etc. See, e.g., U.S. Pat. No. 5,576,208 and U.S. Pat. No. 5,744,362. See, above, for other derivatives, modifications, etc. which can be useful in the invention. In general, an antisense nucleic acid of the present invention can comprise monomers of naturally-occurring nucleotides, non-naturally-occurring nucleotides, and combinations thereof to enhance cellular uptake and/or stability.

Antisense can be administered as naked nucleic acid, complexed or encapsulated with and by other agents which facilitate its uptake into a cell, injected into cells, or any suitable delivery means.

The present invention also relates to a method combinatorial PCR (polymerase chain reaction) comprising, for example, contacting a sample comprising nucleic acid with a forward PCR primer and a reverse PCR primer under conditions effective to amplify a segment of nucleic acid in said sample, wherein the forward PCR primer or the reverse PCR primer, or both, is a combinatorial PCR primer. A combinatorial PCR primer is a set (i.e., more than one single primer sequence) of PCR primers which are based on a polypeptide motif derived from the comparison of at least two different proteins, preferably three or more. A combinatorial primer is designed by a combinatorial calculation which deals with questions such as, "if you have three different gold coins, two silver, and six bronze, how many combinations of different metals can you create?" Answer: 3×2×6. Or, "if you have six different coins and six different pockets, in how many ways can you place them in your pockets?"Answer: 6!. Combinatorial PCR is accounting for all possible variations in a motif, using all possible forward and reverse primers and a set of cDNA libraries or any other suitable nucleic acid sample (e.g., genomic library or DNA) as a template. For instance, where the amino acid sequences in polypeptide motif at the amino-terminus is ABCD and ABED, the combinatorial primer is ABCD and ABED. For another motif at the carboxy-terminus where the particular amino acid sequences are FGHI, FGHJ, and FGKI, the combinatorial primers is FGHI, FGHJ, FGKI, and FGHJ. Apart from the actual sequences in the motif, potentially homologous substitutions could be included as well, e .g., valine could be potentially substituted for leucine, serine for threonine, etc. The examples below illustrate how combinatorial PCR can be used for cloning sialytransferases.

The present invention relates to a method of detecting sialyltransferase activity or donor-binding activity in a sialyltransferase, or a biologically-active polypeptide fragment thereof. Detection of one or more of these activities can be accomplished in any suitable way, including in vitro, in vivo, or combinations thereof. For example, sialyltransferase assays can be carried out as known in the art. Typically, a method of detecting sialyltransferase comprises, reacting a sialyltransferase polypeptide, or a biologically-active polypeptide fragment thereof, and a substrate under conditions effective for said sialyltransferase polypeptide to add a sialic acid to an acceptor molecule. Assays can be carried out as described in, e.g., U.S. Pat. No. 5,494,790; U.S. Pat. No. 5,409,817; WO 97/47749; Ma et al., *J. Biol. Chem.* 272:672–679 (1997).

The present invention also relates to methods of identifying substrates for sialyltransferase activity. Sialyltransferase can be contacted with a test substrate, either in vivo or in vitro, under conditions effective for sialyltransferase to occur.

Generally, the term "effective conditions" means, e.g., a milieu in which the desired effect is achieved. Such a milieu, includes, e.g., buffers, oxidizing agents, reducing agents, pH, co-factors, temperature, ion concentrations, suitable age and/or stage of cell (such as, in particular part of the cell cycle, or at a particular developmental stage where particular genes are being expressed) where cells are being used, culture conditions (including substrate, oxygen, carbon dioxide, etc.).

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

The term "administering" as used herein, means, e.g., any suitable delivery technique which is adequate to place the agent in a location where it can elicit an effect. For example, administering can mean contacting a cell or host in an effective manner with the agent of interest, whereby the agent can modulate the activity of interest. Thus, the agent can be administered: in liposomes, as a nucleic acid, in combination with a polymer, in encapsulating agents, in a suitable carrier, etc.

The present invention also relates to antibodies which specifically recognize sialyltransferase. An antibody specific for sialyltransferase means that the antibody recognizes a defined sequence of amino acids within or including a sialyltransferase, e.g., the human sequence of FIG. 1. Thus, a specific antibody will generally bind with higher affinity to an amino acid sequence, i.e., an epitope, found in FIGS. 1–6 and 9 than to a different epitope(s), e.g., as detected and/or measured by an immunoblot assay or other conventional immunoassay. Thus, an antibody which is specific for an epitope of human sialyltransferase is useful to detect the presence of the epitope in a sample, e.g., a sample of tissue containing human sialyltransferase gene product, distinguishing it from samples in which the epitope is absent. Such antibodies are useful as described in Santa Cruz Biotechnology, Inc., Research Product Catalog, and can be formulated accordingly.

Antibodies, e.g., polyclonal, monoclonal, recombinant, chimeric, humanized, can be prepared according to any desired method. See, also, screening recombinant immunoglobulin libraries (Orlandi et al., Proc. Natl. Acad. Sci., 86:3833–3837, 1989; Huse et al., Science, 256:1275–1281, 1989); in vitro stimulation of lymphocyte populations; Winter and Milstein, Nature, 349: 293–299, 1991. For example, for the production of monoclonal antibodies, a polypeptide according to FIGS. 1–6 and 9 can be administered to mice, goats, or rabbit subcutaneously and/or intraperitoneally, with or without adjuvant, in an amount effective to elicit an immune response. The antibodies can also be single chain or FAb fragments. The antibodies can be IgG, subtypes, IgG2a, IgG1, etc. Antibodies, and immune responses, can also be generated by administering naked DNA See, e.g., U.S. Pat. Nos. 5,703,055; 5,589,466; 5,580,859.

Sialyltransferase, or fragments thereof, for use in the induction of antibodies do not need to have biological activity; however, they must have immunogenic activity, either alone or in combination with a carrier. Peptides for use in the induction of sialyltransferase-specific antibodies may have an amino sequence consisting of at least five amino acids, preferably at least 10 amino acids. Short stretches of sialyltransferase amino acids, e.g., five amino acids, can be fused with those of another protein such as keyhole limpet hemocyanin, or another useful carrier, and the chimeric molecule used for antibody production.

Several different approaches, as mentioned, can be utilized to prepare antibodies specific for sialyltransferase. For instance, in one approach, denatured sialyltransferase from purified sialyltransferase (e.g., purified by reverse-phase HPLC separation) is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In another approach, an amino acid sequence of sialyltransferase, as deduced from the cDNA, is analyzed to determine regions of high immunogenicity. Polypeptides comprising these regions are synthesized and used in suitable immunization protocols to raise antibodies. Analysis to select appropriate epitopes is described by Ausubel FM et al (1989, Current Protocols in Molecular Biology, Vol 2. John Wiley & Sons). The optimal amino acid sequences for immunization are usually at the C-terminus, the N-terminus and those intervening, hydrophilic regions of the polypeptide which are likely to be exposed to the external environment when the protein is in its natural conformation. Typically, selected peptides, about 15 residues in length, are synthesized using an Applied Biosystems Peptide Synthesizer Model 431A using finoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas can also be prepared and screened using standard techniques. Hybridomas of interest are detected by screening with labeled sialyltransferase to identify those fusions producing the monoclonal antibody with the desired specificity. In a typical protocol, wells of plates (FAST, Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled sialyltransferase, 1 mg/ml. Clones producing antibodies will bind a quantity of labeled sialyltransferase which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ M, preferably $10^9$ to $10^{10}$, or stronger, will typically be made by standard procedures as described in Harlow and Lane (1988) Antibodies: A Laboratory Manual. Cold Spring Harbor Laboratory, or Goding (1986) Monoclonal Antibodies: Principles and Practice, 2nd Ed. Academic Press N.Y.

Useful sequences for generating antibodies, include, the aligned sequences shown in FIG. 9. Antibodies to such sequences can be useful for distinguishing between the different transcripts of sialyltransferase. See, above.

Particular sialyltransferase antibodies are useful for the diagnosis of prepathologic conditions, and chronic or acute diseases which are characterized by differences in the amount or distribution of sialyltransferase. Diagnostic tests for sialyltransferase include methods utilizing the antibody and a label to detect sialyltransferase in human (or mouse, etc, if using mouse, etc.) body fluids, tissues or extracts of such tissues.

The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound sialyltransferase, using either polyclonal or monoclonal antibodies specific for sialyltransferase are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EC is preferred, but a competitive binding assay may be employed. These assays are described, among other places, in Maddox, Del. et al (1983) J Exp Med 158: 1211.

Antibodies and other ligands which bind sialyltransferase can be used in various ways, including as therapeutic, diagnostic, and commercial research tools, e.g., to quantitate the levels of sialyltransferase polypeptide in animals, tissues, cells, etc., to identify the cellular localization and/or distribution of it, to purify it, or a polypeptide comprising a part of it, to modulate the function of it, in Western blots, ELIZA, immunoprecipitation, RIA, etc. The present invention relates to such assays, compositions and kits for performing them, etc. Utilizing these and other methods, an antibody according to the present invention can be used to detect sialyltransferase polypeptide or fragments thereof in various samples, including tissue, cells, body fluid, blood, urine, cerebrospinal fluid.

Native or recombinant sialyltransferase can be purified by immunoaffinity chromatography using sialyltransferase-specific antibodies. In general, an immunoaffinity column is constructed by covalently coupling the anti-sialyltransferase antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified Ig is covalently attached to a chromatographic resin such as CnBr activated Sepharose (Pharmacia LKB Biotechnology, Piscataway, N.J.). The antibody is coupled to the resin, the resin is blocked, and the derivative resin is washed according to the manufacturer's instructions.

An immunoaffinity column is utilized in the purification of sialyltransferase by preparing a fraction from cells containing sialyltransferase. This preparation can be derived by solubilization of the whole cell or of a subcellular fraction obtained via differential centrifugation by the addition of detergent or by other methods well known in the art. Alternatively, soluble sialyltransferase containing a signal sequence may be secreted in useful quantity into the medium in which the cells are grown.

A soluble sialyltransferase-containing preparation is passed over the immunoaffinity column, and the column is washed under conditions, e.g., high ionic strength buffers in the presence of detergent, that allow the preferential absorbance of sialyltransferase. Then, the column is eluted under conditions that disrupt antibodylsialyltransferase binding (e.g., a buffer of pH 2–3 or a high concentration of a chaotrope such as urea or thiocyanate ion), and the sialyltransferase is collected.

In addition, ligands which bind to a sialyltransferase polypeptide according to the present invention, or a derivative thereof, can also be prepared, e.g., using synthetic peptide libraries or aptamers (e.g., Pitrung et al., U.S. Pat. No. 5,143,854; Geysen et al., J. Immunol. Methods, 102:259–274, 1987; Scott et al., Science, 249:386, 1990; Blackwell et al., Science, 250:1104, 1990; Tuerk et al., 1990, Science, 249: 505.).

The antibodies or derivatives thereof can also be used to inhibit expression of sialyltransferase or a fragment thereof. The levels of sialyltransferase polypeptide can be determined alone or in combination with other gene products. In particular, the amount (e.g., its expression level) of sialyltransferase polypeptide can be compared (e.g., as a ratio) to the amounts of other polypeptides in the same or different sample, e.g., actin. In general, reagents which are specific for sialyltransferase can be used in diagnostic and/or forensic studies according to any desired method, e.g., as U.S. Pat. Nos. 5,397,712; 5,434,050; 5,429,947.

The present invention also relates to a sialyltransferase polypeptide, prepared according to a desired method, e.g., as disclosed in U.S. Pat. No. 5,434,050. A labeled polypeptide can be used, e.g., in binding assays, such as to identify substances that bind or attach to sialyltransferase, to track the movement of sialyltransferase in a cell, in an in vitro, in vivo, or in situ system, etc.

A nucleic acid, polypeptide, antibody, sialyltransferase, ligand etc., according to the present invention can be isolated. The term "isolated" means that the material is in a form in which it is not found in its original environment or in nature, e.g., more concentrated, more purified, separated from component, etc. An isolated nucleic acid includes, e.g., a nucleic acid having the sequence of sialyltransferase separated from the chromosomal DNA found in a living animal, e.g., as the complete gene, a transcript, or a cDNA. This nucleic acid can be part of a vector or inserted into a chromosome (by specific gene-targeting or by random integration at a position other than its normal position) and still be isolated in that it is not in a form which it is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a sialyltransferase. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993. A nucleic acid according to the present invention can be introduced into any non-human mammal, including a mouse (Hogan et al., Manipulating the Mouse Embryo: A Laboratory Manual, Cold Spring Harbor Laboratory, Cold Spring Harbor, N.Y., 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988). In addition, e.g., custom transgenic rat and mouse production is commercially available. These transgenic animals can useful animals models to test for sialyltransferase function, as food for a snake, as a genetic marker to detect strain origin (i.e., where a sialyltransferase or fragment thereof has been inserted), etc. Such transgenic animals can further comprise other transgenes. Transgenic animals (such as sialyltransferase knockouts) can be prepared and used according to any suitable method. A transgenic animal containing a sialyltransferase mutant (e.g., a dominant interfering sialyltransferase) or a sialyltransferase knockout can be combined with other gene mutations, e.g., knockouts or mutations in genes involved in the same or similar pathway. Such genes include: various sialytransferases, glycosidases, ST8Sia I, and other transferases, e.g., the sialyltransferases of FIG. 9, and any genes mentioned above, below, or in the references incorporated herein, etc. Animals can be homozygous or heterozygous, depending on the desired use and phenotype.

Generally, the nucleic acids, polypeptides, antibodies, etc. of the present invention can be prepared and used as described in, U.S. Pat. Nos. 5,501,969, 5,506,133, 5,441, 870; WO 90/00607; WO 91/15582.

For other aspects of the nucleic acids, reference is made to standard textbooks of molecular biology. See, e.g., Davis et al., Basic Methods in Molecular Biology, Elsevir Sciences Publishing, Inc., New York, 1986; Hames et al., Nucleic Acid Hybridization, IL Press, 1985; Sambrook et al., Molecular Cloning, CSH Press, 1989; Howe, Gene Cloning and Manipulation, Cambridge University Press, 1995.

EXAMPLES

Example 1

Cloning of Sialytransferase

In general, three approaches are used for the cloning of the cDNA coding for a specific sialyltransferase: a) protein purification followed by protein sequencing and cDNA library screening (28, 29) b) expression cloning (30, 31) c) direct cDNA cloning with degenerate primers designed based on the most conserved area of homology between family members (32–34). In this report, we improved the direct cDNA cloning approach by utilizing 1) degenerate primers designed to accommodate the variations in the entire conserved pattern (similar amino acid sequences present in different family members) as well as possible homologous substitutions and then utilizing different combinations of these primers in PCR; 2) a panel of cDNA libraries as a template, which assures complete representation of differentially expressed and tissue-specific sialyltransferases; 3) a pooled cDNA library as a template in the 96-well thermoplate, which assures amplification of cDNA for low-abundance sialyltransferases with less than perfect homology with the primers; 4) polyacrylamide gel with an alternative cross-linker to assure complete separation of PCR products that differ only a few bases in length; 5) a step-down PCR protocol and PCR with nested primers to increase the specificity of the reaction; 6) the primers for a new sialylmotif, which we termed STP (sialylmotif petit) and which is probably implicated in the recognition of the nucleotide portion of CMP-sialic acid (see below).

MATERIALS AND METHODS

1. Materials

The NG108-15 cell line, a hybrid of murine neuroblastoma and rat glioma cells, was kindly provided by Dr. Robert Ledeen (New Jersey School of Medicine, Newark, N.J.). P19 embryonal carcinoma cell line was purchased from ATCC (ATCC #CRL 1825, ATCC, Manassas, Va.). The human fetal glioma cell line, N-370 FG, was kindly provided by Dr. Toshio Ariga (Medical College of Virginia, Richmond, Va.). Dulbecco's modified Eagle's medium (DMEM) was obtained from GibcoBRL (Grand Island, N.Y.). Tissue culture dishes were from Falcon/Becton Dickinson Co. (Franklin Lakes, N.J., USA) and high-performance thin-layer chromatographic (HPTLC) plates were from Merck (Darmstadt, Germany). Mouse multiple tissue cDNA (MTC™) panel (#K1423-1) and human fetal MTC™ panel (#K1425-1) were purchased from Clontech (Clontech Laboratories, Inc., Palo Alto, Calif.). SuperScript™ human fetal brain (#10662-013) and mouse 15.5 day embryo (#10667-012) plasmid cDNA library were purchased from Life Technologies (Gaithersburg, Md.). All other chemicals were of analytical grade or higher, and solvents were freshly redistilled before use.

2. Primers

In ST cloning, we took advantage of a STP motif (35) in addition to the well-known STL and STS motifs (FIG. 9) (SEQ ID NOS:14–30). The conserved motifs for ST3 sialyltransferases used in the primer design along with amino acid variations considered in the primer design, are shown in FIG. 9A and Table 1. Based on homology analysis, we subdivided the ST families (1) into 7 subfamilies (35) to facilitate primer design. In this classification, the ST3 family was divided into 2 subfamilies: 4 and 5. Forward primers 1F (a–d) were designed based on a portion of the STL motif, with variations to accommodate all of its amino acid substitutions, and possible homologous substitutions such as K↔R, known for other STs, V↔I, and V↔A (35). In the amino acid sequences for the design of forward primers 2F(a, b), G was substituted for S, and the second G residue substituted for H according to the variations in the motif. Combinations of these substitutions were used in the design of the primers 2F(c, d). In the sequence for the 3F primers, S was substituted for N according to the pattern for family 4 of ST3. A broader range of substitutions, L↔M and V↔T, was used in other experiments. In the amino acid sequence for the primers 4F, F↔T and S↔G substitutions were used according to the motif, and their combinations were used in the design of the primers 4Fd and 4Fe. A↔Y substitutions were used in the design of 1R primers according to the motif and their combination was used in other experiments. N↔H and Y↔F substitutions were used according to the motif for ST3 family in the design of 2Ra and 2Rb primers. Additional Y↔L and A↔(Y/F) substitutions were used in other experiments. For the primers designed based on the STP motif, Y↔W↔F and D↔E substitutions were used in different combinations (FIG. 9 (SEQ ID NOS:14–30), Table 1).

To assure amplification of cDNA for all ST family members, different combinations of forward and reverse primers were used in the combinatorial PCR approach along with a panel of mouse and human cDNAs as templates. Using a panel of cDNAs as a template provided additional information about tissue- and stage-specific expression of the particular ST. In order to compensate for possible underamplification of homologous STs due to the lower degree of homology with the designed primers, pooled human fetal brain and mouse total embryo cDNA plasmid libraries with a pool size of 2,000 independent colonies were screened. This pool size provided representation of no more than one sialyltransferase in most of the pools, thus assuring adequate and specific amplification when the template exhibit sub-optimal homology to the primers.

3. Library amplification

A set of 12 96-well flat-bottom tissue culture plates were inoculated at a density of 2,000 clones/well with mouse or human SuperScript cDNA plasmid libraries in 0.3 ml of Terrific Broth (TB) containing ampicillin (100 $\mu$g/ml) and carbenicillin (50 $\mu$g/ml). The library was amplified for 24 hr at 30° C., and 20 $\mu$l aliquots from each well of a particular row were combined into one well of a master plate so that row A of the first plate became well 1A of a master plate, row B became 1B, and so forth. An aliquots of 0.75 ml of TB media with the antibiotics in 1.2 ml cluster tubes (Costar Corp., Cambridge, Mass.) were inoculated with 20 $\mu$l of the combined pools of the master plate, and cells were collected by centrifugation at 1,600 g for 5 min. Plasmid DNA was isolated following the standard alkaline lysis procedure with 70 $\mu$l of solubilization, denaturing, and neutralization buffer, and then precipitated with 150 $\mu$l of isopropanol in 96-well U-shape tissue culture plates (Coster Corp., Cambridge, Mass.). Following centrifugation at 1600 g the resulting DNA pellet was redissolved in 150 $\mu$l of water.

4. cDNA Synthesis

Isolation of mRNA from human N-370 FG, HeLa, or differentiated mouse P19 cells was achieved by using PolyATrace$^R$ system III (Pomega, Madison, Wis.). The sample was reverse-transcribed using 10 pmols of STP-R (a,b,c,d,e) primers (separately or as a mixture) and SuperScript™ reverse transcriptase.

5. PCR

For PCR with cDNA panels as a template (12 reactions for the mouse or 8 for the human panel, multiplied by the number of different primer combinations in the primary PCR reaction), 1 nmol of each primer, 100 $\mu$l of 10×Taq polymerase buffer [final concentration: 20 mM Tris sulfate, 3.5 mM MgSO$_4$, 16 mM (NH$_4$)2SO$_4$, and 150 $\mu$g/ml of BSA, which was omitted if silver staining was used], 20 $\mu$l of 10 mM dNTP mix, 10 U of Taq polymerase, and 0.5 $\mu$l of the template were combined and brought with water to the final volume of 1 ml. Aliquotes of 10 $\mu$l of this mix were transferred into each of the 96 wells of a Thermowell plate (07-200-248, Fisher Scientific, Pittsburgh, Pa.), combined with 0.5 $\mu$l of a template DNA, and overlaied with mineral oil. Following initial denaturation at 95° for 1 min, the reaction was allowed to proceed for 43 cycles at 95° C. for 20 sec, 62° C. for 30 sec, and 68° C. for 45 sec. During the first seven cycles, the annealing temperature was decreased 1° C. per cycle. When the annealing temperature reached 54° C., the reaction was allowed to proceed for an additional 35 cycles. The final extension was performed at 72° C. for 10 min. An aliquot of 0.5 $\mu$l of the primary PCR reaction mixture was reamplified with the internal set of primers following the same PCR profile. The volume per reaction in the secondary PCR was increased to 20 $\mu$l, and all the components of the reaction mixture were increased correspondingly. For the PCR with a pooled cDNA library, the same reaction mixture was used with 1 $\mu$l of the template and the same PCR profile with a starting annealing temperature of 65° C. and a final annealing temperature of 59° C. for the last 35 cycles. The higher annealing temperature was necessary to decrease nonspecific priming on the vector itself. In primary PCR with STP primers the starting and final annealing temperatures were decreased by 4° C. The PCR products were separated by agarose or, if reamplification was necessary, by polyacrylamide gel electrophoresis. In order to verify the specificity of PCR, Southern hybridization analysis was performed with the random primer-labeled fragments spanning the amplified areas of several known sialyltransferases.

6. Sequencing The sequencing reaction was performed using a BigDye™ dye-terminators sequencing kit following the manufacturer's instructions with the exception that the volumes of the reagents used were proportionally decreased so that 0.5 μg of plasmid DNA was combined with 1.5 μl of terminators mix instead of 8 μl and 5 pmols of the primer. Products of the sequencing reaction were separated on an ABI PRISM™ 377 analyzer.

7. Library Screening

Gene-specific primers were synthesized using the sequencing information, and a second round of screening was then performed using the DNA sample from the primary plates as a template. Since each well of the master plate corresponds to a single row on a particular primary plate, an aliquot of bacterial suspension from each well of the positive rows (the row corresponding to the well from the master plate that produced a positive signal in the first round of PCR) was analyzed in the second round of PCR. Bacterial cells from the positive well of the primary plate were plated on a Nylon filter at the density of 10,000 colonies/150 mm plate. A replica filter was then prepared. Following denaturation at 70° C. in 0.5 M NaOH for 10 min with subsequent neutralization in 1 M Tris-HCl, pH 7.0, the replica filter was hybridized with $1 \times 10^6$ cpu/ml of hybridization buffer (50 mM Tris-HCl, pH 7.0 at 60° C., 1 M NaCl, 1% SDS, 10% dextran sulphate MW 400,000, and 100 μg/ml denatured shredded salmon sperm DNA) for 4 hrs, washed four times in 1% SDS, 1×SSC buffer at 60° C. and exposed to an X-ray film for 10 to 30 min. Plasmid DNA from the positive clones was further sequenced. The primer design for the primer walking was assisted by the Prime program (Genetic Computer Group, Madison, Wis.) and EST database analysis.

8. Cell Culture and Transfection NG108-15 cells were propagated in DMEM, supplemented with 10% fetal calf serum in a humidified atmosphere at 5% $CO_2$. Cells were transfected with pFLAG-CMV-5 ST-I vectors following a lipofectamine transfection protocol (Life Technologies, Gaithersburg, Md.) and harvested following 48 hours of incubation. pCMV-Sport 2 plasmid containing ST-I cDNA with N-terminal deletion was used as a control.

9. Enzyme Assay

Transfected cells corresponding to 10 mg of cell mass were incubated with 100 μl of enzyme assay buffer (25 mM sodium cacodylate, pH 6.5, 10 MM $MgCl_2$, 0.3% Triton CF-54) for 30 min at 4° C. Any insoluble material was removed by centrifugation at 14,000 g for 5 min, and aliquots of 20 μl corresponding to approximately 150 μg of solubilized protein were taken from the supernatant for determination of enzyme activity. The aliquots were added to 80 μl of enzyme assay buffer supplemented with 40 nmoles of CMP-N-[$^{14}$C]acetylneuraminic acid (0.20 μCi) and 20 moles of an acceptor glycolipid (GM1, GD1a, GM3, or LacCer). After incubation for 2 hrs at 37° C., the incubation mixture was subjected to gel chromatography on Sephadex G-50, supplemented with 400 μl of water and 500 μl of $CHCl_3/CH_3OH/H_2O$(8:4:3 by volume) for Folch-extraction of the assay product [$^{14}$C]-GM3. The incorporated radioactivity was determined by liquid scintillation counting of the Sephadex G-50 eluate as described elsewhere (36) or by HPTLC of the Folch extract in $CHCl_3/CH_3OH/0.2\%$ aq. $CaCl_2$ (50:45:10 by volume), followed by autoradiography of the developed chromatogram. Blank assays were performed with the heat-inactivated enzyme.

RESULTS AND DISCUSSION

We describe an approach that we developed for homology-based PCR cloning. In this approach, protein sequences of all homologous members of an enzyme family (ST in this paper) were aligned, and amino acid motifs were generated based on the conserved areas of homology. Forward and reverse degenerate primers were designed so that most variations of amino acid residues were included in the motif and potential conserved substitutions. All possible combinations of forward and reverse primers were then used in the PCR with a panel of cDNAs from different tissues and different organisms (mouse and human in this paper), thus providing amplification of tissue-specific and developmentally regulated enzymes.

For cloning GM3-synthase, an aliquot of each cDNA panel was amplified by a primary PCR with the following combinations of primers (Table 1): 1Fa-1Ra, 1Fb-1Ra, 1Fc-1Ra, 1Fd-1Ra, 1Fe-1Ra; 1F(a,b,c,d,e)-1Rb; followed by the secondary PCR with 2Fa-2Ra, 2Fb-2Ra, 2Fa-2Rb, 2Fb-2Rb; 3F(a,b)-2R(a,b); 4F(a,b)-2R(a,b). The primary with 2F(a,b)-1R(a,b) combinations of primers was followed by the secondary PCR with 3F(a,b)-2R(a,b) and 4F(a,b)-2R(a,b) combinations of primers. The primary PCR with 3F(a,b)-1R(a,b) combinations of primers was followed by the secondary PCR with 4F(a,b)-2R(a,b) combinations of primers. The position of amino acid residues used for the design of primers is shown in FIG. 9 (SEQ ID NOS:14–30). Gel-purified PCR products were cloned and sequenced. Since we employed mouse and human panels, it was possible to isolate both mouse and human copies of a particular ST. Mouse and human sialyltransferases were considered functionally identical if the percentage of homology in the coding region was higher then 80% on a cDNA level. If neither mouse nor human homolog was found, we designed degenerate primers based on a specific amino acid sequence in the STL or STS rather than on an entire motif, and we rescreened the pooled cDNA library by PCR. In addition, standard library screening was performed with either a mouse or a human counterpart as a probe. Based on the sequence of PCR products, gene-specific primers were designed, and pooled cDNA library was screened again. Positive pools were plated and screened with PCR product as a probe to isolate full-length cDNA.

The expression pattern across the panel of tissues provided information about the tissue-specificity of the particular ST expression. Since GM3 is synthesized in all tissues, we cloned two different STs that are ubiquitously expressed in mouse and human tissues. Owing to their closer homology to ST3 Gal III sialyltransferase, one of these STs was termed ST3Gal V and the other one termed ST3Gal VI because it showed a higher homology to ST3Gal IV.

Figure 8:
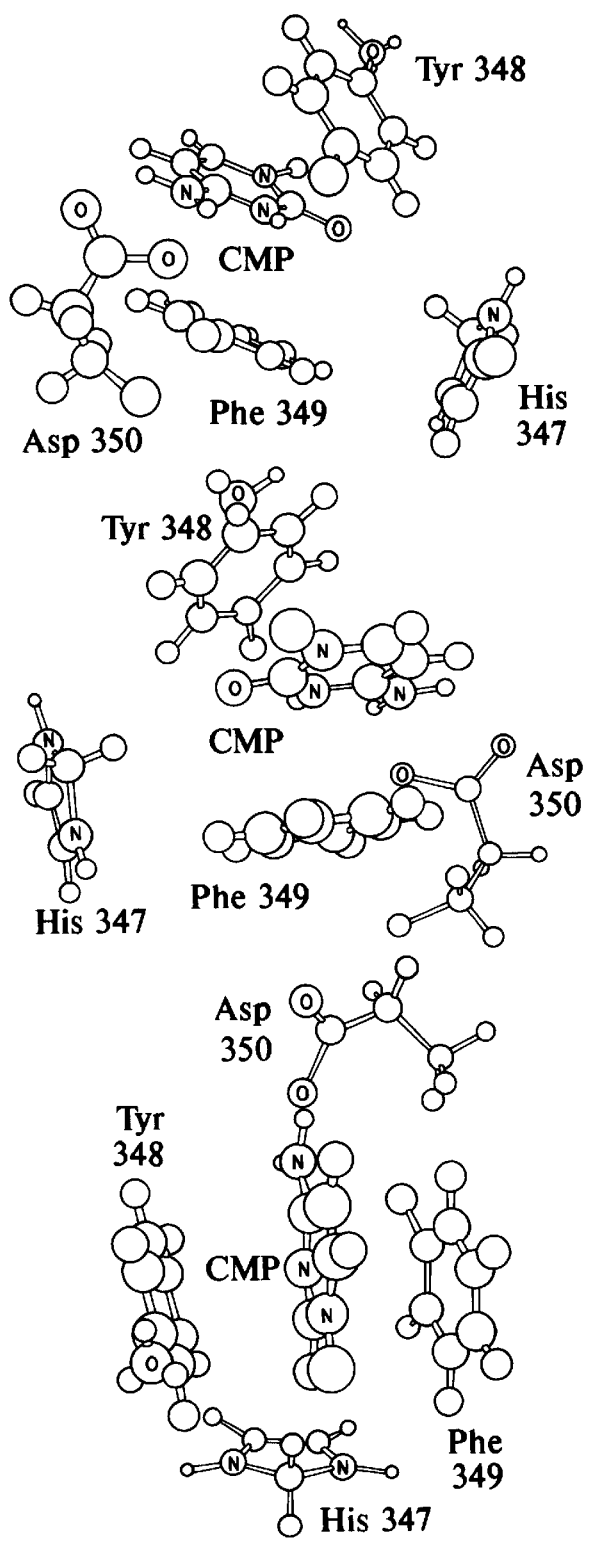
FIG. 8 shows the a three-dimensional (3D) model of nucleotide base recognition by the STP domain. Shown are H-Y-F-D side chains and cytosine. The oxygen and the nitrogen atoms are marked. Several projections are shown.

The human copy of ST3Gal V contained three alternatively spliced forms (ASFs) that could be detected using primers F 619 and R 1253 (Table 1). According to the size of PCR products amplified using these primers, the ASFs were termed ASF 800, with a PCR product of 792 bp (total length, 3494 bp, GenBank # AF119417); ASF 600, with a PCR product of 634 bp (full length, 2288 bp, GenBank # AF119415); and ASF 400, with a PCR product of 454 bp (total length, 2415 bp, GenBank # AF119418). The mouse GM3-synthase was deposited with GenBank accession # AF119416. Two ASFs were found for the human ST3Gal VI (GenBank # AF119391). Mouse ST3Gal VI was deposited in the GenBank with accession number AF119390. To date, no ASFs were found for the mouse counterparts. Human ASFs of ST3Gal V and VI were used to assay for the GM3-synthase and GD1a-synthase activity using LacCer and GM1 as substrates, respectively. Of all three alternatively spliced forms of ST3Gal V and two forms of ST3Gal VI, only ASF 600 of ST3Gal V revealed GM3-synthase activity. The complete nucleotide and the corresponding amino acid sequence of this ASF, together with the sites of alternative splicing, are shown in FIG. 6 (SEQ ID NOS:12 and 13). Among all ASFs of ST3Gal V, ASF 600 had the highest homology with mouse ST3Gal V and with other STs. ASF 600 of ST3Gal V contained three conserved in-frame potential initiation codons. The amino acid sequence that starts from the third initiation codon had the highest homology with other STs and was sufficient for expression of functional activity. Therefore, numbering of amino acid residues along the protein sequence starts with M of the third reading frame. Human GM3-synthase contains 362 amino acid residues and the mouse analogue has 359 amino acid residues. The degree of similarity between the two enzymes is 90.5% and the degree of identity is 86.4% at the amino acid level and 84.7% at the cDNA level in the coding region, starting with ORF 3. This degree of similarity corresponds to the average similarity of 85% expected for identical mouse and human genes. The similarity in the 5' untranslated region drops to 81% and in the 3' untranslated region drops to 54%. The hydrophobicity plot of human and mouse GM3-synthase is shown in FIG. 7. It reveals an N-terminal transmembrane domain common to all mammalian STs and a predicted type II transmembrane topology (37–39). The human 4ST3Gal V has a calculated molecular mass of 41.74 KD and a pI of 8.74 and the mouse enzyme has a calculated molecular mass of 41.24 KD and a pI of 7.50. Human and mouse ST3Gal V have conserved STL, STS, and STP motifs common to other STs, as well as an ST3 motif common to all ST3 STs. In the STP motif, we have assigned the function of the cytosine recognition of the donor CMP-sialic acid molecule through the stacking interaction of the aromatic ring of Y/F/W residues with cytosine, electrostatic interaction between amino acids H or C, and either oxygen from the cytosine or phosphate group, and electrostatic interaction between D/E or Q residue and amino group of the cytosine (FIG. 8). Each ST3Gal V contains three potential N-glycosylation sites that are conserved for the mouse and human enzymes, five conserved potential casein kinase II phosphorylation sites, two conserved potential cAMP/cGMP-dependent protein kinase phosphorylation sites, as well as several non-conserved phosphorylation sites (40–42).

TABLE 1

List of primers.

| Name | Amino acid seq. | Primer | | Degener |
|---|---|---|---|---|
| 1Fa | CRRCVVG | (SEQ ID NO: 35) | TG(C/T)CG(C/G)CG(C/G)TG(T/C)GT(G/C/T)GT(G/C/T)GG (SEQ ID NO:40) | 432 |
| 1Fb | CRRCIIVG | (SEQ ID NO: 36) | TG(C/T)CG(C/G)CG(C/G)TG(T/C)AT(C/T)AT(C/T)GT(G/C/T)GG (SEQ ID NO:41) | 192 |
| 1Fc | CKRCVVG | (SEQ ID NO: 37) | TG(C/T)AA(A/G)CG(C/G)CG(C/G)TG(T/C)GT(G/C/T)GT(G/C/T)GG (SEQ ID NO:42) | 432 |
| 1Fd | CKKCVVG | (SEQ ID NO: 38) | TG(C/T)AA(A/G)AA(A/G)TG(C/T)GT(G/C/T)GT(G/C/T)GG (SEQ ID NO:43) | 432 |
| 1Fe | CRRCAVVG | (SEQ ID NO: 39) | TG(C/T)CG(C/G)CG(C/G)GCNGT(G/C/T)GT(G/C/T)GG (SEQ ID NO:44) | 576 |
| 2Fa | VVVGNGG | (SEQ ID NO: 45) | GT(G/C/T)GT(G/C/T)GT(G/C/T)GGNAA(T/C)GGNGG (SEQ ID NO:49) | 864 |
| 2Fb | VVVGNGH | (SEQ ID NO: 46) | GT(G/C/T)GT(G/C/T)GT(G/C/T)GGNAA(T/C)GGNCA (SEQ ID NO:50) | 864 |
| 2Fc | VVVGNSG | (SEQ ID NO: 47) | GT(G/C/T)GT(G/C/T)GT(G/C/T)GGNAA(T/C)(T/A)(C/G)NGG (SEQ ID NO:51) | 3456 |
| 2Fd | VVVGNSH | (SEQ ID NO: 48) | GT(G/C/T)GT(G/C/T)GT(G/C/T)GGNAA(T/C)(T/A)(C/G)NCA (SEQ ID NO:52) | 3456 |
| 3Fa | RLNSAPV | (SEQ ID NO: 53) | AG(G/A)(T/C)TGAA(T/C)(T/A)(C/G)NGCNCCNGT (SEQ ID NO:55) | 2048 |
| 3Fb | RLNNAPV | (SEQ ID NO: 54) | AG(G/A)(T/C)TGAA(T/C)A(T/C)GCNCCNGT (SEQ ID NO:56) | 256 |
| 4Fa | TYPEGA | (SEQ ID NO: 57) | ACNTA(C/T)CCNGA(G/A)GGNGC (SEQ ID NO:62) | 256 |
| 4Fb | FYPESA | (SEQ ID NO: 58) | TT(T/C)TA(C/T)CCNGA(G/A)(A/T)(G/C)NGC (SEQ ID NO:63) | 512 |
| 4Fc | TYPESA | (SEQ ID NO: 59) | ACNTA(C/T)CCNGA(G/A)(A/T)(G/C)NGC (SEQ ID NO:64) | 1024 |
| 4Fd | FYPEGA | (SEQ ID NO: 60) | TT(T/C)TA(C/T)CCNGA(G/A)GGNGC (SEQ ID NO:65) | 128 |
| 4Fe | RLFYPES | (SEQ ID NO: 61) | (C/A)GNCTNTT(C/T)TA(C/T)CCNGA(G/A)(T/A)C (SEQ ID NO:66) | 2048 |
| 1Ra | rev. AGFGYD | (SEQ ID NO:67) | (A/G)TC(A/G)TANCC(A/G)AANCCNGC (SEQ ID NO:69) | 512 |
| 1Rb | rev. YGFGAD | (SEQ ID NO:68) | (G/A)TCNGCNCC(G/A)AANCC(A/G)TA (SEQ ID NO:70) | 512 |
| 2Ra | rev. RILNP(F/Y) | (SEQ ID NO:71) | (A/G)(A/T)ANGG(A/G)TTNA(A/G)NATNC (SEQ ID NO:73) | 4096 |
| 2Rb | rev IY(H/N)PAF | (SEQ ID NO:72) | (A/G)AANGCNGG(A/G)T(T/G)(A/G)TA(T/G/A)AT (SEQ ID NO:74) | 768 |
| STP-Ra | rev. HYYDx | (SEQ ID NO:75) | NNNNNN(A/G)TC(A/G)TA(A/G)TA(A/G)TG (SEQ ID NO:80) | |
| STP-Rb | rev. HYYEx | (SEQ ID NO:76) | NNNNNN(T/C)TC(A/G)TA(A/G)TA(A/G)TG (SEQ ID NO:81) | |
| STP-Rc | rev. HYWEx | (SEQ ID NO:77) | NNNNNN(T/C)TCCCCA(A/G)TA(A/G)TG (SEQ ID NO:82) | |
| STP-Rd | rev. HYWDx | (SEQ ID NO:78) | NNNNNN(A/G)TCCCCA(A/G)TA(A/G)TG (SEQ ID NO:83) | |

TABLE 1-continued

List of primers.

| Name | Amino acid seq. | Primer | | Degener |
|---|---|---|---|---|
| STP-Re | rev. HYFDx | (SEQ ID NO:79) NNNNNN(A/G)TC(A/G)AA(A/G)TA(A/G)TG | (SEQ ID NO:84) | |
| ST3-III | 4ST3Gal III primers | F: ATCATCGTGGGCAATGGAG | (SEQ ID NO:85) Tm = 58 | |
| Human | | R: CCTGGATGAAATATGGGTTGAG | (SEQ ID NO:86) | |
| ST3-V | 4ST3Gal V primers for ASF | F 619: TATTGGAAGCGGAGGAATACTG | (SEQ ID NO:87) Tm = 58 | |
| ASF | | R 1253: CTTTCACCACTCCCTCTTTTGAC | (SEQ ID NO:88) | |

F – forward, R – reverse, rev. – amino acid sequence was used to design reverse primers, seq. – sequence, Degen. – degree of degeneracy (number of possible combinations). NNNNNN – six random nucleotides were included in the STP primer sequence when it was used in primary PCR reaction, but were omitted when it was used in the cDNA synthesis. Modified stop codon is shown in bold, additional KpnI site is underlined, sequence added to facilitate cloning is shown in small letters. Tm – annealing temperature used in PCR. M – Mouse, H – Human.

REFERENCES

1. Tsuji, S., Datta, A. K., and Paulson, J. C. (1996) Systematic nomenclature for sialyltransferases [letter]. *Glycobiology* 6, v–vii
2. Bremer, E. G., Hakomori, S., Bowen-Pope, D. F., Raines, E., and Ross, R. (1984) Ganglioside-mediated modulation of cell growth, growth factor binding, and receptor phosphorylation. *J Biol Chem* 259, 6818–6825
3. Bremer, E. G., Schlessinger, J., and Hakomori, S. (1986) Ganglioside-mediated modulation of cell growth. Specific effects of GM3 on tyrosine phosphorylation of the epidermal growth factor receptor. *J Biol Chem* 261, 2434–2440
4. Nojiri, H., Takaku, F., Ohta, M., Miura, Y., and Saito, M. (1985) Changes in glycosphingolipid composition during differentiation of human leukemic granulocytes in chronic myelogenous leukemia compared with in vitro granulocytic differentiation of human promyelocytic leukemia cell line HL-60. *Cancer Res* 45, 6100–6106
5. Nojiri, H., Takaku, F., Terui, Y., Miura, Y., and Saito, M. (1986) Ganglioside GM3: an acidic membrane component that increases during macrophage-like cell differentiation can induce monocytic differentiation of human myeloid and monocytoid leukemic cell lines HL-60 and U937. *Proc Natl Acad Sci USA* 83, 782–786
6. Nojiri, H., Kitagawa, S., Nakamura, M., Kirito, K., Enomoto, Y., and Saito, M. (1988) Neolacto-series gangliosides induce granulocytic differentiation of human promyelocytic leukemia cell line HL-60. *J Biol Chem* 263, 7443–7446
7. Yada, Y., Okano, Y., and Nozawa, Y. (1991) Ganglioside GQ1b-induced terminal differentiation in cultured mouse keratinocytes. Phosphoinositide turnover forms the onset signal. *Biochem J* 279, 665–670
8. Rahmann, H., Rosner, H., Kortje, K. H., Beitinger, H., and Seybold, V. (1994) Ca(2+)-ganglioside-interaction in neuronal differentiation and development. *Prog Brain Res* 101, 127–145
9. Ferrari, G., and Greene, L. A. (1998) Promotion of neuronal survival by GM1 ganglioside. Phenomenology and mechanism of action. *Ann N.Y. Acad Sci* 845, 263–273
10. Hakomori, S. (1990) Bifunctional role of glycosphingolipids. Modulators for transmembrane signaling and mediators for cellular interactions. *J Biol Chem* 265, 18713–18716
11. Hakomori, S. (1997) *Sphingolipid-mediated signal transduction*, R.G. Landes Company and Chapman & Hall
12. Hakomori, S., and Igarashi, Y. (1995) Functional role of glycosphingolipids in cell recognition and signaling. *J Biochem* (Tokyo) 118, 1091–1103
13. Hynds, D. L., Burry, R. W., and Yates, A. J. (1997) Gangliosides inhibit growth factor-stimulated neurite outgrowth in SH-SY5Y human neuroblastoma cells. *J Neurosci Res* 47, 617–625
14. Katoh, N. (1995) Inhibition by phospholipids, lysophospholipids and gangliosides of melittin-induced phosphorylation in bovine mammary gland. *Toxicology* 104, 73–81
15. Yates, A. J., and Rampersaud, A. (1998) Sphingolipids as receptor modulators. An overview. *Ann NY Acad Sci* 845, 57–71
16. Suarez Pestana, E., Greiser, U., Sanchez, B., Fernandez, L. E., Lage, A., Perez, R., and Bohmer, F. D. (1997) Growth inhibition of human lung adenocarcinoma cells by antibodies against epidermal growth factor receptor and by ganglioside GM3: involvement of receptor-directed protein tyrosine phosphatase(s). *Br J Cancer* 75, 213–220
17. Goldenring, J. R., Otis, L. C., Yu, R. K., and DeLorenzo, R. J. (1985) Calcium/ganglioside-dependent protein kinase activity in rat brain membrane. *J Neurochem* 44, 1229–1234
18. Kreutter, D., Kim, J. Y., Goldenring, J. R., Rasmussen, H., Ukomadu, C., DeLorenzo, R. J., and Yu, R. K. (1987) Regulation of protein kinase C activity by gangliosides. *J Biol Chem* 262, 1633–1637
19. Kim, J. Y., Goldenring, J. R., DeLorenzo, R. J., and Yu, R. K. (1986) Gangliosides inhibit phospholipid-sensitive Ca2+-dependent kinase phosphorylation of rat myelin basic proteins. *J Neurosci Res* 15, 159–166
20. Matecki, A., Stopa, M., Was, A., and Pawelczyk, T. (1997) Effect of sphingomyelin and its metabolites on the activity of human recombinant PLC delta 1. *Int J Biochem Cell Biol* 29, 815–828
21. Yang, F. Y., Wang, L. H., Yang, X. Y., Tsui, Z. C., and Tu, Y. P. (1997) The role of ganglioside GM3 in the modulation of conformation and activity of sarcoplasmic reticulum Ca(2+)-ATPase. *Biophys Chem* 68, 137–146
22. Misasi, R., Sorice, M., Garofalo, T., Griggi, T., Campana, W., Giammatteo, M., Pavan, A., Hiraiwa, M., Pontieri, M., and O'Brien, J. (1998) Colocalization and Complex Formation Between Prosaposin and Monosialoganglioside GM3 in Neural Cells. *J. Neurochem.* 71, 2313–2321
23. Hakomori, S., Yamamura, S., and Handa, A. K. (1998) Signal transduction through glyco(sphingo)lipids. Introduction and recent studies on glyco(sphingo)lipid-enriched microdomains. *Ann NY Acad Sci* 845, 1–10
24. Kojima, N., and Hakomori, S. (1991) Cell adhesion, spreading, and motility of GM3-expressing cells based on glycolipid-glycolipid interaction. *J Biol Chem* 266, 17552–17558
25. Kojima, N., Shiota, M., Sadahira, Y., Handa, K., and Hakomori, S. (1992) Cell adhesion in a dynamic flow system as compared to static system. Glycosphingolipid-glycosphingolipid interaction in the dynamic system predominates over lectin- or integrin-based mechanisms in adhesion of B16 melanoma cells to non-activated endothelial cells. *J Biol Chem* 267, 17264–17270
26. Hammache, D., Yahi, N., Pieroni, G., Ariasi, F., Tamalet, C., and Fantini, J. (1998) Sequential interaction of CD4 and HIV-1 gp120 with a reconstituted membrane patch of ganglioside GM3: implications for the role of glycolipids as potential HIV-1 fusion cofactors. *Biochem Biophys Res Commun* 246, 117–122
27. Hammache, D., Pieroni, G., Yahi, N., Delezay, O., Koch, N., Lafont, H., Tamalet, C., and Fantini, J. (1998) Specific interaction of HIV-1 and HIV-2 surface envelope glycoproteins with monolayers of galactosylceramide and ganglioside GM3. *J Biol Chem* 273, 7967–7971
28. Paulson, J. C., Beranek, W. E., and Hill, R. L. (1977) Purification of a sialyltransferase from bovine colostrum by affinity chromatography on CDP-agarose. *J Biol Chem* 252, 2356–2362
29. Gillespie, W., Kelm, S., and Paulson, J. C. (1992) Cloning and expression of the Gal beta 1, 3GalNAc alpha 2,3-sialyltransferase. *J Biol Chem* 267, 21004–21010
30. Haraguchi, M., Yamashiro, S., Yamamoto, A., Furukawa, K., Takamiya, K., Lloyd, K. O., and Shiku, H. (1994) Isolation of GD3 synthase gene by expression cloning of GM3 alpha-2,8-sialyltransferase cDNA using anti-GD2 monoclonal antibody. *Proc Natl Acad Sci USA* 91, 10455–10459

31. Sasaki, K., Watanabe, E., Kawashima, K., Sekine, S., Dohi, T., Oshima, M., Hanai, N., Nishi, T., and Hasegawa, M. (1993) Expression cloning of a novel Gal beta (1-3/1-4) GlcNAc alpha 2,3-sialyltransferase using lectin resistance selection. *J Biol Chem* 268, 22782–22787

32. Kim, Y. J., Kim, K. S., Do, S., Kim, C. H., Kim, S. K., and Lee, Y. C. (1997) Molecular cloning and expression of human alpha2,8-sialyltransferase (hST8Sia V). *Biochem Biophys Res Commun* 235, 327–330

33. Nakayama, J., Fukuda, M. N., Hirabayashi, Y., Kanamori, A., Sasaki, K., Nishi, T., and Fukuda, M. (1996) Expression cloning of a human GT3 synthase. GD3 AND GT3 are synthesized by a single enzyme. *J Biol Chem* 271, 3684–3691

34. Lee, Y. C., Kurosawa, N., Hamamoto, T., Nakaoka, T., and Tsuji, S. (1993) Molecular cloning and expression of Gal beta 1,3GalNAc alpha 2,3-sialyltransferase from mouse brain. *Eur J Biochem* 216, 377–385

35. Kapitonov, D., and Yu, R. K. (1997) Molecular cloning and expression of ceramide galactosyltransferases. Comparison with other glycosyltransferases. Dissertation. Medical College of Virginia of Virginia Commonwealth University, Richmond 36. Gu, X., Preuss, U., Gu, T., and Yu, R. K. (1995) Regulation of sialyltransferase activities by phosphorylation and dephosphorylation. *J Neurochem* 64, 2295–2302

37. Sipos, L., and von Heijne, G. (1993) Predicting the topology of eukaryotic membrane proteins. *Eur J Biochem* 213, 1333–1340

38. Nakashiima, H., and Nishikawa, K. (1992) The amino acid composition is different between the cytoplasmic and extracellular sides in membrane proteins. *FEBS Lett* 303, 141–146

39. Hartmann, E, Rapoport, T. A., and Lodish, H. F. (1989) Predicting the orientation of eukaryotic membrane-spanning proteins. *Proc Natl Acad Sci USA* 86, 5786–5790

40. Nigam, S. K., and Blobel, G. (1989) Cyclic AMP-dependent protein kinase in canine pancreatic rough endoplasmic reticulum. *J Biol Chem* 264, 16927–16932

41. Ou, W. J., Thomas, D. Y., Bell, A. W., and Bergeron, J. J. (1992) Casein kinase II phosphorylation of signal sequence receptor alpha and the associated membrane chaperone calnexin. *J Biol Chem* 267, 23789–23796

42. Sfeir, C., and Veis, A. (1995) Casein kinase localization in the endoplasmic reticulum of the ROS 17/2.8 cell line. *J Bone Miner Res* 10, 607–615

Without further elaboration, it is believed that one skilled in the art can, using the preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

---

SEQUENCE LISTING

<160> NUMBER OF SEQ ID NOS: 94

<210> SEQ ID NO 1
<211> LENGTH: 2288
<212> TYPE: DNA
<213> ORGANISM: Homo sapiens
<220> FEATURE:
<221> NAME/KEY: CDS
<222> LOCATION: (29)..(1282)

<400> SEQUENCE: 1

```
ggcggccggc cggcgccccc tcattagt atg cgg acg aag gcg gcg ggc tgc          52
                                Met Arg Thr Lys Ala Ala Gly Cys
                                  1               5 gcg gag cgg cgt ccc ctg cag ccg cgg acc gag gca gcg gcg gca cct         100
Ala Glu Arg Arg Pro Leu Gln Pro Arg Thr Glu Ala Ala Ala Ala Pro
         10                  15                  20 gcc ggc cga gca atg cca agt gag tac acc tat gtg aaa ctg aga agt         148
Ala Gly Arg Ala Met Pro Ser Glu Tyr Thr Tyr Val Lys Leu Arg Ser
 25                  30                  35                  40 gat tgc tcg agg cct tcc ctg caa tgg tac acc cga gct caa agc aag         196
Asp Cys Ser Arg Pro Ser Leu Gln Trp Tyr Thr Arg Ala Gln Ser Lys
                 45                  50                  55 atg aga agg ccc agc ttg tta tta aaa gac atc ctc aaa tgt aca ttg         244
Met Arg Arg Pro Ser Leu Leu Leu Lys Asp Ile Leu Lys Cys Thr Leu
             60                  65                  70 ctt gtg ttt gga gtg tgg atc ctt tat atc ctc aag tta aat tat act         292
Leu Val Phe Gly Val Trp Ile Leu Tyr Ile Leu Lys Leu Asn Tyr Thr
         75                  80                  85 act gaa gaa tgt gac atg aaa aaa atg cat tat gtg gac cct gac cgt         340
Thr Glu Glu Cys Asp Met Lys Lys Met His Tyr Val Asp Pro Asp Arg
     90                  95                 100
```

```
gta aag aga gct cag aaa tat gct cag caa gtc ttg cag aag gaa tgt        388
Val Lys Arg Ala Gln Lys Tyr Ala Gln Gln Val Leu Gln Lys Glu Cys
105                 110                 115                 120 cgt ccc aag ttt gcc aag aca tca atg gcg ctg tta ttt gag cac agg        436
Arg Pro Lys Phe Ala Lys Thr Ser Met Ala Leu Leu Phe Glu His Arg
            125                 130                 135 tat agc gtg gac tta ctc cct ttt gtg cag aag gcc ccc aaa gac agt        484
Tyr Ser Val Asp Leu Leu Pro Phe Val Gln Lys Ala Pro Lys Asp Ser
        140                 145                 150 gaa gct gag tcc aag tac gat cct cct ttt ggg ttc cgg aag ttc tcc        532
Glu Ala Glu Ser Lys Tyr Asp Pro Pro Phe Gly Phe Arg Lys Phe Ser
    155                 160                 165 agt aaa gtc cag acc ctc ttg gaa ctc ttg cca gag cac gac ctc cct        580
Ser Lys Val Gln Thr Leu Leu Glu Leu Leu Pro Glu His Asp Leu Pro
170                 175                 180 gaa cac ttg aaa gcc aag acc tgt cgg cgc tgt gtg gtt att gga agc        628
Glu His Leu Lys Ala Lys Thr Cys Arg Arg Cys Val Val Ile Gly Ser
185                 190                 195                 200 gga gga ata ctg cac gga tta gaa ctg ggc cac acc ctg aac cag ttc        676
Gly Gly Ile Leu His Gly Leu Glu Leu Gly His Thr Leu Asn Gln Phe
            205                 210                 215 gat gtt gtg ata agg tta aac agt gca cca gtt gag gga tat tca gaa        724
Asp Val Val Ile Arg Leu Asn Ser Ala Pro Val Glu Gly Tyr Ser Glu
        220                 225                 230 cat gtt gga aat aaa act act ata agg atg act tat cca gag ggc gca        772
His Val Gly Asn Lys Thr Thr Ile Arg Met Thr Tyr Pro Glu Gly Ala
    235                 240                 245 cca ctg tct gac ctt gaa tat tat tcc aat gac tta ttt gtt gct gtt        820
Pro Leu Ser Asp Leu Glu Tyr Tyr Ser Asn Asp Leu Phe Val Ala Val
250                 255                 260 tta ttt aag agt gtt gat ttc aac tgg ctt caa gca atg gta aaa aag        868
Leu Phe Lys Ser Val Asp Phe Asn Trp Leu Gln Ala Met Val Lys Lys
265                 270                 275                 280 gaa acc ctg cca ttc tgg gta cga ctc ttc ttt tgg aag cag gtg gca        916
Glu Thr Leu Pro Phe Trp Val Arg Leu Phe Phe Trp Lys Gln Val Ala
            285                 290                 295 gaa aaa atc cca ctg cag cca aaa cat ttc agg att ttg aat cca gtt        964
Glu Lys Ile Pro Leu Gln Pro Lys His Phe Arg Ile Leu Asn Pro Val
        300                 305                 310 atc atc aaa gag act gcc ttt gac atc ctt cag tac tca gag cct cag       1012
Ile Ile Lys Glu Thr Ala Phe Asp Ile Leu Gln Tyr Ser Glu Pro Gln
    315                 320                 325 tca agg ttc tgg ggc cga gat aag aac gtc ccc aca atc ggt gtc att       1060
Ser Arg Phe Trp Gly Arg Asp Lys Asn Val Pro Thr Ile Gly Val Ile
330                 335                 340 gcc gtt gtc tta gcc aca cat ctg tgc gat gaa gtc agt ttg gcg ggt       1108
Ala Val Val Leu Ala Thr His Leu Cys Asp Glu Val Ser Leu Ala Gly
345                 350                 355                 360 ttt gga tat gac ctc aat caa ccc aga aca cct ttg cac tac ttc gac       1156
Phe Gly Tyr Asp Leu Asn Gln Pro Arg Thr Pro Leu His Tyr Phe Asp
            365                 370                 375 agt caa tgc atg gct gct atg aac ttt cag acc atg cat aat gtg aca       1204
Ser Gln Cys Met Ala Ala Met Asn Phe Gln Thr Met His Asn Val Thr
        380                 385                 390 acg gaa acc aag ttc ctc tta aag ctg gtc aaa gag gga gtg gtg aaa       1252
Thr Glu Thr Lys Phe Leu Leu Lys Leu Val Lys Glu Gly Val Val Lys
    395                 400                 405 gat ctc agt gga ggc att gat cgt gaa ttt tgaacacaga aaacctcagt         1302
Asp Leu Ser Gly Gly Ile Asp Arg Glu Phe
```

-continued

```
tgaaaatgca actctaactc tgagagctgt ttttgacagc cttcttgatt tatttctcca    1362
tcctgcagat actttgaagt gcagctcatg tttttaactt ttaatttaaa aacacaaaaa    1422 aaatttagc tcttcccact ttttttttcc tatttatttg aggtcagtgt ttgttttttgc    1482 acaccatttt gtaaatgaaa cttaagaatt gaattggaaa gacttctcaa agagaattgt    1542
atgtaacgat gttgtattga tttttaagaa agtaatttaa tttgtaaaac ttctgctcgt    1602
ttacactgca cattgaatac aggtaactaa ttggaaggag aggggaggtc actcttttga    1662
tggtggccct gaacctcatt ctggttccct gctgcgctgc ttggtgtgac ccacggagga    1722
tccactccca ggatgacgtg ctccgtagct ctgctgctga tactgggtct gcgatgcagc    1782
ggcgtaggct ggctggttga aaggtcaca accttctct gttggtctgc cttctgctga    1842
aagactcgag aaccaaccag ggaagctgtc ctgaaggtcc ctggtcggag agggacatag    1902
aatctgtgac ctctgacaac tgtgaagcca ccctgggcta cagaaaccac agtcttccca    1962
gcaattatta caattcttga attccttggg gattttttac tgcccttca aagcacttaa    2022 gtgttagatc taacgtgttc cagtgtctgt ctgaggtgac ttaaaaaatc agaacaaaac    2082
ttctattatc cagagtcatg ggagagtaca ccctttccag gaataatgtt ttgggaaaca    2142
ctgaaatgaa atcttcccag tattataaat tgtgtattta aaaaaaagaa acttttctga    2202
atgcctacct ggcggtgtat accaggcagt gtcccagttt aaaaagatga aaagaataa    2262 aaactttga ggaaaaaaaa aaaaaa    2288
```

<210> SEQ ID NO 2
<211> LENGTH: 418
<212> TYPE: PRT
<213> ORGANISM: Homo sapiens

<400> SEQUENCE: 2

```
Met Arg Thr Lys Ala Ala Gly Cys Ala Glu Arg Arg Pro Leu Gln Pro
  1               5                  10                  15

Arg Thr Glu Ala Ala Ala Pro Ala Gly Arg Ala Met Pro Ser Glu
             20                  25                  30

Tyr Thr Tyr Val Lys Leu Arg Ser Asp Cys Ser Arg Pro Ser Leu Gln
         35                  40                  45

Trp Tyr Thr Arg Ala Gln Ser Lys Met Arg Arg Pro Ser Leu Leu Leu
     50                  55                  60

Lys Asp Ile Leu Lys Cys Thr Leu Leu Val Phe Gly Val Trp Ile Leu
 65                  70                  75                  80

Tyr Ile Leu Lys Leu Asn Tyr Thr Thr Glu Glu Cys Asp Met Lys Lys
                 85                  90                  95

Met His Tyr Val Asp Pro Asp Arg Val Lys Arg Ala Gln Lys Tyr Ala
            100                 105                 110

Gln Gln Val Leu Gln Lys Glu Cys Arg Pro Lys Phe Ala Lys Thr Ser
        115                 120                 125

Met Ala Leu Leu Phe Glu His Arg Tyr Ser Val Asp Leu Leu Pro Phe
    130                 135                 140

Val Gln Lys Ala Pro Lys Asp Ser Glu Ala Glu Ser Lys Tyr Asp Pro
145                 150                 155                 160

Pro Phe Gly Phe Arg Lys Phe Ser Ser Lys Val Gln Thr Leu Leu Glu
                165                 170                 175

Leu Leu Pro Glu His Asp Leu Pro Glu His Leu Lys Ala Lys Thr Cys
            180                 185                 190
```

-continued

```
Arg Arg Cys Val Val Ile Gly Ser Gly Gly Ile Leu His Gly Leu Glu
            195                 200                 205
Leu Gly His Thr Leu Asn Gln Phe Asp Val Val Ile Arg Leu Asn Ser
        210                 215                 220
Ala Pro Val Glu Gly Tyr Ser Glu His Val Gly Asn Lys Thr Thr Ile
225                 230                 235                 240
Arg Met Thr Tyr Pro Glu Gly Ala Pro Leu Ser Asp Leu Glu Tyr Tyr
                245                 250                 255
Ser Asn Asp Leu Phe Val Ala Val Leu Phe Lys Ser Val Asp Phe Asn
            260                 265                 270
Trp Leu Gln Ala Met Val Lys Lys Glu Thr Leu Pro Phe Trp Val Arg
        275                 280                 285
Leu Phe Phe Trp Lys Gln Val Ala Glu Lys Ile Pro Leu Gln Pro Lys
    290                 295                 300
His Phe Arg Ile Leu Asn Pro Val Ile Ile Lys Glu Thr Ala Phe Asp
305                 310                 315                 320
Ile Leu Gln Tyr Ser Glu Pro Gln Ser Arg Phe Trp Gly Arg Asp Lys
                325                 330                 335
Asn Val Pro Thr Ile Gly Val Ile Ala Val Val Leu Ala Thr His Leu
            340                 345                 350
Cys Asp Glu Val Ser Leu Ala Gly Phe Gly Tyr Asp Leu Asn Gln Pro
        355                 360                 365
Arg Thr Pro Leu His Tyr Phe Asp Ser Gln Cys Met Ala Ala Met Asn
    370                 375                 380
Phe Gln Thr Met His Asn Val Thr Thr Glu Thr Lys Phe Leu Leu Lys
385                 390                 395                 400
Leu Val Lys Glu Gly Val Val Lys Asp Leu Ser Gly Gly Ile Asp Arg
                405                 410                 415
Glu Phe

<210> SEQ ID NO 3
<211> LENGTH: 2235
<212> TYPE: DNA
<213> ORGANISM: Murinae gen. sp.
<220> FEATURE:
<221> NAME/KEY: CDS
<222> LOCATION: (87)..(1328)

<400> SEQUENCE: 3
gggctgaatt ggcgcgagcg cggcgccggg ggctggctgg ggcgcggggc cccgggctgg      60
cggcttgcca gcgctccctc cctagc atg cac aca gag gcg gtg ggc ggc gcg     113
                             Met His Thr Glu Ala Val Gly Gly Ala
                               1               5 gcg cgg agg ccc cag aag ctg cga agc caa gca gcg gca cct gcc tgc     161
Ala Arg Arg Pro Gln Lys Leu Arg Ser Gln Ala Ala Ala Pro Ala Cys
 10                  15                  20                  25 cga gca atg cca agt gag ttc acc tct gca aag ctg aga agt gat tgc     209
Arg Ala Met Pro Ser Glu Phe Thr Ser Ala Lys Leu Arg Ser Asp Cys
                 30                  35                  40 tca agg acc tcc ctg caa tgg tac acc cga acc cag cac aag atg aga     257
Ser Arg Thr Ser Leu Gln Trp Tyr Thr Arg Thr Gln His Lys Met Arg
             45                  50                  55 aga ccc agc ttg tta ata aaa gac atc tgc aag tgc acg ttg gtt gca     305
Arg Pro Ser Leu Leu Ile Lys Asp Ile Cys Lys Cys Thr Leu Val Ala
         60                  65                  70 ttt gga gtc tgg ctc ctg tac atc ctc att ttg aat tac acc gct gaa     353
```

```
                  Phe Gly Val Trp Leu Leu Tyr Ile Leu Ile Leu Asn Tyr Thr Ala Glu
                       75                  80                  85 gaa tgt gac atg aaa aga atg cac tat gtg gac cct gac cgg ata aag       401
Glu Cys Asp Met Lys Arg Met His Tyr Val Asp Pro Asp Arg Ile Lys
 90                  95                 100                 105 aga gct cag agc tat gct cag gaa gtc ttg cag aag gaa tgt cgg ccc       449
Arg Ala Gln Ser Tyr Ala Gln Glu Val Leu Gln Lys Glu Cys Arg Pro
                110                 115                 120 agg tac gcg aag acg gct atg gct ctg tta ttt gag gac agg tac agc       497
Arg Tyr Ala Lys Thr Ala Met Ala Leu Leu Phe Glu Asp Arg Tyr Ser
            125                 130                 135 atc aac ttg gag cct ttt gtg cag aag gtc ccc acg gcc agt gaa gct       545
Ile Asn Leu Glu Pro Phe Val Gln Lys Val Pro Thr Ala Ser Glu Ala
        140                 145                 150 gag ctc aag tat gac ccg cct ttt gga ttc cgg aag ttc tcc agt aaa       593
Glu Leu Lys Tyr Asp Pro Pro Phe Gly Phe Arg Lys Phe Ser Ser Lys
    155                 160                 165 gtc cag agc ctc ttg gat atg ctg ccc gaa cat gac ttt cct gaa cac       641
Val Gln Ser Leu Leu Asp Met Leu Pro Glu His Asp Phe Pro Glu His
170                 175                 180                 185 ttg aga gcc aag gcc tgc aag cgc tgt gtg gtt gtt ggg aac ggg ggc       689
Leu Arg Ala Lys Ala Cys Lys Arg Cys Val Val Val Gly Asn Gly Gly
                190                 195                 200 atc ctg cac gga cta gag ctg ggt cac gcc ctc aac cag ttc gat gtg       737
Ile Leu His Gly Leu Glu Leu Gly His Ala Leu Asn Gln Phe Asp Val
            205                 210                 215 gta ata agg ttg aac agt gcg cca gtt gag ggt tac tct gaa cac gtt       785
Val Ile Arg Leu Asn Ser Ala Pro Val Glu Gly Tyr Ser Glu His Val
        220                 225                 230 ggg aat aaa act act ata agg atg act tac cca gag ggt gcg cca ctg       833
Gly Asn Lys Thr Thr Ile Arg Met Thr Tyr Pro Glu Gly Ala Pro Leu
    235                 240                 245 tcg gac gtt gaa tac tac gcc aat gat ttg ttc gtt act gtt tta ttt       881
Ser Asp Val Glu Tyr Tyr Ala Asn Asp Leu Phe Val Thr Val Leu Phe
250                 255                 260                 265 aag agt gtt gat ttc aag tgg ctt caa gca atg gta aaa aat gaa agc       929
Lys Ser Val Asp Phe Lys Trp Leu Gln Ala Met Val Lys Asn Glu Ser
                270                 275                 280 ctg ccc ttt tgg gtt cgc ctc ttc ttt tgg aag caa gtg gca gaa aaa       977
Leu Pro Phe Trp Val Arg Leu Phe Phe Trp Lys Gln Val Ala Glu Lys
            285                 290                 295 gtc cca ctc cag cca aag cac ttc agg att ttg aac cca gtt atc atc     1025
Val Pro Leu Gln Pro Lys His Phe Arg Ile Leu Asn Pro Val Ile Ile
        300                 305                 310 aaa gaa act gcc ttc gac atc ctt cag tac tca gag cct cag tca aga     1073
Lys Glu Thr Ala Phe Asp Ile Leu Gln Tyr Ser Glu Pro Gln Ser Arg
    315                 320                 325 ttc tgg ggc cat gat aag aac atc ccc acg atc ggc gtc att gcc gtt     1121
Phe Trp Gly His Asp Lys Asn Ile Pro Thr Ile Gly Val Ile Ala Val
330                 335                 340                 345 gtc ttg gct aca cat ctg tgt gat gaa gtc agc ctg gca ggc ttt ggc     1169
Val Leu Ala Thr His Leu Cys Asp Glu Val Ser Leu Ala Gly Phe Gly
                350                 355                 360 tac gac ctc agt caa ccc agg acc cct ctg cac tac ttt gac agt cag     1217
Tyr Asp Leu Ser Gln Pro Arg Thr Pro Leu His Tyr Phe Asp Ser Gln
            365                 370                 375 tgc atg ggc gcc atg cac tgg cag gtc atg cac aat gtg acc aca gag     1265
Cys Met Gly Ala Met His Trp Gln Val Met His Asn Val Thr Thr Glu
        380                 385                 390
```

```
acc aag ttc ctc ctg aag ctc ctc aag gag ggc gtg gtg gag gac ctc      1313
Thr Lys Phe Leu Leu Lys Leu Leu Lys Glu Gly Val Val Glu Asp Leu
    395                 400                 405 agc ggc ggc atc cac tgagaactcg aacacggca aacctcaccc agcaccgcag        1368
Ser Gly Gly Ile His
410 ctgagagcgt ggtgagcagc ctccacaggg acttcaccct gcagctgctt cgatgtgcag     1428 ctagtgtttt caaactccac attttttta aaaaggaaa agaaagaaca acagcaacaa      1488 caaaagctct gctctgtgca cctcttcgtc ctatttattt gaagtcagtg ttggattttg     1548 cacagttttg taagttaatc ttaagaatgg gattggaagg acttttcaaa gagaattgta    1608 tagtttattg ttttaagga agtaatttaa tttgcagaaa ctgtacacac gtactctgct     1668 caggtgttga gtggaggaga gggcttctgg ccctggatga tggctgtgat gcccgatact    1728 ggggtctgct gctctgtttg gtagaactga tggcagagaa acttcctgcc tccaggataa    1788 agggcttact catcacctct ggcagctgct agacaagttc ataacccctt tctgctagtc    1848 catctgccag ctggctcgca ggactcaggc agggcagctg tcccggaggc tgctggttgg    1908 tgagccactg tcagctgagc gccgtgatgt tgccccaggg tggaagaagc cacacttcct    1968 acactgtcag ggcactttta aacttctgga ggggtgtgtg tgtgtgtgtg tgtgtgtgtg    2028 tgtgtgtgtg tgtgtgtgtg tgtgtgttca ttctgcccct tccaaatcat ctaagtgtta    2088 tttaaggcac tctgctgttt gtatgagatg gttcatagaa attatgacaa agcctttgtt    2148 atccaggcca tgggaaaagg aaaaagaaaa gaaagaaaga aagaataaa agcttttgag    2208 gagcccctgt taaaaaaaaa aaaaaaa                                        2235
```

<210> SEQ ID NO 4
<211> LENGTH: 414
<212> TYPE: PRT
<213> ORGANISM: Murinae gen. sp.

<400> SEQUENCE: 4

```
Met His Thr Glu Ala Val Gly Gly Ala Ala Arg Arg Pro Gln Lys Leu
  1               5                  10                  15

Arg Ser Gln Ala Ala Ala Pro Ala Cys Arg Ala Met Pro Ser Glu Phe
             20                  25                  30

Thr Ser Ala Lys Leu Arg Ser Asp Cys Ser Arg Thr Ser Leu Gln Trp
         35                  40                  45

Tyr Thr Arg Thr Gln His Lys Met Arg Arg Pro Ser Leu Leu Ile Lys
     50                  55                  60

Asp Ile Cys Lys Cys Thr Leu Val Ala Phe Gly Val Trp Leu Leu Tyr
 65                  70                  75                  80

Ile Leu Ile Leu Asn Tyr Thr Ala Glu Glu Cys Asp Met Lys Arg Met
                 85                  90                  95

His Tyr Val Asp Pro Asp Arg Ile Lys Arg Ala Gln Ser Tyr Ala Gln
            100                 105                 110

Glu Val Leu Gln Lys Glu Cys Arg Pro Arg Tyr Ala Lys Thr Ala Met
        115                 120                 125

Ala Leu Leu Phe Glu Asp Arg Tyr Ser Ile Asn Leu Glu Pro Phe Val
    130                 135                 140

Gln Lys Val Pro Thr Ala Ser Glu Ala Glu Leu Lys Tyr Asp Pro Pro
145                 150                 155                 160

Phe Gly Phe Arg Lys Phe Ser Ser Lys Val Gln Ser Leu Leu Asp Met
                165                 170                 175
```

```
Leu Pro Glu His Asp Phe Pro Glu His Leu Arg Ala Lys Ala Cys Lys
            180                 185                 190

Arg Cys Val Val Gly Asn Gly Ile Leu His Gly Leu Glu Leu
        195                 200                 205

Gly His Ala Leu Asn Gln Phe Asp Val Val Ile Arg Leu Asn Ser Ala
        210                 215                 220

Pro Val Glu Gly Tyr Ser Glu His Val Gly Asn Lys Thr Thr Ile Arg
225                 230                 235                 240

Met Thr Tyr Pro Glu Gly Ala Pro Leu Ser Asp Val Glu Tyr Tyr Ala
                245                 250                 255

Asn Asp Leu Phe Val Thr Val Leu Phe Lys Ser Val Asp Phe Lys Trp
            260                 265                 270

Leu Gln Ala Met Val Lys Asn Glu Ser Leu Pro Phe Trp Val Arg Leu
        275                 280                 285

Phe Phe Trp Lys Gln Val Ala Glu Lys Val Pro Leu Gln Pro Lys His
    290                 295                 300

Phe Arg Ile Leu Asn Pro Val Ile Ile Lys Glu Thr Ala Phe Asp Ile
305                 310                 315                 320

Leu Gln Tyr Ser Glu Pro Gln Ser Arg Phe Trp Gly His Asp Lys Asn
                325                 330                 335

Ile Pro Thr Ile Gly Val Ile Ala Val Val Leu Ala Thr His Leu Cys
            340                 345                 350

Asp Glu Val Ser Leu Ala Gly Phe Gly Tyr Asp Leu Ser Gln Pro Arg
        355                 360                 365

Thr Pro Leu His Tyr Phe Asp Ser Gln Cys Met Gly Ala Met His Trp
    370                 375                 380

Gln Val Met His Asn Val Thr Thr Glu Thr Lys Phe Leu Leu Lys Leu
385                 390                 395                 400

Leu Lys Glu Gly Val Val Glu Asp Leu Ser Gly Gly Ile His
                405                 410

<210> SEQ ID NO 5
<211> LENGTH: 3494
<212> TYPE: DNA
<213> ORGANISM: Homo sapiens

<400> SEQUENCE: 5
gtggcacgat ctcggctcac tgcaagctct gcctcccggg ttcacaccat tctcctgcct      60
cagcctcccg agtagctggg actacaggtg cccaccacca cgtgcccggc taattttgt     120 attttagta gagacgagtt tcaccgtatt agccaggatg gtcatgtttt gttcttgtt     180 tttgttttag agacagggtc tccctctgtc acccaggctg gagtgcagtg gcacaatcac     240
agctcactac agtgtcaacc ttccaggttg aggatcactc gatactcatg cctcagcctc     300
ccatgtagct ggggccacag ggcacacca ccactcctga cccattttt aaaaaatttt      360 ttgtataggt ggggtctcac catgttgccc aggctagcct ccaactcctg ggctcaagca     420
accctctcac cttggcctct caaagtgctg agattatagg tgtgacccgc catgcccgcc     480
tttcctctga gttttgttgc attcacgcag ctcctggctg aggcaaaaca ttaaaatgca     540
tatggaaatg caggctggga aaatgctttg aaaccaatgc aatttctgtg ttaaggggac     600
attccctgat tctttcaggt aatttgcatt ctagactgtg acattctgta tctcaactga     660
taaataagcc tgtttgtcat cctgctagat gagaacctga tatatgaaac cttttttta     720 atcgtggtta aaaaaaacat aaaatttacc atcataatta tttttaaatg taccatttgg     780
```

-continued

```
cagcattaag tatatttaaa ctcttgtgaa acaaatttct agaatgtttt catcttgcaa      840
aaccgaaacg ctgtacctat aaacaactc cccttttctc cctctcttca accctggtaa       900
ccatgttttt atgaatttga ctactttaga tacctcatat aagtcaggtc atacagtatt      960
tgtctctttg tgactggctt cacttagcat aatgtcctca aagtttaact atgttgtagc     1020
atgtatcaga attttatgaa acatgaagtc ttagacaccc cgaagtacat tttcacccca     1080
aatgtatttg aacagtgtta ggctgggggt gggaggcggg agtccttctt gctttgcctg     1140
tgcaatgaaa tgaatacct gctgtgttta tctccttgtc atgtgattct cccaggttgt      1200
ttcttcaagt ttctgagcca aacttaactc taaaaagcaa atattctgtg ttaaaagaca     1260
gtaatcaaca cgggagctac atcagacatc ataggacaaa ttgtcatcta aagagtata     1320 ttttaatgc aggagagttt ttaaaaccca gattggtgtg atttcattcc agagagctca      1380
gaaatatgct cagcaagtct tgcagaagga atgtcgtccc aagtttgcca agacatcaat     1440
ggcgctgtta tttgagcaca ggtatagcgt ggacttactc ccttttgtgc agaaggcccc     1500
caaagacagt gaagctgagt ccaagtacga tcctccttt gggttccgga agttctccag      1560
taaagtccgg accctcttgg aactcttgcc agagcacgac ctccctgaac acttgaaagc     1620
caagacctgt cggcgctgtg tggttattgg aagcggagga atactgcacg gattagaact     1680
gggccacacc ctgaaccagt tcgatgttgt gataagaact cagtgcactg ctcttggtca     1740
gtgtggctcc aggaacagtg agggacacag gaagctcttc acagtccctg cccacaaggg    1800
acttaacgtt tgagaagttg aaacaaaaac acaaatggt tggatgctcc aaactgtcat      1860
actgacccta agttggagga gcatgctgct ggctacagtt aaacagtgca ccagttgagg     1920
gatattcaga acatgttgga aataaaacta ctataaggat gacttatcca gagggcgcac     1980
cactgtctga ccttgaatat tattccaatg acttatttgt tgctgttta tttaagagtg      2040 ttgatttcaa ctggcttcaa gcaatggtaa aaaaggaaac cctgccattc tgggtacgac     2100
tcttcttttg gaagcaggtg gcagaaaaaa tcccactgca gccaaaacat ttcaggattt     2160
tgaatccagt tatcatcaaa gagactgcct ttgacatcct tcagtactca gagcctcagt     2220
caaggttctg gggccgagat aagaacgtcc ccacaatcgg tgtcattgcc gttgtcttag     2280
ccacacatct gtgcgatgaa gtcagttttgg cgggttttgg atatgacctc aatcaaccca    2340 gaacacctt gcactacttc gacagtcaat gcatggctgc tatgaacttt cagaccatgc      2400
ataatgtgac aacggaaacc aagttcctct taaagctggt caaagaggga gtggtgaaag     2460
atctcagtgg aggcattgat cgtgaatttt gaacacagaa aacctcagtt gaaaatgcaa     2520
ctctaactct gagagctgtt tttgacagcc ttccttgattt atttctccat cctgcagata    2580 cttttgaagtg cagctcatgt ttttaacttt taatttaaaa acacaaaaaa aatttagct    2640 cttcccactt ttttttttcct atttatttga ggtcagtgtt tgttttttgca caccattttg   2700 taaatgaaac ttaagaattg aattggaaag acttctcaaa gagaattgta tgtaacgatg    2760
ttgtattgat ttttaagaaa gtaatttaat ttgtaaaact tctgctcgtt tacactgcac    2820
attgaataca ggtaactaat tggaaggaga ggggaggtca ctcttttgat ggtggccctg    2880
aacctcattc tggttccctg ctgcgctgct tggtgtgacc cacggaggat ccactcccag    2940
gatgacgtgc tccgtagctc tgctgctgat actgggtctg cgatgcagcg gcgtaggctg    3000
gctggttgag aaggtcacaa cccttctctg ttggtctgcc ttctgctgaa agactcgaga    3060
accaaccagg gaagctgtcc tgaaggtccc tggtcggaga gggacataga atctgtgacc    3120
tctgacaact gtgaagccac cctgggctac agaaaccaca gtcttcccag caattattac    3180
```

| | |
|---|---|
| aattcttgaa ttccttgggg atttttttact gcccttttcaa agcacttaag tgttagatct | 3240 |
| aacgtgttcc agtgtctgtc tgaggtgact taaaaaatca gaacaaaact tctattatcc | 3300 |
| agagtcatgg gagagtacac cctttccagg aataatgttt tgggaaacac tgaaatgaaa | 3360 |
| tcttcccagt attataaatt gtgtatttaa aaaaaagaaa cttttctgaa tgcctacctg | 3420 |
| gcggtgtata ccaggcagtg tcccagttta aaagatgaa aagaataaa aacttttgag | 3480 |
| gaaaaaaaaa aaaa | 3494 |

<210> SEQ ID NO 6
<211> LENGTH: 2178
<212> TYPE: DNA
<213> ORGANISM: Homo sapiens

<400> SEQUENCE: 6

| | |
|---|---|
| gaagaatgtg acatgaaaaa aatgcattat gtggaccctg accatgtaaa gacctacacc | 60 |
| gtgcctttaa aggaagcagg gccctccctg ctgaagcatt cgatatctta gagctcctga | 120 |
| aggtgcggca ctcgccttga ggcactttct tctgagctgt gagctatggg caagcagtgg | 180 |
| acaatgatgt ctggttgtgc accattgaag caagaacaga aaccatccca gagtggagga | 240 |
| catggcccat gtggtcctct ctgttaaacg agttgaaaca aaagaggaca aggaattgct | 300 |
| gtggctttag acgttgccag gacatgtaga aactcactca ggatttacta ctgcatccac | 360 |
| tgtcacttag gcgcaggagg ggtcacagtc agaagagagc tcagaaatat gctcagcaag | 420 |
| tcttgcagaa ggaatgtcgt cccaagtttg ccaagacatc aatggcgctg ttatttgagc | 480 |
| acaggtatag cgtggactta ctccctttttg tgcagaaggc ccccaaagac agtgaagctg | 540 |
| agtccaagta cgatcctcct tttgggttcc ggaagttctc cagtaaagtc cagaccctct | 600 |
| tggaactctt gccagagcac gacctccctg aacacttgaa agccaagacc tgtcggcgct | 660 |
| gtgtggttat tggaagcgga ggaatactgc acggattaga actgggccac accctgaacc | 720 |
| agttcgatgt tgtgataagg ttaaacagtg caccagttga gggatattca gaacatgttg | 780 |
| gaaataaaac tactataagg atgacttatc cagagggcgc accactgtct gaccttgaat | 840 |
| attattccaa tgacttattt gttgctgttt tatttaagag tgttgatttc aactggcttc | 900 |
| aagcaatggt aaaaaaggaa accctgaacg tccccacaat cggtgtcatt gccgttgtct | 960 |
| tagccacaca tctgtgcgat gaagtcagtt tggcgggttt tggatatgac ctcaatcaac | 1020 |
| ccagaacacc tttgcactac ttcgacagtc aatgcatggc tgctatgaac tttcagacca | 1080 |
| tgcataatgt gacaacggaa accaagttcc tcttaaagct ggtcaaagag ggagtggtga | 1140 |
| aagatctcag tggaggcatt gatcgtgaat tttgaacaca gaaaacctca gttgaaaatg | 1200 |
| caactctaac tctgagagct gttttttgaca gccttcttga tttatttctc catcctgcag | 1260 |
| atactttgaa gtgcagctca tgttttttaac ttttaattta aaaacacaaa aaaaatttta | 1320 |
| gctcttccca cttttttttt cctatttatt tgaggtcagt gtttgttttt gcacaccatt | 1380 |
| ttgtaaatga aacttaagaa ttgaattgga aagacttctc aaagagaatt gtatgtaacg | 1440 |
| atgttgtatt gatttttaag aaagtaattt aatttgtaaa acttctgctc gtttacactg | 1500 |
| cacattgaat acaggtaact aattggaagg agagggagg tcactctttt gatggtggcc | 1560 |
| ctgaacctca ttctggttcc ctgctgcgct gcttggtgtg acccacggag gatccactcc | 1620 |
| caggatgacg tgctccgtag ctctgctgct gatactgggg ctgcgatgca gcggcgtagg | 1680 |
| ctggctggtt gagaaggtca caacccttct ctgttggtct gccttctgct gaaagactcg | 1740 |

```
agaaccaacc agggaagctg tcctgaaggt ccctggtcgg agaggacat agaatctgtg    1800 acctctgaca actgtgaagc caccctgggc tacagaaacc acagtcttcc cagcaattat   1860
tacaattctt gaattccttg ggattttttt actgcccttt caaagcactt aagtgttaga   1920
tctaacgtgt tccagtgtct gtctgaggtg acttaaaaaa tcagaacaaa acttctatta   1980
tccagagtca tgggagagta cacccttccc aggaataatg ttttgggaaa cactgaaatg   2040
aaatcttccc agtattataa attgtgtatt taaaaaaag aaactttct gaatgcctac     2100 ctggcggtgt ataccaggca gtgtcccagt ttaaaaagat gaaaagaat aaaaacttt     2160 gaggaaaaaa aaaaaaaa                                                 2178

<210> SEQ ID NO 7
<211> LENGTH: 1556
<212> TYPE: DNA
<213> ORGANISM: Homo sapiens
<220> FEATURE:
<221> NAME/KEY: CDS
<222> LOCATION: (144)..(1295)

<400> SEQUENCE: 7
ctggcgggag cctgagactc cgggcagggc tgctccctcc tctgctcccc cgccagatcc    60
gcggggaagg aatcgtgccc cgccgccccc tgcccgcgc caccttcctt tggtttctgc    120
cggcctcggg cttctgcggc ccg atg tgg cag gcg ccg cga gag agg cag cag   173
                            Met Trp Gln Ala Pro Arg Glu Arg Gln Gln
                            1                5                   10 ccg gct gga gca gcg gcc cct cag gtc tcg gag ccc ggt gcg cct ctg     221
Pro Ala Gly Ala Ala Ala Pro Gln Val Ser Glu Pro Gly Ala Pro Leu
                15                  20                  25 cgg tcg tcg ctc ctg ggc ctc ggc ggg tca ctc ttg ccg gcc ggc ttc     269
Arg Ser Ser Leu Leu Gly Leu Gly Gly Ser Leu Leu Pro Ala Gly Phe
            30                  35                  40 gct gcg ggt ttg cac tgc ccg ggt gag cca gcc atg aga ggg tat ctt     317
Ala Ala Gly Leu His Cys Pro Gly Glu Pro Ala Met Arg Gly Tyr Leu
        45                  50                  55 gtg gcc ata ttc ctg agt gct gtc ttc ctc tat tat gta ctg cat tgc     365
Val Ala Ile Phe Leu Ser Ala Val Phe Leu Tyr Tyr Val Leu His Cys
    60                  65                  70 ata tta tgg gga acg aat gtc tat tgg gtg gca cct gtg gaa atg aaa     413
Ile Leu Trp Gly Thr Asn Val Tyr Trp Val Ala Pro Val Glu Met Lys
75                  80                  85                  90 cgg aga aat aag atc cag cct tgt tta tca aag cca gct ttt gcc tct     461
Arg Arg Asn Lys Ile Gln Pro Cys Leu Ser Lys Pro Ala Phe Ala Ser
                95                  100                 105 ctg ctg agg ttt cat cag ttt cac cct ttt ctg tgt gcg gct gat ttt    509
Leu Leu Arg Phe His Gln Phe His Pro Phe Leu Cys Ala Ala Asp Phe
            110                 115                 120 aga aag att gct tcc ttg tat ggt agc gat aag ttt gat ttg ccc tat    557
Arg Lys Ile Ala Ser Leu Tyr Gly Ser Asp Lys Phe Asp Leu Pro Tyr
        125                 130                 135 ggg atg aga aca tca gcg gaa tat ttt cga ctt gct ctt tca aaa ctg    605
Gly Met Arg Thr Ser Ala Glu Tyr Phe Arg Leu Ala Leu Ser Lys Leu
    140                 145                 150 cag agt tgt gat ctc ttt gat gag ttt gac aac ata ccc tgt aaa aag    653
Gln Ser Cys Asp Leu Phe Asp Glu Phe Asp Asn Ile Pro Cys Lys Lys
155                 160                 165                 170 tgt gtg gtg gtt ggt aat gga gga gtt ttg aag aat aag aca tta gga    701
Cys Val Val Val Gly Asn Gly Gly Val Leu Lys Asn Lys Thr Leu Gly
                175                 180                 185
```

```
                                                                        -continued gaa aaa atc gac tcc tat gat gta ata ata aga atg aat aat ggt cct         749
Glu Lys Ile Asp Ser Tyr Asp Val Ile Ile Arg Met Asn Asn Gly Pro
        190                 195                 200 gtt tta gga cat gaa gaa gaa gtt ggg aga agg aca acc ttc cga ctt         797
Val Leu Gly His Glu Glu Glu Val Gly Arg Arg Thr Thr Phe Arg Leu
    205                 210                 215 ttt tat cca gaa tct gtt ttt tca gat cct att cac aat gac cct aat         845
Phe Tyr Pro Glu Ser Val Phe Ser Asp Pro Ile His Asn Asp Pro Asn
220                 225                 230 acg aca gtg att ctc act gct ttt aag cca cat gat tta agg tgg ctg         893
Thr Thr Val Ile Leu Thr Ala Phe Lys Pro His Asp Leu Arg Trp Leu
235                 240                 245                 250 ttg gaa ttg ttg atg ggt gac aaa ata aac act aat ggt ttt tgg aag         941
Leu Glu Leu Leu Met Gly Asp Lys Ile Asn Thr Asn Gly Phe Trp Lys
            255                 260                 265 aaa cca gcc tta aac ctg att tat aaa cct tat caa atc cga ata tta         989
Lys Pro Ala Leu Asn Leu Ile Tyr Lys Pro Tyr Gln Ile Arg Ile Leu
        270                 275                 280 gat cct ttc att atc aga aca gca gct tat gaa ctg ctt cat ttt cca        1037
Asp Pro Phe Ile Ile Arg Thr Ala Ala Tyr Glu Leu Leu His Phe Pro
    285                 290                 295 aaa gtg ttt ccc aaa aat cag aaa cct aaa cac cca aca aca gga att        1085
Lys Val Phe Pro Lys Asn Gln Lys Pro Lys His Pro Thr Thr Gly Ile
300                 305                 310 att gcc atc aca ttg gcg ttt tac ata tgt cac gaa gtt cac cta gct        1133
Ile Ala Ile Thr Leu Ala Phe Tyr Ile Cys His Glu Val His Leu Ala
315                 320                 325                 330 ggt ttt aaa tac aac ttt tct gac ctc aag agt cct ttg cac tac tat        1181
Gly Phe Lys Tyr Asn Phe Ser Asp Leu Lys Ser Pro Leu His Tyr Tyr
            335                 340                 345 ggg aat gcc acc atg tct ttg atg aat aag aac gcg tat cac aat gtg        1229
Gly Asn Ala Thr Met Ser Leu Met Asn Lys Asn Ala Tyr His Asn Val
        350                 355                 360 act gca gag cag ctc ttt ttg aag gac att ata gaa aaa aac ctc gta        1277
Thr Ala Glu Gln Leu Phe Leu Lys Asp Ile Ile Glu Lys Asn Leu Val
    365                 370                 375 atc aac ttg act caa gat tgactctaca gactcagaag atgatgctaa               1325
Ile Asn Leu Thr Gln Asp
    380 cagtgttagt tttatttttg tactgcaatt tttagtttaa aatatgttgg atgcactcgt      1385 caaataatta tgtatactgt ctgttgctgc tggtgattca taaccaccag cttaatttct      1445 gtgaatactg tatatttaac ttatgaaaac caagaaatgt aaagataaca ggaaaataag      1505 ttttgattgc aatgttttta aaaaaaaaaa aaaaaaaaa aaaaaaaaa a                 1556

<210> SEQ ID NO 8
<211> LENGTH: 384
<212> TYPE: PRT
<213> ORGANISM: Homo sapiens

<400> SEQUENCE: 8

Met Trp Gln Ala Pro Arg Glu Arg Gln Gln Pro Ala Gly Ala Ala Ala
  1               5                  10                  15

Pro Gln Val Ser Glu Pro Gly Ala Pro Leu Arg Ser Ser Leu Leu Gly
             20                  25                  30

Leu Gly Gly Ser Leu Leu Pro Ala Gly Phe Ala Ala Gly Leu His Cys
         35                  40                  45

Pro Gly Glu Pro Ala Met Arg Gly Tyr Leu Val Ala Ile Phe Leu Ser
     50                  55                  60
```

Ala Val Phe Leu Tyr Tyr Val Leu His Cys Ile Leu Trp Gly Thr Asn
 65                  70                  75                  80

Val Tyr Trp Val Ala Pro Val Glu Met Lys Arg Arg Asn Lys Ile Gln
                 85                  90                  95

Pro Cys Leu Ser Lys Pro Ala Phe Ala Ser Leu Leu Arg Phe His Gln
            100                 105                 110

Phe His Pro Phe Leu Cys Ala Ala Asp Phe Arg Lys Ile Ala Ser Leu
        115                 120                 125

Tyr Gly Ser Asp Lys Phe Asp Leu Pro Tyr Gly Met Arg Thr Ser Ala
    130                 135                 140

Glu Tyr Phe Arg Leu Ala Leu Ser Lys Leu Gln Ser Cys Asp Leu Phe
145                 150                 155                 160

Asp Glu Phe Asp Asn Ile Pro Cys Lys Lys Cys Val Val Val Gly Asn
                165                 170                 175

Gly Gly Val Leu Lys Asn Lys Thr Leu Gly Glu Lys Ile Asp Ser Tyr
            180                 185                 190

Asp Val Ile Ile Arg Met Asn Asn Gly Pro Val Leu Gly His Glu Glu
        195                 200                 205

Glu Val Gly Arg Arg Thr Thr Phe Arg Leu Phe Tyr Pro Glu Ser Val
210                 215                 220

Phe Ser Asp Pro Ile His Asn Asp Pro Asn Thr Thr Val Ile Leu Thr
225                 230                 235                 240

Ala Phe Lys Pro His Asp Leu Arg Trp Leu Leu Glu Leu Leu Met Gly
                245                 250                 255

Asp Lys Ile Asn Thr Asn Gly Phe Trp Lys Lys Pro Ala Leu Asn Leu
            260                 265                 270

Ile Tyr Lys Pro Tyr Gln Ile Arg Ile Leu Asp Pro Phe Ile Ile Arg
        275                 280                 285

Thr Ala Ala Tyr Glu Leu Leu His Phe Pro Lys Val Phe Pro Lys Asn
    290                 295                 300

Gln Lys Pro Lys His Pro Thr Thr Gly Ile Ile Ala Ile Thr Leu Ala
305                 310                 315                 320

Phe Tyr Ile Cys His Glu Val His Leu Ala Gly Phe Lys Tyr Asn Phe
                325                 330                 335

Ser Asp Leu Lys Ser Pro Leu His Tyr Tyr Gly Asn Ala Thr Met Ser
            340                 345                 350

Leu Met Asn Lys Asn Ala Tyr His Asn Val Thr Ala Glu Gln Leu Phe
        355                 360                 365

Leu Lys Asp Ile Ile Glu Lys Asn Leu Val Ile Asn Leu Thr Gln Asp
    370                 375                 380

<210> SEQ ID NO 9
<211> LENGTH: 1622
<212> TYPE: DNA
<213> ORGANISM: Murinae gen. sp.
<220> FEATURE:
<221> NAME/KEY: CDS
<222> LOCATION: (498)..(1484)

<400> SEQUENCE: 9
ggggaacgtt ggcggtctca gcctccgggc cacactgcgc ctcgctccgc tctgctcctt    60
cgccacatcg ggggtagggg tggagggaag ggatcgcgtt cttgtcaccc cgctagctca   120
ggcttccgct cgccgactgc gtcgggaccc gatgctgcag acgccacggg acagacagaa   180
gcgcgctgcg gagagccctg tgcatgcctc tgcggtggcc gagctcgggc ctcggcagca   240

```
cgcacacgtg aagcaacaac aaagcccctc atcttggatt atttccagca tcaagacctc      300
cacatgtcaa cagcaggctc ctgaggcagt ccatcctcct ccaactctcc tcactacatt      360
cttcagaaag agagggtctt caggaacaca ccccaaaagc gcagatttat ttactaattc      420
atgtatttga accatcgtgg aagacctctg catattcatc tcccctcact ttggactctg      480
tttcaggcag gccagcc atg aaa ggg tat ctg gtg gcc ata ttc ctg agt         530
                   Met Lys Gly Tyr Leu Val Ala Ile Phe Leu Ser
                    1               5                      10 tcc atc ttc ctc tat tat gta cta tac tgt ata ctg tgg gga aca aat         578
Ser Ile Phe Leu Tyr Tyr Val Leu Tyr Cys Ile Leu Trp Gly Thr Asn
         15                  20                  25 ggc tat tgg ttc cca gct gaa gaa atg agg act aga aac aat gtc aat         626
Gly Tyr Trp Phe Pro Ala Glu Glu Met Arg Thr Arg Asn Asn Val Asn
         30                  35                  40 aat tgt ttt aaa aag cca gct ttc gcc aat ctt ctg aga ttt cct cag         674
Asn Cys Phe Lys Lys Pro Ala Phe Ala Asn Leu Leu Arg Phe Pro Gln
     45                  50                  55 ctt tac cca ttt ctg tgc aga gct gac ttt ata aag gtt gct gcc atg         722
Leu Tyr Pro Phe Leu Cys Arg Ala Asp Phe Ile Lys Val Ala Ala Met
 60                  65                  70                  75 tcc ggt acc aat aat ttt ccg ttg ccc tat gga ata aag acc ttc gag         770
Ser Gly Thr Asn Asn Phe Pro Leu Pro Tyr Gly Ile Lys Thr Phe Glu
                 80                  85                  90 aca tat ttc agc tcg gcc ctt tca aaa ctg cag agt tgt gat ctc ttt         818
Thr Tyr Phe Ser Ser Ala Leu Ser Lys Leu Gln Ser Cys Asp Leu Phe
             95                 100                 105 gac gag ttt gac aga gtg cca tgt aaa agg tgt gtg gtg gtt ggt aat         866
Asp Glu Phe Asp Arg Val Pro Cys Lys Arg Cys Val Val Val Gly Asn
         110                 115                 120 gga gga gtg ttg aag aat aag aca tta gga gca aca att gac tcc tat         914
Gly Gly Val Leu Lys Asn Lys Thr Leu Gly Ala Thr Ile Asp Ser Tyr
     125                 130                 135 gat gta ata ata aga atg aac aac ggt cct gtc tta ggc cat gaa gag         962
Asp Val Ile Ile Arg Met Asn Asn Gly Pro Val Leu Gly His Glu Glu
140                 145                 150                 155 gaa gtt ggg aca aga aca acc ttc agg ctt ttt tat cca gag tct gtc        1010
Glu Val Gly Thr Arg Thr Thr Phe Arg Leu Phe Tyr Pro Glu Ser Val
                 160                 165                 170 ttt tca gac tcc agt cac tat gac ccc aat act aca gcg gtt ctc gtc        1058
Phe Ser Asp Ser Ser His Tyr Asp Pro Asn Thr Thr Ala Val Leu Val
             175                 180                 185 gtc ttt aag cca cag gat tta agg tgg ctg gtg gaa ata ctg cta ggt        1106
Val Phe Lys Pro Gln Asp Leu Arg Trp Leu Val Glu Ile Leu Leu Gly
         190                 195                 200 aaa aaa ata aat act caa ggg ttt tgg aag aca cca gcc tta aaa ctg        1154
Lys Lys Ile Asn Thr Gln Gly Phe Trp Lys Thr Pro Ala Leu Lys Leu
     205                 210                 215 atc tat aaa caa tac caa atc aga ata tta gat cca tat atc acc agc        1202
Ile Tyr Lys Gln Tyr Gln Ile Arg Ile Leu Asp Pro Tyr Ile Thr Ser
220                 225                 230                 235 gaa gca gct ttt caa atg ctt cgt ttt ccc aga gta ttt ccc aag gat        1250
Glu Ala Ala Phe Gln Met Leu Arg Phe Pro Arg Val Phe Pro Lys Asp
                 240                 245                 250 cag aaa ccc aaa cac cct aca aca gga att att gcc atc aca atg gcc        1298
Gln Lys Pro Lys His Pro Thr Thr Gly Ile Ile Ala Ile Thr Met Ala
             255                 260                 265 ttt cac ata tgc agt gaa gtg cac ctc gct ggt ttt aag tac aac ttt        1346
Phe His Ile Cys Ser Glu Val His Leu Ala Gly Phe Lys Tyr Asn Phe
```

-continued

```
             270                 275                 280
tac agc ccc aac agt cct tta cac tac tac ggg aat gcc acc atg tct    1394
Tyr Ser Pro Asn Ser Pro Leu His Tyr Tyr Gly Asn Ala Thr Met Ser
285                 290                 295 ttg atg aag cag aat gca tat cac aat ctg act gca gag cag ctc ttt    1442
Leu Met Lys Gln Asn Ala Tyr His Asn Leu Thr Ala Glu Gln Leu Phe
300                 305                 310                 315 tta aac gac att ata aag aaa aaa atg gtg atc aac ttg act            1484
Leu Asn Asp Ile Ile Lys Lys Lys Met Val Ile Asn Leu Thr
                320                 325 taaaattgac cctatggatc caaaagatga tgatgctaaa cagtattagt tttatttttg  1544
tactgcaaat tttagtttat ttttaaatat attggatgaa cttatcaaaa aaaaaaaaa   1604 aaaaaaaaaa aaaaaaaa                                                1622

<210> SEQ ID NO 10
<211> LENGTH: 329
<212> TYPE: PRT
<213> ORGANISM: Murinae gen. sp.

<400> SEQUENCE: 10

Met Lys Gly Tyr Leu Val Ala Ile Phe Leu Ser Ser Ile Phe Leu Tyr
 1               5                  10                  15

Tyr Val Leu Tyr Cys Ile Leu Trp Gly Thr Asn Gly Tyr Trp Phe Pro
                20                  25                  30

Ala Glu Glu Met Arg Thr Arg Asn Asn Val Asn Asn Cys Phe Lys Lys
            35                  40                  45

Pro Ala Phe Ala Asn Leu Leu Arg Phe Pro Gln Leu Tyr Pro Phe Leu
        50                  55                  60

Cys Arg Ala Asp Phe Ile Lys Val Ala Ala Met Ser Gly Thr Asn Asn
 65                  70                  75                  80

Phe Pro Leu Pro Tyr Gly Ile Lys Thr Phe Glu Thr Tyr Phe Ser Ser
                85                  90                  95

Ala Leu Ser Lys Leu Gln Ser Cys Asp Leu Phe Asp Glu Phe Asp Arg
            100                 105                 110

Val Pro Cys Lys Arg Cys Val Val Gly Asn Gly Gly Val Leu Lys
        115                 120                 125

Asn Lys Thr Leu Gly Ala Thr Ile Asp Ser Tyr Asp Val Ile Ile Arg
130                 135                 140

Met Asn Asn Gly Pro Val Leu Gly His Glu Glu Val Gly Thr Arg
145                 150                 155                 160

Thr Thr Phe Arg Leu Phe Tyr Pro Glu Ser Val Phe Ser Asp Ser Ser
                165                 170                 175

His Tyr Asp Pro Asn Thr Thr Ala Val Leu Val Val Phe Lys Pro Gln
            180                 185                 190

Asp Leu Arg Trp Leu Val Glu Ile Leu Leu Gly Lys Lys Ile Asn Thr
        195                 200                 205

Gln Gly Phe Trp Lys Thr Pro Ala Leu Lys Leu Ile Tyr Lys Gln Tyr
    210                 215                 220

Gln Ile Arg Ile Leu Asp Pro Tyr Ile Thr Ser Glu Ala Ala Phe Gln
225                 230                 235                 240

Met Leu Arg Phe Pro Arg Val Phe Pro Lys Asp Gln Lys Pro Lys His
                245                 250                 255

Pro Thr Thr Gly Ile Ile Ala Ile Thr Met Ala Phe His Ile Cys Ser
            260                 265                 270
```

```
Glu Val His Leu Ala Gly Phe Lys Tyr Asn Phe Tyr Ser Pro Asn Ser
            275                 280                 285

Pro Leu His Tyr Tyr Gly Asn Ala Thr Met Ser Leu Met Lys Gln Asn
        290                 295                 300

Ala Tyr His Asn Leu Thr Ala Glu Gln Leu Phe Leu Asn Asp Ile Ile
305                 310                 315                 320

Lys Lys Lys Met Val Ile Asn Leu Thr
                325

<210> SEQ ID NO 11
<211> LENGTH: 2992
<212> TYPE: DNA
<213> ORGANISM: Homo sapiens

<400> SEQUENCE: 11
cataattatg ctaaaataaa tcacataact tcctgtctta gacaaagagt cagtattttt      60
tgccagtgtt tcatagtaca tcttagatca tgtttctaac ttgtgcttac ttgatgaaaa     120
aaagctgatg cttctgcatt tgatttcatt actggttgat tgaaaaataa ttgtaatgct     180
tttcatggaa ggacgttagg caaatggcca ctggaaaaaa cccaatgcca ggtggatagt     240
tttggcccta agttttagg ctttggaccc aaatatcggg ctagagaatt ttgaagtctg      300
attatgtact aaatgaggac tacatcaagg ggatctatcc ctacatcttt gccacattct     360
ctgtcctacc cttagtagta gaagacaaaa atagaagaga aagcaaaaag cttactagat     420
tgctactttc ctacaaatcc tattgttggt cacagggaaa atgataaaga aggtgatgaa     480
aaggatctaa atcagcagtc ttttgtcatc agggttgaag tgaccatgtc actcctcagc     540
taacacatta ctatagtcac agcaagtacc ttgggatatt agctcagaca gttgtttgtg     600
caatgaactt gcttccttaa aaatgattta agacatataa ttgtgttttt ctttttaaaaa    660 gtcacccaaa ggttgtcttc acaatatcct aaaactgttt ctatgtttaa tgactttaga    720
aatcaaataa tatcttcatg ttatcctcca aatataattg agatttttg gtctagtgtg     780 ctggtccacc atatttatgt atcttcctta tgtataaatc aaggagtcct tgccattgtg    840
gtattcacaa aagatgtttt cctgcgtaag gagtttacta gcctcacagt tcagaaacct    900
agcaattcta actatgggga ttttgtaccc acaaaaatgg aaaattgtgt ctgtccatga    960
agggtttagg gtatttcctt catttgaat tctgctgatt atagaagaaa attgattagt    1020
ttttaaatat gaattcttca cataactgat gatcattaat aagttttgt attaagctgt    1080 tttcctcttt cccagctaag tctggatcct gccatccacc ccccttttca tttattttcc    1140
ttgttgtgct ctgtcatgtt tcacaatacc cttttaaatt gtggagacaa gtactccatt    1200
caggagcaca caagggccta acttatgcca agaatagaga agagttagaa atgactctca    1260
atagtgtgat ttgtagagtc ccccggatcc caaggcaagg gtctatgaaa cctgttcagg    1320
tcaggtgttt ctgtggtgtt cgctgccggt gtgcgtcagc agatgtggca ggaggaggta    1380
aatagccacg tgcccttggg gtgagtttcg gtttctccag cttcaggga cttctaaaaa    1440 gtgagcctgg ttgcagcttc tacaatgcag taatcctggc ccttctctga aggtccttg    1500 aatcattgct cttggaatca cttctgggtt gctcatcacc tcagcttttc caccctccct    1560
ttccttacat ccatgaatct caggtgtgtg tagggcttgg agaaggtact ggcagacctc    1620
aagaggtgca gggagtattt ttgtttgctg ccacagaacc tctcagtggt ggcatgaatg    1680
agttcccagg gcatttgctt ccctttgggc agggtgcccg gttctggttt ctgactgaca    1740 ttattttgt ctcataggt ggcacctgtg gaaatgaaac ggagaaataa gatccagcct    1800
```

-continued

```
tgtttatcaa agccagcttt tgcctctctg ctgagtcaga gctctgcata tattttaaga    1860
aaaggcattg aggaactcaa tcaaaccagt attcttttca cacaggtttc atcagtttca    1920
cccttttctg tgtgcggctg attttagaaa gattgcttcc ttgtatggta gcgataagtt    1980
tgatttgccc tatgggatga aacatcagc ggaatatttt cgacttgctc tttcaaaact     2040
gcagagttgt gatctctttg atgagtttga caacataccc tgtaaaaagt gtgtggtggt    2100
tggtaatgga ggagttttga agaataagac attaggagaa aaaatcgact cctatgatgt    2160
aataataaga atgaataatg gtcctgtttt aggacatgaa gaagaagttg ggagaaggac    2220
aaccttccga ctttttatc cagaatctgt tttttcagat cctattcaca atgaccctaa     2280
tacgacagtg attctcactg cttttaagcc acatgattta aggtggctgt tggaattgtt    2340
gatgggtgac aaaataaaca ctaatggttt ttggaagaaa ccagccttaa acctgattta    2400
taaaccttat caaatccgaa tattagatcc tttcattatc agaacagcag cttatgaact    2460
gcttcatttt ccaaaagtgt ttcccaaaaa tcagaaacct aaacacccaa caacaggaat    2520
tattgccatc acattggcgt tttacatatg tcacgaagtt cacctagctg ttttaaata    2580 caacttttct gacctcaaga gtcctttgca ctactatggg aatgccacca tgtctttgat    2640
gaataagaac gcgtatcaca atgtgactgc agagcagctc tttttgaagg acattataga    2700
aaaaaacctc gtaatcaact tgactcaaga ttgactctac agactcagaa gatgatgcta    2760
acagtgttag ttttattttt gtactgcaat ttttagttta aatatgttg gatgcactcg      2820 tcaaataatt atgtatactg tctgttgctg ctggtgattc ataaccacca gcttaatttc    2880
tgtgaatact gtatatttaa cttatgaaaa ccaagaaatg taaagataac aggaaaataa    2940
gttttgattg caatgttttt aaaaaaaaaa aaaaaaaaa aaaaaaaaa aa              2992
```

<210> SEQ ID NO 12
<211> LENGTH: 2056
<212> TYPE: DNA
<213> ORGANISM: Homo sapiens
<220> FEATURE:
<221> NAME/KEY: CDS
<222> LOCATION: (181)..(1188)

<400> SEQUENCE: 12

```
ctaatctctg caacagccgc gcttcccggg tcccgcggct cccgcgcgcg atctgccgcg    60
gccggctgct gggcaaaaat cagagccgcc tccgccccat tacccatcat ggaaaccctc    120
caggaaaaag tggccccgga cgcgcgagcc tgaggattct gcacaaaaga ggtgcccaaa    180 atg aag acc ctg atg cgc cat ggt ctg gca gtg tgt tta gcg ctc acc     228
Met Lys Thr Leu Met Arg His Gly Leu Ala Val Cys Leu Ala Leu Thr
  1               5                  10                  15 acc atg tgc acc agc ttg ttg cta gtg tac agc agc ctc ggc ggc cag     276
Thr Met Cys Thr Ser Leu Leu Leu Val Tyr Ser Ser Leu Gly Gly Gln
             20                  25                  30 aag gag cgg ccc ccg cag cag cag cag cag cag cag caa cag cag cag     324
Lys Glu Arg Pro Pro Gln Gln Gln Gln Gln Gln Gln Gln Gln Gln Gln
         35                  40                  45 cag gcg tcg gcc acc ggc agc tcg cag ccg gcg gcg gag agc agc acc     372
Gln Ala Ser Ala Thr Gly Ser Ser Gln Pro Ala Ala Glu Ser Ser Thr
     50                  55                  60 cag cag cgc ccc ggg gtc ccc gcg gga ccg cgg cca ctg gac gga tac     420
Gln Gln Arg Pro Gly Val Pro Ala Gly Pro Arg Pro Leu Asp Gly Tyr
 65                  70                  75                  80 ctc gga gtg gcg gac cac aag ccc ctg aaa atg cac tgc agg gac tgt    468
```

```
Leu Gly Val Ala Asp His Lys Pro Leu Lys Met His Cys Arg Asp Cys
                85                  90                  95 gcc ctg gtg acc agc tca ggg cat ctg ctg cac agt cgg caa ggc tcc      516
Ala Leu Val Thr Ser Ser Gly His Leu Leu His Ser Arg Gln Gly Ser
            100                 105                 110 cag att gac cag aca gag tgt gtc atc cgc atg aat gac gcc ccc aca      564
Gln Ile Asp Gln Thr Glu Cys Val Ile Arg Met Asn Asp Ala Pro Thr
        115                 120                 125 cgc ggc tat ggg cgt gac gtg ggc aat cgc acc agc ctg agg gtc atc      612
Arg Gly Tyr Gly Arg Asp Val Gly Asn Arg Thr Ser Leu Arg Val Ile
    130                 135                 140 gcg cat tcc agc atc cag agg atc ctc cgc aac cgc cat gac ctg ctc      660
Ala His Ser Ser Ile Gln Arg Ile Leu Arg Asn Arg His Asp Leu Leu
145                 150                 155                 160 aac gtg agc cag ggc acc gtg ttc atc ttc tgg ggc ccc agc agc tac      708
Asn Val Ser Gln Gly Thr Val Phe Ile Phe Trp Gly Pro Ser Ser Tyr
                165                 170                 175 atg cgg cgg gac ggc aag ggc cag gtc tac aac aac ctg cat ctc ctg      756
Met Arg Arg Asp Gly Lys Gly Gln Val Tyr Asn Asn Leu His Leu Leu
            180                 185                 190 agc cag gtg ctg ccc cgg ctg aag gcc ttc atg att act cgc cac aag      804
Ser Gln Val Leu Pro Arg Leu Lys Ala Phe Met Ile Thr Arg His Lys
        195                 200                 205 atg ctg cag ttt gat gag ctc ttc aag cag gag act ggc aaa gac agg      852
Met Leu Gln Phe Asp Glu Leu Phe Lys Gln Glu Thr Gly Lys Asp Arg
    210                 215                 220 aag ata tcc aac act tgg ctc agc act ggc tgg ttt aca atg aca att      900
Lys Ile Ser Asn Thr Trp Leu Ser Thr Gly Trp Phe Thr Met Thr Ile
225                 230                 235                 240 gca ctg gag ctc tgt gac agg atc aat gtt tat ggc atg gtg ccc cca      948
Ala Leu Glu Leu Cys Asp Arg Ile Asn Val Tyr Gly Met Val Pro Pro
                245                 250                 255 gac ttc tgc agg gat ccc aat cac cct tca gta cct tat cat tat tat      996
Asp Phe Cys Arg Asp Pro Asn His Pro Ser Val Pro Tyr His Tyr Tyr
            260                 265                 270 gaa cct ttt gga cct gat gaa tgt aca atg tac ctc tcc cat gag cga     1044
Glu Pro Phe Gly Pro Asp Glu Cys Thr Met Tyr Leu Ser His Glu Arg
        275                 280                 285 gga cgc aag ggc agt cat cac cgc ttt atc aca gag aaa cga gtc ttt     1092
Gly Arg Lys Gly Ser His His Arg Phe Ile Thr Glu Lys Arg Val Phe
    290                 295                 300 aag aac tgg gca cgg aca ttc aat att cac ttt ttt caa cca gac tgg     1140
Lys Asn Trp Ala Arg Thr Phe Asn Ile His Phe Phe Gln Pro Asp Trp
305                 310                 315                 320 aaa cca gaa tca ctt gct ata aat cat cct gag aat aaa cct gtg ttc     1188
Lys Pro Glu Ser Leu Ala Ile Asn His Pro Glu Asn Lys Pro Val Phe
                325                 330                 335 taaggaatga gcatgccaga ctgtaatccc aggtattcac tgcatcagac accgagacac   1248
tgaacttcct gagccaccag acaggaaagg gtagcagaaa acagcttcac tcctcaggaa   1308
gtaccatgga cagacgccta ccaggggtga caaagcagtg cagttggatt gtaaggaaaa   1368
attccggaat taatgcatcc taatgaatgt tgtcccttc aatggtgtta ccttaggagc    1428
tgaacattca attcagttac accactatga ctaaaaacag tttggatctc ttagtattgc   1488
ctttgaaact gcaacataag caactcaaca atattagttg cattcctta tagacatacc    1548 atgtcaaaga cgttttcta tcaagttgta ttctttcctg ttctataacc tttgtcatct    1608
gttagactct gtatgtgtga tttgtaaaaa gcaggctgaa actatggaca tgatttctga   1668
```

-continued

```
agagcacatc tccactgact ttcataaagc aaatgtccaa tatttattta ttgagagttt    1728
tttagtgcaa tctgggccag tattttata gattatgatt atgtggtaat ttatccttcc     1788
taactcttta atcctgaatg atggttggaa atggcctaga attaggttac tctgttcaca    1848
atgctcattg ttagcatgca attggtattt gacttggaag tgttgtgttg tatttttga     1908 accctaggc ttcaggaaaa ctgctctttt gtaaaaagaa tagcgatgac atttctaat      1968 gtgcagaaat gttccaaaag gacaaaattg aaaaccaaaa actatgttat taaaacaaaa    2028
aaatgctaac aaaaaaaaaa aaaaaaa                                        2056
```

<210> SEQ ID NO 13
<211> LENGTH: 336
<212> TYPE: PRT
<213> ORGANISM: Homo sapiens

<400> SEQUENCE: 13

```
Met Lys Thr Leu Met Arg His Gly Leu Ala Val Cys Leu Ala Leu Thr
  1               5                  10                  15

Thr Met Cys Thr Ser Leu Leu Val Tyr Ser Ser Leu Gly Gly Gln
             20                  25                  30

Lys Glu Arg Pro Pro Gln Gln Gln Gln Gln Gln Gln Gln Gln
         35                  40                  45

Gln Ala Ser Ala Thr Gly Ser Ser Gln Pro Ala Ala Glu Ser Ser Thr
 50                  55                  60

Gln Gln Arg Pro Gly Val Pro Ala Gly Pro Arg Pro Leu Asp Gly Tyr
 65                  70                  75                  80

Leu Gly Val Ala Asp His Lys Pro Leu Lys Met His Cys Arg Asp Cys
                 85                  90                  95

Ala Leu Val Thr Ser Ser Gly His Leu Leu His Ser Arg Gln Gly Ser
            100                 105                 110

Gln Ile Asp Gln Thr Glu Cys Val Ile Arg Met Asn Asp Ala Pro Thr
        115                 120                 125

Arg Gly Tyr Gly Arg Asp Val Gly Asn Arg Thr Ser Leu Arg Val Ile
130                 135                 140

Ala His Ser Ser Ile Gln Arg Ile Leu Arg Asn Arg His Asp Leu Leu
145                 150                 155                 160

Asn Val Ser Gln Gly Thr Val Phe Ile Phe Trp Gly Pro Ser Ser Tyr
                165                 170                 175

Met Arg Arg Asp Gly Lys Gly Gln Val Tyr Asn Asn Leu His Leu Leu
            180                 185                 190

Ser Gln Val Leu Pro Arg Leu Lys Ala Phe Met Ile Thr Arg His Lys
        195                 200                 205

Met Leu Gln Phe Asp Glu Leu Phe Lys Gln Glu Thr Gly Lys Asp Arg
    210                 215                 220

Lys Ile Ser Asn Thr Trp Leu Ser Thr Gly Trp Phe Thr Met Thr Ile
225                 230                 235                 240

Ala Leu Glu Leu Cys Asp Arg Ile Asn Val Tyr Gly Met Val Pro Pro
                245                 250                 255

Asp Phe Cys Arg Asp Pro Asn His Pro Ser Val Pro Tyr His Tyr Tyr
            260                 265                 270

Glu Pro Phe Gly Pro Asp Glu Cys Thr Met Tyr Leu Ser His Glu Arg
        275                 280                 285

Gly Arg Lys Gly Ser His His Arg Phe Ile Thr Glu Lys Arg Val Phe
    290                 295                 300
```

-continued

Lys Asn Trp Ala Arg Thr Phe Asn Ile His Phe Phe Gln Pro Asp Trp
305                 310                 315                 320

Lys Pro Glu Ser Leu Ala Ile Asn His Pro Glu Asn Lys Pro Val Phe
            325                 330                 335

<210> SEQ ID NO 14
<211> LENGTH: 93
<212> TYPE: PRT
<213> ORGANISM: Murinae gen. sp.

<400> SEQUENCE: 14

Cys Arg Arg Cys Val Val Gly Asn Gly His Arg Leu Arg Asn Ser
1               5                   10                  15

Ser Leu Gly Gly Val Ile Asn Lys Tyr Asp Val Val Ile Arg Leu Asn
            20                  25                  30

Asn Ala Pro Val Ala Gly Tyr Glu Gly Asp Val Gly Ser Lys Thr Thr
        35                  40                  45

Ile Arg Leu Phe Tyr Pro Glu Ser Ala His Arg Ile Leu Asn Pro Phe
    50                  55                  60

Phe Met Cys Asp Leu Val His Ile Ala Gly Phe Gly Tyr Pro Asp Ala
65                  70                  75                  80

Ser Asn Lys Lys Gln Thr Ile His Tyr Tyr Glu Gln Ile
                85                  90

<210> SEQ ID NO 15
<211> LENGTH: 93
<212> TYPE: PRT
<213> ORGANISM: Homo sapiens

<400> SEQUENCE: 15

Cys Arg Arg Cys Val Val Gly Asn Gly His Arg Leu Arg Asn Ser
1               5                   10                  15

Ser Leu Gly Gly Val Ile Asn Lys Tyr Asp Val Val Ile Arg Leu Asn
            20                  25                  30

Asn Ala Pro Val Ala Gly Tyr Glu Gly Asp Val Gly Ser Lys Thr Thr
        35                  40                  45

Ile Arg Leu Phe Tyr Pro Glu Ser Ala His Arg Ile Leu Asn Pro Phe
    50                  55                  60

Phe Met Cys Asp Leu Val His Ile Ala Gly Phe Gly Tyr Pro Asp Ala
65                  70                  75                  80

Ser Asn Lys Lys Gln Thr Ile His Tyr Tyr Glu Gln Ile
                85                  90

<210> SEQ ID NO 16
<211> LENGTH: 93
<212> TYPE: PRT
<213> ORGANISM: Homo sapiens

<400> SEQUENCE: 16

Cys Arg Arg Cys Val Val Gly Asn Gly His Arg Leu Arg Asn Ser
1               5                   10                  15

Ser Leu Gly Asp Ala Ile Asn Lys Tyr Asp Val Val Ile Arg Leu Asn
            20                  25                  30

Asn Ala Pro Val Ala Gly Tyr Glu Gly Asp Val Gly Ser Lys Thr Thr
        35                  40                  45

Met Arg Leu Phe Tyr Pro Glu Ser Ala His Arg Ile Leu Asn Pro Phe
    50                  55                  60

Phe Met Cys Asp Leu Val His Ile Ala Gly Phe Gly Tyr Pro Asp Ala

```
                65                  70                  75                  80
Tyr Asn Lys Lys Gln Thr Ile His Tyr Tyr Glu Gln Ile
                    85                  90

<210> SEQ ID NO 17
<211> LENGTH: 92
<212> TYPE: PRT
<213> ORGANISM: Murinae gen. sp.

<400> SEQUENCE: 17

Cys Arg Arg Cys Ile Ile Val Gly Asn Gly Val Leu Ala Asn Lys
  1               5                  10                  15

Ser Leu Gly Ser Arg Ile Asp Asp Tyr Asp Ile Val Ile Arg Leu Asn
                20                  25                  30

Ser Ala Pro Val Lys Gly Phe Glu Arg Asp Val Gly Ser Lys Thr Thr
            35                  40                  45

Leu Arg Ile Thr Tyr Pro Glu Gly Ala Met Arg Ile Leu Asn Pro Tyr
        50                  55                  60

Phe Ile Cys Asp Glu Val Ala Val Ala Gly Phe Gly Tyr Asp Met Asn
 65                  70                  75                  80

Thr Pro Asn Ala Pro Leu His Tyr Tyr Glu Thr Val
                    85                  90

<210> SEQ ID NO 18
<211> LENGTH: 92
<212> TYPE: PRT
<213> ORGANISM: Rattus gen. sp.

<400> SEQUENCE: 18

Cys Arg Arg Cys Ile Ile Val Gly Asn Gly Val Leu Ala Asn Lys
  1               5                  10                  15

Ser Leu Gly Ser Arg Ile Asp Asp Tyr Asp Ile Val Ile Arg Leu Asn
                20                  25                  30

Ser Ala Pro Val Lys Gly Phe Glu Lys Asp Val Gly Ser Lys Thr Thr
            35                  40                  45

Leu Arg Ile Thr Tyr Pro Glu Gly Ala Met Arg Ile Leu Asn Pro Tyr
        50                  55                  60

Phe Ile Cys Asp Glu Val Ala Val Ala Gly Phe Gly Tyr Asp Met Asn
 65                  70                  75                  80

Thr Pro Asn Ala Pro Leu His Tyr Tyr Glu Thr Val
                    85                  90

<210> SEQ ID NO 19
<211> LENGTH: 92
<212> TYPE: PRT
<213> ORGANISM: Homo sapiens

<400> SEQUENCE: 19

Cys Arg Arg Cys Ile Ile Val Gly Asn Gly Val Leu Ala Asn Lys
  1               5                  10                  15

Ser Leu Gly Ser Arg Ile Asp Asp Tyr Asp Ile Val Arg Leu Asn
                20                  25                  30

Ser Ala Pro Val Lys Gly Phe Glu Lys Asp Val Gly Ser Lys Thr Thr
            35                  40                  45

Leu Arg Ile Thr Tyr Pro Glu Gly Ala Met Arg Ile Leu Asn Pro Tyr
        50                  55                  60

Phe Ile Cys Asp Glu Val Ala Val Ala Gly Phe Gly Tyr Asp Met Ser
 65                  70                  75                  80
```

```
Thr Pro Asn Ala Pro Leu His Tyr Tyr Glu Thr Val
                85                  90

<210> SEQ ID NO 20
<211> LENGTH: 90
<212> TYPE: PRT
<213> ORGANISM: Murinae gen. sp.

<400> SEQUENCE: 20

Cys Arg Arg Cys Ala Val Val Gly Asn Ser Gly Asn Leu Arg Gly Ser
 1               5                  10                  15

Gly Tyr Gly Gln Glu Val Asp Ser His Asn Phe Ile Met Arg Met Asn
             20                  25                  30

Gln Ala Pro Thr Val Gly Phe Glu Lys Asp Val Gly Ser Arg Thr Thr
         35                  40                  45

His His Phe Met Tyr Pro Glu Ser Ala Lys Gln Ile Tyr Asn Pro Ala
     50                  55                  60

Phe Phe Cys Asp Glu Val Asn Val Tyr Gly Phe Gly Ala Asp Ser Arg
 65                  70                  75                  80

Gly Asn Trp His Arg His Trp Glu Asn Asn
                 85                  90

<210> SEQ ID NO 21
<211> LENGTH: 90
<212> TYPE: PRT
<213> ORGANISM: Rattus gen. sp.

<400> SEQUENCE: 21

Cys Arg Arg Cys Ala Val Val Gly Asn Ser Gly Asn Leu Arg Gly Ser
 1               5                  10                  15

Gly Tyr Gly Gln Glu Val Asp Ser His Asn Phe Ile Met Arg Met Asn
             20                  25                  30

Gln Ala Pro Thr Val Gly Phe Glu Lys Asp Val Gly Ser Arg Thr Thr
         35                  40                  45

His His Phe Met Tyr Pro Glu Ser Ala Lys Gln Ile Tyr Asn Pro Ala
     50                  55                  60

Phe Phe Cys Asp Glu Val Asn Val Tyr Gly Phe Gly Ala Asp Ser Arg
 65                  70                  75                  80

Gly Asn Trp His His Tyr Trp Glu Asn Asn
                 85                  90

<210> SEQ ID NO 22
<211> LENGTH: 90
<212> TYPE: PRT
<213> ORGANISM: Homo sapiens

<400> SEQUENCE: 22

Cys Arg Arg Cys Ala Val Val Gly Asn Ser Gly Asn Leu Arg Gly Ser
 1               5                  10                  15

Gly Tyr Gly Gln Asp Val Asp Gly His Asn Phe Ile Met Arg Met Asn
             20                  25                  30

Gln Ala Pro Thr Val Gly Phe Glu Gln Asp Val Gly Ser Arg Thr Thr
         35                  40                  45

His His Phe Met Tyr Pro Glu Ser Ala Lys Gln Ile Tyr Asn Pro Ala
     50                  55                  60

Phe Phe Cys Asp Glu Val Asn Val Tyr Gly Phe Gly Ala Asp Ser Arg
 65                  70                  75                  80
```

Gly Asn Trp His His Tyr Trp Glu Asn Asn
                85                  90

<210> SEQ ID NO 23
<211> LENGTH: 90
<212> TYPE: PRT
<213> ORGANISM: Homo sapiens

<400> SEQUENCE: 23

Cys Arg Arg Cys Ala Val Val Gly Asn Ser Gly Asn Leu Arg Glu Ser
  1               5                  10                  15

Ser Tyr Gly Pro Glu Ile Asp Ser His Asp Phe Val Leu Arg Met Asn
             20                  25                  30

Lys Ala Pro Thr Ala Gly Phe Glu Ala Asp Val Gly Thr Lys Thr Thr
         35                  40                  45

His His Leu Val Tyr Pro Glu Ser Phe Arg Leu Ile Tyr His Pro Ala
     50                  55                  60

Phe Ile Cys Asp Glu Val Asp Leu Tyr Gly Phe Gly Ala Asp Ser Lys
 65                  70                  75                  80

Gly Asn Trp His His Tyr Trp Glu Asn Asn
                85                  90

<210> SEQ ID NO 24
<211> LENGTH: 90
<212> TYPE: PRT
<213> ORGANISM: Murinae gen. sp.

<400> SEQUENCE: 24

Cys Arg Arg Cys Ala Val Val Gly Asn Ser Gly Asn Leu Lys Asp Ser
  1               5                  10                  15

Ser Tyr Gly Pro Glu Ile Asp Ser His Asp Phe Val Leu Arg Met Asn
             20                  25                  30

Lys Ala Pro Thr Val Gly Phe Glu Ala Asp Val Gly Ser Arg Thr Thr
         35                  40                  45

His His Leu Val Tyr Pro Glu Ser Phe Arg Leu Ile Tyr His Pro Ala
     50                  55                  60

Phe Ile Cys Asp Glu Val Asp Leu Tyr Gly Phe Gly Ala Asp Ser Lys
 65                  70                  75                  80

Gly Asn Trp His His Tyr Trp Glu Asn Asn
                85                  90

<210> SEQ ID NO 25
<211> LENGTH: 90
<212> TYPE: PRT
<213> ORGANISM: Pig

<400> SEQUENCE: 25

Cys Arg Arg Cys Ala Val Val Gly Asn Ser Gly Asn Leu Lys Glu Ser
  1               5                  10                  15

Tyr Tyr Gly Pro Gln Ile Asp Ser His Asp Phe Val Leu Arg Met Asn
             20                  25                  30

Lys Ala Pro Thr Glu Gly Phe Glu Ala Asp Val Gly Ser Lys Thr Thr
         35                  40                  45

His His Phe Val Tyr Pro Glu Ser Phe Arg Leu Ile Tyr His Pro Ala
     50                  55                  60

Phe Ile Cys Asp Glu Val Asp Leu Tyr Gly Phe Gly Ala Asp Ser Lys
 65                  70                  75                  80

Gly Asn Trp His His Tyr Trp Glu Asn Asn

<210> SEQ ID NO 26
<211> LENGTH: 90
<212> TYPE: PRT
<213> ORGANISM: Chicken

<400> SEQUENCE: 26

```
Cys Arg Arg Cys Ala Val Val Gly Asn Ser Gly Asn Leu Arg Gln Ser
  1               5                  10                  15
Gln Tyr Gly Gln Asp Ile Asp Ser His Asp Phe Val Leu Arg Met Asn
             20                  25                  30
Arg Ala Pro Thr Ile Gly Tyr Glu Ser Asp Val Gly Ser Lys Thr Thr
         35                  40                  45
His His Phe Val Tyr Pro Glu Ser Tyr Lys Leu Ile Tyr Asn Pro Ser
     50                  55                  60
Phe Ile Cys Asp Glu Val Asn Val Tyr Gly Phe Gly Ala Asp Ser Lys
 65                  70                  75                  80
Gly His Trp His His Tyr Trp Glu Asn Asn
                 85                  90
```

<210> SEQ ID NO 27
<211> LENGTH: 92
<212> TYPE: PRT
<213> ORGANISM: Homo sapiens

<400> SEQUENCE: 27

```
Cys Arg Arg Cys Val Val Ile Gly Ser Gly Gly Ile Leu His Gly Leu
  1               5                  10                  15
Glu Leu Gly His Thr Leu Asn Gln Phe Asp Val Val Ile Arg Leu Asn
             20                  25                  30
Ser Ala Pro Val Glu Gly Tyr Ser Glu His Val Gly Asn Lys Thr Thr
         35                  40                  45
Ile Arg Met Thr Tyr Pro Glu Gly Ala Pro Arg Ile Leu Asn Pro Val
     50                  55                  60
Ile Ile Cys Asp Glu Val Ser Leu Ala Gly Phe Gly Tyr Asp Leu Asn
 65                  70                  75                  80
Gln Pro Arg Thr Pro Leu His Tyr Phe Asp Ser Gln
                 85                  90
```

<210> SEQ ID NO 28
<211> LENGTH: 92
<212> TYPE: PRT
<213> ORGANISM: Murinae gen. sp.

<400> SEQUENCE: 28

```
Cys Lys Arg Cys Val Val Gly Asn Gly Gly Ile Leu His Gly Leu
  1               5                  10                  15
Glu Leu Gly His Ala Leu Asn Gln Phe Asp Val Val Ile Arg Leu Asn
             20                  25                  30
Ser Ala Pro Val Glu Gly Tyr Ser Glu His Val Gly Asn Lys Thr Thr
         35                  40                  45
Ile Arg Met Thr Tyr Pro Glu Gly Ala Pro Arg Ile Leu Asn Pro Val
     50                  55                  60
Ile Ile Cys Asp Glu Val Ser Leu Ala Gly Phe Gly Tyr Asp Leu Ser
 65                  70                  75                  80
Gln Pro Arg Thr Pro Leu His Tyr Phe Asp Ser Gln
                 85                  90
```

<210> SEQ ID NO 29
<211> LENGTH: 92
<212> TYPE: PRT
<213> ORGANISM: Homo sapiens

<400> SEQUENCE: 29

```
Cys Lys Lys Cys Val Val Val Gly Asn Gly Gly Val Leu Lys Asn Lys
 1               5                  10                  15

Thr Leu Gly Glu Lys Ile Asp Ser Tyr Asp Val Ile Ile Arg Met Asn
             20                  25                  30

Asn Gly Pro Val Leu Gly His Glu Glu Glu Val Gly Arg Arg Thr Thr
         35                  40                  45

Phe Arg Leu Phe Tyr Pro Glu Ser Val Phe Arg Ile Leu Asp Pro Phe
     50                  55                  60

Ile Ile Cys His Glu Val His Leu Ala Gly Phe Lys Tyr Asn Phe Ser
 65                  70                  75                  80

Asp Leu Lys Ser Pro Leu His Tyr Tyr Gly Asn Ala
             85                  90
```

<210> SEQ ID NO 30
<211> LENGTH: 92
<212> TYPE: PRT
<213> ORGANISM: Murinae gen. sp.

<400> SEQUENCE: 30

```
Cys Lys Arg Cys Val Val Val Gly Asn Gly Gly Val Leu Lys Asn Lys
 1               5                  10                  15

Thr Leu Gly Ala Thr Ile Asp Ser Tyr Asp Val Ile Ile Arg Met Asn
             20                  25                  30

Asn Gly Pro Val Leu Gly His Glu Glu Glu Val Gly Thr Arg Thr Thr
         35                  40                  45

Phe Arg Leu Phe Tyr Pro Glu Ser Val Phe Arg Ile Leu Asp Pro Tyr
     50                  55                  60

Ile Thr Cys Ser Glu Val His Leu Ala Gly Phe Lys Tyr Asn Phe Tyr
 65                  70                  75                  80

Ser Pro Asn Ser Pro Leu His Tyr Tyr Gly Asn Ala
             85                  90
```

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 31
cctgcaatgg tacacccgag ctcaaagcaa gatga            35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 32
tcatcttgct ttgagctcgg gtgtaccatt gcagg            35

```
<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
tcatcttgct ttgagctcgg gtgta                                          25

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 34
tcatcttgct ttgagct                                                   17

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 35

Cys Arg Arg Cys Val Val Val Gly
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 36

Cys Arg Arg Cys Ile Ile Val Gly
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 37

Cys Lys Arg Cys Val Val Val Gly
  1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 38
```

Cys Lys Lys Cys Val Val Val Gly
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 39

Cys Arg Arg Cys Ala Val Val Gly
  1               5

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: degenerate
      primer

<400> SEQUENCE: 40
tgycgscgst gygtbgtbgt bgg                                               23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: degenerate
      primer

<400> SEQUENCE: 41
tgycgscgst gyatyatygt bgg                                               23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: degenerate
      primer

<400> SEQUENCE: 42
tgyaarcgst gygtbgtbgt bgg                                               23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: degenerate
      primer

<400> SEQUENCE: 43
tgyaaraart gygtbgtbgt bgg                                               23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 44
tgycgscgst gygcngtbgt bgg     23

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 45

Val Val Val Gly Asn Gly Gly
  1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 46

Val Val Val Gly Asn Gly His
  1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 47

Val Val Val Gly Asn Ser Gly
  1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 48

Val Val Val Gly Asn Ser His
  1               5

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 49
gtbgtbgtbg gnaayggngg     20

<210> SEQ ID NO 50
<211> LENGTH: 20

```
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 50
gtbgtbgtbg gnaayggnca                                                       20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 51
gtbgtbgtbg gnaaywsngg                                                       20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 52
gtbgtbgtbg gnaaywsnca                                                       20

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 53

Arg Leu Asn Ser Ala Pro Val
  1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 54

Arg Leu Asn Asn Ala Pro Val
  1               5

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: degenerate
      primer
<220> FEATURE:
```

```
<223> OTHER INFORMATION: "n" = random nucleotide

<400> SEQUENCE: 55
agrytgaayw sngcnccngt                                               20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 56
agrytgaaya ygcnccngt                                                19

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 57

Thr Tyr Pro Glu Gly Ala
  1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 58

Phe Tyr Pro Glu Ser Ala
  1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 59

Thr Tyr Pro Glu Ser Ala
  1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 60

Phe Tyr Pro Glu Gly Ala
  1               5

<210> SEQ ID NO 61
```

```
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 61

Arg Leu Phe Tyr Pro Glu Ser
 1               5

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 62
acntayccng arggngc                                                17

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 63
ttytayccng arwsngc                                                17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 64
acntayccng arwsngc                                                17

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 65
ttytayccng arggngc                                                17

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
```

<220> FEATURE:
<223> OTHER INFORMATION: "n" = random nucleotide

<400> SEQUENCE: 66
mgnctnttyt ayccngarwc                                           20

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 67

Ala Gly Phe Gly Tyr Asp
  1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 68

Tyr Gly Phe Gly Ala Asp
  1               5

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 69
rtcrtanccr aanccngc                                             18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 70
rtcngcnccr aanccrta                                             18

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = Phe or Tyr

<400> SEQUENCE: 71

Arg Ile Leu Asn Pro Xaa

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = His or Asn

<400> SEQUENCE: 72

Ile Tyr Xaa Pro Ala Phe
 1               5

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 73
rwanggrttn arnatnc                                                   17

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 74
raangcnggr tkrtadat                                                  18

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = varying amino acid

<400> SEQUENCE: 75

His Tyr Tyr Asp Xaa
 1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = varying amino acid

<400> SEQUENCE: 76

His Tyr Tyr Glu Xaa
 1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = varying amino acid

<400> SEQUENCE: 77

His Tyr Trp Glu Xaa
 1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = varying amino acid

<400> SEQUENCE: 78

His Tyr Trp Asp Xaa
 1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Xaa = varying amino acid

<400> SEQUENCE: 79

His Tyr Phe Asp Xaa
 1               5

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 80
nnnnnnrtcr tartartg                                               18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 81
nnnnnnytcr tartartg                                               18

```
<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 82
nnnnnnytcc cartartg                                                 18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 83
nnnnnnrtcc cartartg                                                 18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: degenerate
      primer
<220> FEATURE:
<223> OTHER INFORMATION: "n" = random nucleotide

<400> SEQUENCE: 84
nnnnnnrtcr aartartg                                                 18

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 85
atcatcgtgg gcaatggag                                                19

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 86
cctggatgaa atatgggttg ag                                            22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 87
```

```
tattggaagc ggaggaatac tg                                              22
```

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 88

```
ctttcaccac tccctctttg ac                                              22
```

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<222> LOCATION: 1
<223> OTHER INFORMATION: Cys, Leu, Trp, Phe or Tyr
<220> FEATURE:
<222> LOCATION: 2
<223> OTHER INFORMATION: Arg, Lys, Asn, Gln, Gly, Ile or Thr
<220> FEATURE:
<222> LOCATION: 3
<223> OTHER INFORMATION: Arg, Lys, Thr, His, Ser, Ile or Val
<220> FEATURE:
<222> LOCATION: 5
<223> OTHER INFORMATION: Val, Ile Ala or Ser
<220> FEATURE:
<222> LOCATION: 6
<223> OTHER INFORMATION: Val or Ile
<220> FEATURE:
<222> LOCATION: 7
<223> OTHER INFORMATION: Val or Ile
<220> FEATURE:
<222> LOCATION: 8
<223> OTHER INFORMATION: Gly or Ser
<220> FEATURE:
<222> LOCATION: 9
<223> OTHER INFORMATION: Asn or Ser
<220> FEATURE:
<222> LOCATION: 10
<223> OTHER INFORMATION: Gly, Ser or Ala
<220> FEATURE:
<222> LOCATION: 11
<223> OTHER INFORMATION: His or Gly

<400> SEQUENCE: 89

```
Xaa Xaa Xaa Cys Xaa Xaa Xaa Xaa Xaa Xaa Xaa
 1               5                  10
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<222> LOCATION: 2
<223> OTHER INFORMATION: Leu, Met, Cys, Phe or Val
<220> FEATURE:
<222> LOCATION: 3
<223> OTHER INFORMATION: Asn or Ser
<220> FEATURE:
<222> LOCATION: 4
<223> OTHER INFORMATION: Ser, Asn, Gln, Arg, Lys, Phe, Leu or Gly
<220> FEATURE:
<222> LOCATION: 5
<223> OTHER INFORMATION: Ala or Pro
<220> FEATURE:

```
<222> LOCATION: 6
<223> OTHER INFORMATION: Pro, Ile or Val
<220> FEATURE:
<222> LOCATION: 7
<223> OTHER INFORMATION: Val, Thr, Leu or Ile

<400> SEQUENCE: 90

Arg Xaa Xaa Xaa Xaa Xaa Xaa
 1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<222> LOCATION: 1
<223> OTHER INFORMATION: Arg, His, Tyr, Thr, Ile or Val
<220> FEATURE:
<222> LOCATION: 2
<223> OTHER INFORMATION: Leu, Ile, Phe, Gly, Thr or Val
<220> FEATURE:
<222> LOCATION: 3
<223> OTHER INFORMATION: Phe, Thr, Met, Val or Ala
<220> FEATURE:
<222> LOCATION: 4
<223> OTHER INFORMATION: Tyr, Thr, Asn or Ser
<220> FEATURE:
<222> LOCATION: 5
<223> OTHER INFORMATION: Pro, Ser, Val, Ala or His
<220> FEATURE:
<222> LOCATION: 6
<223> OTHER INFORMATION: Glu, Asn, Gln, Ser, Tyr or Thr
<220> FEATURE:
<222> LOCATION: 7
<223> OTHER INFORMATION: Gly, Ser, Thr, Val, Ile or Leu
<220> FEATURE:
<222> LOCATION: 8
<223> OTHER INFORMATION: Ala, Phe, Tyr, Val, Ile, Leu or Met

<400> SEQUENCE: 91

Xaa Xaa Xaa Xaa Xaa Xaa Xaa Xaa
 1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<222> LOCATION: 1
<223> OTHER INFORMATION: Arg, Gln or Leu
<220> FEATURE:
<222> LOCATION: 3
<223> OTHER INFORMATION: Leu or Tyr
<220> FEATURE:
<222> LOCATION: 4
<223> OTHER INFORMATION: Asn or His
<220> FEATURE:
<222> LOCATION: 6
<223> OTHER INFORMATION: Phe, Tyr or Ala

<400> SEQUENCE: 92

Xaa Ile Xaa Xaa Pro Xaa Phe
 1               5

<210> SEQ ID NO 93
<211> LENGTH: 6
<212> TYPE: PRT
```

```
<213> ORGANISM: Artificial Sequence
<220> FEATURE:
<223> OTHER INFORMATION: Description of Artificial Sequence: synthetic
      peptide formula
<220> FEATURE:
<222> LOCATION: 1
<223> OTHER INFORMATION: Ala, Tyr or Phe
<220> FEATURE:
<222> LOCATION: 2
<223> OTHER INFORMATION: Gly or Glu
<220> FEATURE:
<222> LOCATION: 3
<223> OTHER INFORMATION: Phe, Tyr, Ser or Met
<220> FEATURE:
<222> LOCATION: 4
<223> OTHER INFORMATION: Gly, Trp, Ile or Leu
<220> FEATURE:
<222> LOCATION: 5
<223> OTHER INFORMATION: Tyr, Ala, Pro, Thr or Asn
<220> FEATURE:
<222> LOCATION: 6
<223> OTHER INFORMATION: Asp, Pro, Ser, Phe, Asn, Ser, Ala or Glu

<400> SEQUENCE: 93

Xaa Xaa Xaa Xaa Xaa Xaa
  1                   5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<222> LOCATION: 1
<223> OTHER INFORMATION: His, Cys or Arg
<220> FEATURE:
<222> LOCATION: 2
<223> OTHER INFORMATION: Tyr or His
<220> FEATURE:
<222> LOCATION: 3
<223> OTHER INFORMATION: Tyr, Trp or Phe
<220> FEATURE:
<222> LOCATION: 4
<223> OTHER INFORMATION: Asp, Glu, His or Tyr

<400> SEQUENCE: 94

Xaa Xaa Xaa Xaa
```

What is claimed:

1. An isolated nucleic acid, comprising a nucleotide sequence coding for a full-length mammalian GM3-synthase, or, coding for a biologically-active polypeptide fragment thereof, with the proviso that said nucleic acid is not AA604937-1998; AA833733-1998; AA848052-1998; AA648992-1997; AA648973-1997; AI150920-1998; N40410-1996; AA969297-1998; AA429546-1997; AA482611-1997; AI038475-1998; AA386324-1997; AI359060-1999; AA448834-1997; AA827206-1998; AA297799-1997; W56658-1996; AA649318-1997; W56550-1996; AA383443-1997; AI364968-1999; AA428458-1997; AA954095-1998; R93279-1996; T95985-1995; R13431-1995; AI123263-1998; AI089834-1998; R40943-1995; AA383409-1997; AA298186-1997; N98461-1996; AA928319-1998; AA359739-1997; AA934042-1998; AA127477-1996; C01821-1996; R93185-1996; W30980-1996; R88774-1995; AI192267-1998; R18785-1995; AA757529-1998; T95887-1995; T48553-1995; R88773-1995; AA448833-1997; AA395997-1997; AA208995-1997; AA274576-1997; Ai322283-1998; AA117276-1996; W36875-1996; Ai324739-1998; AA068897-1997; AA638055-1997; AA592148-1997; AA038269-1996; AA656084-1997, these numbers being accession numbers and their dates.

2. An isolated nucleic acid of claim 1, wherein said coded-for GM3-synthase has sialyltransferase activity, or, GM3-synthase-specific immunogenic activity.

3. An isolated nucleic acid of claim 1, which is mouse.

4. An isolated nucleic acid of claim 3, wherein the nucleotide sequence codes for amino acid 1 to amino acid 359 as set forth in FIG. 1 (SEQ ID NO:4).

5. An isolated nucleic acid of claim 4, having the nucleotide sequence set forth in FIG. 1 (SEQ ID NO:3).

6. An isolated nucleic acid of claim 1, wherein the nucleotide sequence is operably linked to an expression control sequence.

7. An isolated nucleic acid of claim 1, wherein the nucleic acid codes for said GM3-synthase without interruption.

8. An isolated GM3-synthase of claim 1, having 95% sequence identity to amino acid 1 to amino acid 362 of human sialyltransferase as set forth in FIG. 1 (SEQ ID NO:2) or mouse sialyltransferase amino acid 1 to amino acid 359 as set forth in FIG. 1 (SEQ ID NO:4), wherein said GM3-synthase has a sialyltransferase activity.

9. A method of expressing in transformed host cells, a mammalian GM3-synthase, comprising:
   culturing transformed host cells containing a nucleic acid of claim 1 under conditions effective to express the polypeptide.

10. A transformed host cell containing a nucleic acid of claim 1.

11. A vector comprising a nucleic acid of claim 1.

12. An isolated nucleic acid, comprising a nucleotide sequence coding for a full-length mammalian GM3-synthase, or, coding for a biologically-active polypeptide fragment thereof, and which hybridizes under high stringency conditions to the human or mouse nucleotide sequence set forth in FIG. 1 (SEQ ID NO:3), or a complement thereto, and which has at least 95% sequence identity to said nucleotide sequences, or its complement,
   with the proviso that said nucleic acid is not AA604937-1998; AA833733-1998; AA848052-1998; AA648992-1997; AA648973-1997; AI150920-1998; N40410-1996; AA969297-1998; AA429546-1997; AA482611-1997; AI038475-1998; AA386324-1997; AI359060-1999; AA448834-1997; AA827206-1998; AA297799-1997; W56658-1996; AA649318-1997; W56550-1996; AA383443-1997; AI364968-1999; AA428458-1997; AA954095-1998; R93279-1996; T95985-1995; R13431-1995; AI123263-1998; AI089834-1998; R40943-1995; AA383409-1997; AA298186-1997; N98461-1996; AA928319-1998; AA359739-1997; AA934042-1998; AA127477-1996; C01821-1996; R93185-1996; W30980-1996; R88774-1995; AI192267-1998; R18785-1995; AA757529-1998; T95887-1995; T48553-1995; R88773-1995; AA448833-1997; AA395997-1997; AA208995-1997; AA274576-1997; Ai322283-1998; AA117276-1996; W36875-1996; Ai324739-1998; AA068897-1997; AA638055-1997; AA592148-1997; AA038269-1996; AA656084-1997, these numbers being accession numbers and their dates.

13. An isolated nucleic acid consisting essentially of any continuous sequence of 12–100 base pairs, or a complement thereto, selected from the nucleotide sequence set forth 30 in FIG. 1 (SEQ ID NO:3).

* * * * *

Adverse Decision in Interference

Patent No. 6,280,989, Dmitrik Kapitonov, Robert Yu, NOVEL SIALYLTRANSFERASES, Interference No. 105,389, final judgment adverse to the patentees rendered, December 12, 2005, as to claims 1-3, 6-7, 9-13.

*(Official Gazette April 25, 2006)*